US011414457B2

(12) United States Patent
Scheinberg et al.

(10) Patent No.: US 11,414,457 B2
(45) Date of Patent: Aug. 16, 2022

(54) IMMUNOGENIC WT-1 PEPTIDES AND METHODS OF USE THEREOF

(71) Applicant: Memorial Sloan Kettering Cancer Center, New York, NY (US)

(72) Inventors: David Scheinberg, New York, NY (US); Rena May, Baltimore, MD (US)

(73) Assignee: MEMORIAL SLOAN KETTERING CANCER CENTER, New York, NY (US)

(*) Notice: Subject to any disclaimer, the term of this patent is extended or adjusted under 35 U.S.C. 154(b) by 660 days.

(21) Appl. No.: 16/359,897

(22) Filed: Mar. 20, 2019

(65) Prior Publication Data

US 2019/0270776 A1 Sep. 5, 2019

Related U.S. Application Data

(63) Continuation of application No. 14/995,955, filed on Jan. 14, 2016, now abandoned, which is a continuation of application No. 12/296,777, filed as application No. PCT/US2007/008853 on Apr. 10, 2007, now Pat. No. 9,265,816.

(60) Provisional application No. 60/852,009, filed on Oct. 17, 2006, provisional application No. 60/790,526, filed on Apr. 10, 2006.

(51) Int. Cl.
| | |
|---|---|
| *A61K 39/00* | (2006.01) |
| *C07K 7/08* | (2006.01) |
| *A61K 38/10* | (2006.01) |
| *A61K 38/17* | (2006.01) |
| *C07K 14/47* | (2006.01) |

(52) U.S. Cl.
CPC ............... *C07K 7/08* (2013.01); *A61K 38/10* (2013.01); *A61K 38/177* (2013.01); *A61K 39/001153* (2018.08); *C07K 14/4703* (2013.01); *C07K 14/4748* (2013.01); *A61K 39/00* (2013.01); *A61K 2039/5154* (2013.01); *A61K 2039/53* (2013.01); *A61K 2039/57* (2013.01)

(58) Field of Classification Search
None
See application file for complete search history.

(56) References Cited

U.S. PATENT DOCUMENTS

| | | |
|---|---|---|
| 5,229,115 A | 7/1993 | Lynch |
| 5,622,835 A | 4/1997 | Herlyn et al. |
| 5,633,142 A | 5/1997 | Herlyn et al. |
| 5,726,288 A | 3/1998 | Call et al. |
| 5,981,217 A | 11/1999 | Subramaniam et al. |
| 6,156,316 A | 12/2000 | Scheinberg et al. |
| 6,207,375 B1 | 3/2001 | Subramaniam et al. |
| 6,316,599 B1 | 11/2001 | Call et al. |
| 6,593,299 B1 | 7/2003 | Bennett et al. |
| 6,805,861 B2 | 10/2004 | Stauss |
| 6,861,234 B1 | 3/2005 | Simard et al. |
| 7,030,212 B1 | 4/2006 | Sugiyama et al. |
| 7,063,854 B1 | 6/2006 | Gaiger et al. |
| 7,115,272 B1 | 10/2006 | Gaiger et al. |
| 7,144,581 B2 | 12/2006 | Gaiger et al. |
| 7,323,181 B2 | 1/2008 | Gaiger et al. |
| 7,329,410 B1 | 2/2008 | Gaiger et al. |
| 7,368,119 B2 | 5/2008 | Gaiger et al. |
| 7,420,034 B2 | 9/2008 | Sugiyama et al. |
| 7,488,718 B2 | 2/2009 | Scheinberg et al. |
| 7,517,950 B2 | 4/2009 | Sugiyama et al. |
| 7,553,494 B2 | 6/2009 | Gaiger et al. |
| 7,597,894 B2 | 10/2009 | Graddis et al. |
| 7,598,221 B2 | 10/2009 | Scheinberg et al. |
| 7,608,685 B1 | 10/2009 | Sugiyama et al. |
| 7,655,249 B2 | 2/2010 | Gaiger et al. |
| 7,662,386 B2 | 2/2010 | Gaiger et al. |
| 7,666,985 B2 | 2/2010 | Sugiyama et al. |
| 7,807,792 B2 | 10/2010 | Sugiyama et al. |
| 7,833,775 B2 | 11/2010 | Dubensky et al. |
| 7,901,693 B2 | 3/2011 | Gaiger et al. |
| 7,915,393 B2 | 3/2011 | Gaiger et al. |
| 7,939,627 B2 | 5/2011 | Nishihara et al. |
| 8,071,732 B2 | 12/2011 | Gaiger et al. |
| 8,105,604 B2 | 1/2012 | Sugiyama |
| 8,216,595 B2 | 7/2012 | Moon et al. |
| 8,288,355 B2 | 10/2012 | Sugiyama et al. |
| 8,529,904 B2 | 9/2013 | Stauss et al. |
| 8,557,247 B2 | 10/2013 | Lemoine |
| 8,735,357 B2 | 5/2014 | Sugiyama |
| 8,765,687 B2 | 7/2014 | Scheinberg et al. |
| 8,771,702 B2 | 7/2014 | Paterson et al. |
| 8,778,350 B2 | 7/2014 | Sugiyama |
| 8,920,776 B2 | 12/2014 | Gaiger et al. |

(Continued)

FOREIGN PATENT DOCUMENTS

| | | |
|---|---|---|
| EP | 1447091 A1 | 8/2004 |
| EP | 1961761 A1 | 8/2008 |

(Continued)

OTHER PUBLICATIONS

Bellantuono et al. "Two distinct HLA-A0201-presented epitopes of the Wilms tumor antigen 1 can function as targets for leukemia-reactive CTL" Blood. Nov. 15, 2002;100(10):3835-7.

Bergmann et al. "High levels of Wilms' tumor gene (wt1) mRNA in acute myeloid leukemias are associated with a worse long-term outcome" Blood. Aug. 1, 1997;90(3):1217-25.

Borbulevych et al. "Structures of native and affinity-enhanced WT1 epitopes bound to HLA-A* 0201: implications for WT1-based cancer therapeutics" Molecular immunology. Sep. 30, 2010;47(15):2519-24.

(Continued)

*Primary Examiner* — Zachary S Skelding
(74) *Attorney, Agent, or Firm* — Mark S. Cohen; Pearl Cohen Zedek Latzer Baratz LLP

(57) ABSTRACT

This invention provides peptides, immunogenic compositions and vaccines comprising same, and methods of treating, reducing the incidence of, and inducing immune responses to a WT1-expressing cancer, comprising same.

30 Claims, 16 Drawing Sheets

Specification includes a Sequence Listing.

(56) References Cited

U.S. PATENT DOCUMENTS

| | | |
|---|---|---|
| 9,045,556 B2 | 6/2015 | Udaka et al. |
| 9,181,302 B2 | 11/2015 | Li et al. |
| 9,216,205 B2 | 12/2015 | Chakraborty et al. |
| 9,226,955 B2 | 1/2016 | Hilton et al. |
| 9,233,149 B2 | 1/2016 | Scheinberg et al. |
| 9,248,173 B2 | 2/2016 | Li et al. |
| 9,265,816 B2 | 2/2016 | Scheinberg et al. |
| 9,266,932 B2 | 2/2016 | Sugiyama |
| 9,272,026 B2 | 3/2016 | Sugiyama |
| 9,403,886 B2 | 8/2016 | Sugiyama |
| 9,499,602 B2 | 11/2016 | Paterson et al. |
| 9,518,126 B2 | 12/2016 | Kang et al. |
| 2002/0127718 A1 | 9/2002 | Kuppner et al. |
| 2003/0032050 A1 | 2/2003 | Berzofsky et al. |
| 2003/0045499 A1 | 3/2003 | Gabrilovich et al. |
| 2003/0072761 A1 | 4/2003 | Gaiger et al. |
| 2003/0082194 A1 | 5/2003 | Gaiger et al. |
| 2003/0175272 A1 | 9/2003 | Gruenberg |
| 2004/0018204 A1 | 1/2004 | Gaiger et al. |
| 2005/0002951 A1 | 1/2005 | Sugiyama et al. |
| 2005/0119185 A1 | 6/2005 | Scheinberg et al. |
| 2005/0147621 A1 | 7/2005 | Higgins et al. |
| 2005/0214268 A1 | 9/2005 | Cavanaugh et al. |
| 2005/0221481 A1 | 10/2005 | Migliaccio et al. |
| 2005/0260217 A1 | 11/2005 | Johnson et al. |
| 2006/0057130 A1 | 3/2006 | Nair et al. |
| 2006/0083716 A1 | 4/2006 | Kaufman et al. |
| 2006/0084609 A1 | 4/2006 | Scheinberg et al. |
| 2006/0165708 A1 | 7/2006 | Mayumi et al. |
| 2007/0082860 A1 | 4/2007 | Sugiyama et al. |
| 2007/0128207 A1 | 6/2007 | Sugiyama et al. |
| 2007/0298093 A1 | 12/2007 | Kanur et al. |
| 2008/0070835 A1 | 3/2008 | Sugiyama et al. |
| 2009/0143291 A1 | 6/2009 | Sugiyama et al. |
| 2010/0034842 A1 | 2/2010 | Graddis et al. |
| 2010/0040614 A1 | 2/2010 | Ahmed et al. |
| 2010/0092522 A1 | 4/2010 | Scheinberg et al. |
| 2010/0111986 A1 | 5/2010 | Scheinberg et al. |
| 2010/0166738 A1 | 7/2010 | Gaiger et al. |
| 2010/0247556 A1 | 9/2010 | Sugiyama |
| 2011/0070251 A1 | 3/2011 | Sugiyama et al. |
| 2011/0136141 A1 | 6/2011 | Adamczyk et al. |
| 2011/0223187 A1 | 9/2011 | Shahabi et al. |
| 2011/0287055 A1 | 11/2011 | Lauer et al. |
| 2011/0318380 A1 | 12/2011 | Brix et al. |
| 2012/0301492 A1 | 11/2012 | Gaiger et al. |
| 2013/0064812 A1 | 3/2013 | Gallatin et al. |
| 2013/0196427 A1 | 8/2013 | Sugiyama |
| 2013/0243800 A1 | 9/2013 | Sugiyama |
| 2013/0266958 A1 | 10/2013 | Sugiyam et al. |
| 2014/0086831 A1 | 3/2014 | Scheinberg et al. |
| 2014/0179004 A1 | 6/2014 | Fujii et al. |
| 2014/0220055 A1 | 8/2014 | Okubo et al. |
| 2014/0220057 A1 | 8/2014 | Okubo et al. |
| 2014/0220059 A1 | 8/2014 | Asari et al. |
| 2014/0220105 A1 | 8/2014 | Maeda et al. |
| 2014/0255941 A1 | 9/2014 | Sugiyama |
| 2014/0271693 A1 | 9/2014 | Nakatani |
| 2014/0341939 A1 | 11/2014 | Udaka |
| 2015/0030533 A1 | 1/2015 | Algate et al. |
| 2015/0118208 A1 | 4/2015 | Schmitt et al. |
| 2015/0150975 A1 | 6/2015 | Tanka et al. |
| 2015/0328278 A1 | 11/2015 | Kubo et al. |
| 2015/0329874 A1 | 11/2015 | Fukumura et al. |
| 2015/0352201 A1 | 12/2015 | Scheinberg et al. |
| 2015/0368612 A1 | 12/2015 | Palucka et al. |
| 2016/0058852 A1 | 3/2016 | Ter Meulen et al. |
| 2016/0058854 A1 | 3/2016 | Bender et al. |
| 2016/0068801 A1 | 3/2016 | Lubenau |
| 2016/0084841 A1 | 3/2016 | Sugiyam et al. |
| 2016/0030536 A1 | 4/2016 | Weiner et al. |
| 2016/0114017 A1 | 4/2016 | Okada |
| 2016/0114019 A1 | 4/2016 | Li et al. |
| 2016/0166665 A1 | 6/2016 | Ito |
| 2016/0176939 A1 | 6/2016 | Sugiyama |
| 2016/0201141 A1 | 7/2016 | Albitar et al. |
| 2016/0280756 A1 | 9/2016 | Smith et al. |
| 2016/0317634 A1 | 11/2016 | Springer et al. |
| 2016/0362465 A1 | 12/2016 | Nishimura et al. |
| 2016/0367649 A1 | 12/2016 | Sugiyama |
| 2016/0368948 A1 | 12/2016 | Scheinberg et al. |
| 2017/0007693 A1 | 1/2017 | Weinder et al. |
| 2017/0072038 A1 | 3/2017 | Sugiyam et al. |

FOREIGN PATENT DOCUMENTS

| | | |
|---|---|---|
| EP | 2070947 A1 | 6/2009 |
| EP | 2228072 A1 | 9/2010 |
| EP | 2338509 A2 | 6/2011 |
| EP | 2762156 A1 | 8/2014 |
| EP | 2762159 A1 | 8/2014 |
| EP | 2565201 B1 | 11/2014 |
| EP | 1951281 B1 | 4/2015 |
| EP | 2010209 B1 | 6/2015 |
| EP | 2933261 A1 | 10/2015 |
| EP | 2119778 B1 | 11/2015 |
| EP | 2982681 A1 | 2/2016 |
| EP | 2998740 A1 | 3/2016 |
| EP | 2283112 B1 | 10/2016 |
| EP | 3112378 A1 | 1/2017 |
| EP | 3117836 A1 | 1/2017 |
| WO | WO 1995/029240 | 11/1995 |
| WO | WO 1996/035438 A1 | 11/1996 |
| WO | WO 1997/011091 | 3/1997 |
| WO | WO 1999/038973 A2 | 8/1999 |
| WO | WO 2000/006602 | 2/2000 |
| WO | WO 2000/026249 A1 | 5/2000 |
| WO | WO 2000/037491 | 6/2000 |
| WO | WO 2000/055351 | 9/2000 |
| WO | WO 2001/025273 A2 | 4/2001 |
| WO | WO 2001/062920 | 8/2001 |
| WO | WO 2002/028414 A1 | 4/2002 |
| WO | WO 2003/037060 A2 | 5/2003 |
| WO | WO 2004/111075 A2 | 12/2004 |
| WO | WO 2005/053618 | 6/2005 |
| WO | WO 2007/047764 A2 | 4/2007 |
| WO | WO 2007/120603 | 10/2007 |
| WO | WO 2007/120673 A2 | 10/2007 |
| WO | WO 2010/037395 A2 | 4/2010 |
| WO | WO 2014/113490 | 7/2014 |
| WO | WO 2016/093326 A1 | 6/2016 |
| WO | WO 2016/208332 | 12/2016 |
| WO | WO 2017/049074 | 3/2017 |

OTHER PUBLICATIONS

Bruening et al. "A non-AUG translational initiation event generates novel WT1 isoforms" Journal of Biological Chemistry. Apr. 12, 1996;271(15):8646-54.

Buzyn et al. Peptides derived from the whole sequence of BCR-ABL bind to several class I molecules allowing specific induction of human cytotoxic T lymphocytes European journal of immunology. Aug. 1, 1997;27(8):2066-72.

Call et al. "Isolation and characterization of a zinc finger polypeptide gene at the human chromosome 11 Wilms' tumor locus" Cell. Feb. 9, 1990;60(3):509-20.

Cathcart et al. "All CML patients vaccinated with a multivalent bcr-abl peptide vaccine show specific immune responses in a phase II trial" Blood, 2001. 98(11): p. 728a-728a.

Cathcart et al. "A multivalent bcr-abl fusion peptide vaccination trial in patients with chronic myeloid leukemia". Blood. Feb. 1, 2004;103(3):1037-42.

Cheever et al. "The prioritization of cancer antigens: a national cancer institute pilot project for the acceleration of translational research" Clinical Cancer Research. Sep. 1, 2009;15(17):5323-37.

Chen et al. "Expression patterns of WT-1 and Bcr-Abl measured by TaqMan quantitative real-time RT-PCR during follow-up of leukemia patients with the Ph chromosome" Chinese medical journal. Jul. 2004;117(7):968-71.

Cilloni et al. "Significant correlation between the degree of WT-1 expression and the International Prognostic Scoring System Score

(56) References Cited

OTHER PUBLICATIONS in patients with myelodysplastic syndromes" J Clin Oncol. 2003;21(10):1988-1995.
Clay et al. "Changes in the fine specificity of gp100 (209-217)-reactive T cells in patients following vaccination with a peptide modified at an HLA-A2. 1 anchor residue". The Journal of Immunology. Feb. 1, 1999;162(3):1749-55.
Dao et al. "An immunogenic WT1-derived peptide that induces T cell response in the context of HLA-A* 02: 01 and HLA-A* 24: 02 molecules" OncoImmunology. Feb. 1, 2017;6(2):e1252895.
Database Biosis [online]; Nov. 16, 2003, pinilla Javier et al. "Breaking tolerance to the bcr/abl p201 b2a2 protein by use of mutated, heterocltic breakpoint peptides"; Database accession No. PREV200400147743, Abstract; and Blood vol. 102 No. 11, Nov. 16, 2003, p. 654a, 45th annual meeting of the American Society of Hematology, Dec. 6-9, 2003.
Database Biosis [online]; Nov. 16, 2003, Pinilla Javier et al. "Breaking tolerance to the bcr/abl p201 b2a2 protein by use of mutated, heterocltic breakpoint peptides"; Database accession No. PREV200400147740, Abstract; and Blood vol. 102 No. 11, Nov. 16, 2003, p. 654a, 45th annual meeting of the American Society of Hematology, Dec. 6-9, 2003.
De Groot et al. "An interactive Web site providing major histocompatibility ligand predictions: application to HIV research" AIDS research and human retroviruses. May 1, 1997;13(7):529-31.
Doubrovina et al. "In vitro stimulation with WT1 peptide-loaded Epstein-Barr virus-positive B cells elicits high frequencies of WT1 peptide-specific T cells with in vitro and in vivo tumoricidal activity" Clinical Cancer Research. Nov. 1, 2004;10(21):7207-19.
Doubrovina et al. "Sensitization of Human T Cells with Overlapping Pentadecapeptides Spanning the Wt1 Protein Induces Expansion of Leukemocidal T Cells Specific for Both Previously Identified and Novel WT1 Epitopes" Blood. Nov. 16, 2004;104(11):3873-.
Doubrovina et al. "Generation of T Cells of Desired HLA Restriction Specific for Epitopes of a Self-Antigen, WT1, for the Adoptive Immunotherapy of WT1 Positive Malignancies Using a Panel of Artificial Antigen Presenting Cells Expressing Prevalent HLA Alleles" Blood. Nov. 20, 2009;114(22):4086-.
Doubrovina et al. "Mapping of novel peptides of WT-1 and presenting HLA alleles that induce epitope-specific HLA-restricted T cells with cytotoxic activity against WT-1+ leukemias". Blood. Aug. 23, 2012;120(8):1633-46.
Doubrovina et al. "Leukemia-Reactive Cytotoxic CD8+ and CD4+ T-Cells Specific for Novel WT-1 Epitopes Are Generated In Vitro by Sensitization with Overlapping Pentadecapeptides (15-mers) Spanning the Wilms Tumor Protein" Blood. Nov. 16, 2007;110(11):1810-.
Dyall et al. "Heteroclitic immunization induces tumor immunity" Journal of Experimental Medicine. Nov. 2, 1998;188(9):1553-61.
Elisseeva et al. "Humoral immune responses against Wilms tumor gene WT1product in patients with hematopoietic malignancies" Blood. May 1, 2002;99(9):3272-9.
Ellisen et al. "The Wilms tumor suppressor WT1 directs stage-specific quiescence and differentiation of human hematopoietic progenitor cells" The EMBO Journal. Apr. 17, 2001;20(8):1897-909.
Fujiki et al. "A WT1 protein-derived, naturally processed 16-mer peptide, WT1332, is a promiscuous helper peptide for induction of WT1-specific Th1-type CD4+ T cells" Microbiology and immunology. Dec. 1, 2008;52(12):591-600.
Gaiger et al. "Immunity to WT1 in the animal model and in patients with acute myeloid leukemia" Blood. Aug. 15, 2000;96(4):1480-9.
Gao et al. "Human cytotoxic T lymphocytes specific for Wilms' tumor antigen-1 inhibit engraftment of leukemia-initiating stem cells in non-obese diabetic-severe combined immunodeficient recipients" Transplantation. May 15, 2003;75(9):1429-36.
Gao e al. "Selective elimination of leukemic CD34+ progenitor cells by cytotoxic T lymphocytes specific for WT1" Blood. Apr. 1, 2000;95(7):2198-203.
Gao et al. "Antigen-specific CD4+ T-cell help is required to activate a memory CD8+ T cell to a fully functional tumor killer cell" Cancer research. Nov. 15, 2002;62(22):6438-41.
Gerber et al. "Characterization of Chronic Myeloid Leukemia Stem Cells" American Journal of Hematology. Jan. 1, 2011;86(1):31-7.
Gessler et al. Homozygous deletion in Wilms tumours of a zinc-finger gene identified by chromosome jumping. Nature. Feb. 22, 1990;343(6260):774.
Gillmore et al. "Detection of Wilms' tumor antigen-specific CTL in tumor-draining lymph nodes of patients with early breast cancer" Clinical Cancer Research. Jan. 1, 2006;12(1):34-42.
Graff-Dubois et al. "Generation of CTL recognizing an HLA-A* 0201-restricted epitope shared by MAGE-A1,-A2,-A3,-A4,-A6,-A10, and-A12 tumor antigens: implication in a broad-spectrum tumor immunotherapy" The Journal of Immunology. Jul. 1, 2002;169(1):575-80.
Greco et al. "Two brc-abl junction peptides bind HLA-A3 molecules and allow specific induction of human cytotoxic T lymphocytes". Leukemia. Apr. 1996;10(4):693-9.
Greiner et al. "Leukemia-associated antigens are critical for the proliferation of acute myeloid leukemia cells" Clinical Cancer Research. Nov. 15, 2008;14(22):7161-6.
Haber et al. "Alternative splicing and genomic structure of the Wilms tumor gene WT1" Proceedings of the National Academy of Sciences. Nov. 1, 1991;88(21):9618-22.
Harig et al., "Induction of cytotoxic T-cell responses against immunoglobulin V region-derived peptides modified at human leukocyte antigen-A2 binding residues", Blood, 98 (10), pp. 2999-3005, Nov. 15, 2001 (Nov. 15, 2001).
Healthline.om, "Non-hodgkin's Lymphoma: In Depth-Overview", pp. 1-3, http://www.healthline.com/channel/non-hodgkins-lymphoma indepth-overview, Dec. 2, 2008.
Hosen et al. "Very low frequencies of human normal CD34+ haematopoietic progenitor cells express the Wilms' tumour gene WT1 at levels similar to those in leukaemia cells" British journal of haematology. Feb. 1, 2002;116(2):409-20.
Ibrahim et al. "Identification of a distinct antibacterial domain within the N-lobe of ovotransferrin" Biochimica et Biophysica Acta (BBA)—Molecular Cell Research. Mar. 5, 1998;1401(3):289-303.
International Search Report for PCT application No. PCT/US2013/021448 dated May 22, 2013.
Kaida et al. "Phase 1 trial of Wilms tumor 1 (WT1) peptide vaccine and gemcitabine combination therapy in patients with advanced pancreatic or biliary tract cancer" Journal of Immunotherapy. Jan. 1, 2011;34(1):92-9.
Keilholz et al. "A clinical and immunologic phase 2 trial of Wilms tumor gene product 1 (WT1) peptide vaccination in patients with AML and MDS" Blood. Jun. 25, 2009;113(26):6541-8.
Kelly et al. "Lung Cancer—Vaccines" Cancer journal (Sudbury, Mass.). Sep. 2011;17(5):302.
Kessler et al. "Effects of Epitope Modification on T Cell Receptor-Ligand Binding and Antigen Recognition by Seven H-2Kd-restricted Cytotoxic T Lymphocyte Clones Specific for a Photoreactive Peptide Derivative" Journal of Experimental Medicine. Feb. 17, 1997;185(4):629-40.
Kiecker et al. "Analysis of antigen-specific T-cell responses with synthetic peptides—what kind of peptide for which purpose?" Human immunology. May 31, 2004;65(5):523-36.
Kim et al., "A single amino acid variation within an immunodominant AKR/Gross MuLV cytotoxic T-lymphocyte epitope leads to loss in immunogenicity", Viral Immunology, vol. 11, Issue 4, Jan. 1998. http://doi.org/10.1089/vim.1998.11.197.
King et al. "IL15 can reverse the unresponsiveness of Wilms' tumor antigen-specific CTL in patients with prostate cancer" Clinical cancer research. Feb. 15, 2009;15(4):1145-54.
Kobayashi et al. "Defining MHC class II T helper epitopes for WT1 tumor antigen" Cancer Immunology, Immunotherapy. Jul. 1, 2006;55(7):850-60.
Kreidberg et al. "WT-1 is required for early kidney development" Cell. Aug. 27, 1993;74(4):679-91.

(56) References Cited

OTHER PUBLICATIONS

Krug et al. "WT1 peptide vaccinations induce CD4 and CD8 T cell immune responses in patients with mesothelioma and non-small cell lung cancer." Cancer immunology, immunotherapy 59.10 (2010): 1467-1479.
Lapillonne et al. "High WT1 expression after induction therapy predicts high risk of relapse and death in pediatric acute myeloid leukemia" Journal of Clinical Oncology. Apr. 1, 2006;24(10):1507-15.
Lehe et al. "The Wilms' tumor antigen is a novel target for human CD4+ regulatory T cells: implications for immunotherapy" Cancer Research. Aug. 1, 2008;68(15):6350-9.
Maslak et al. "Vaccination with synthetic analog peptides derived from WT1 oncoprotein induces T-cell responses in patients with complete remission from acute myeloid leukemia." Blood 116.2 (2010): 171-179.
May et al. "Peptide epitopes from the Wilms' tumor 1 oncoprotein stimulate CD4+ and CD8+ T cells that recognize and kill human malignant mesothelioma tumor cells" Clinical Cancer Research. Aug. 1, 2007;13(15):4547-55.
McKee et al. "T cell avidity and tumor recognition: implications and therapeutic strategies" Journal of translational medicine. Sep. 20, 2005;3(1):35.
Meister et al. "Two novel T cell epitope prediction algorithms based on MHC-binding motifs; comparison of predicted and published epitopes from *Mycobacterium tuberculosis* and HIV protein sequences" Vaccine. Jan. 1, 1995;13(6):581-91.
Menssen et al. "Wilms' tumor gene (WT1) expression in lung cancer, colon cancer and glioblastoma cell lines compared to freshly isolated tumor specimens" Journal of cancer research and clinical oncology. Mar. 4, 2000;126(4):226-32.
Murao et al. "High frequencies of less differentiated and more proliferative WT1-specific CD8+ T cells in bone marrow in tumor-bearing patients: An important role of bone marrow as a secondary lymphoid organ" Cancer science. Apr. 1, 2010;101(4):848-54.
Nicholson et al. "Heteroclitic proliferative responses and changes in cytokine profile induced by altered peptides: implications for autoimmunity". Proceedings of the National Academy of Sciences. Jan. 6, 1998;95(1):264-9.
Nieda et al. "Dendritic Cells Stimulate the Expansion of BCR-ABL Specific CD8+ T Cells With Cytotoxic Activity Against Leukemic Cells From Patients With Chronic Myeloid Leukemia". Blood, 1998. 91(3): p. 977-83.
Ochsenreither et al. "Wilms' tumor protein 1 (WT1) peptide vaccination in AML patients: predominant TCR CDR3β sequence associated with remission in one patient is detectable in other vaccinated patients" Cancer Immunology, Immunotherapy. Mar. 1, 2012;61(3):313-22.
Office Action for corresponding Canadian Application No. 2,645,766 dated Apr. 6, 2018.
Ohminami et al. "HLA class I-restricted lysis of leukemia cells by a CD8+ cytotoxic T-lymphocyte clone specific for WT1 peptide" Blood. Jan. 1, 2000;95(1):286-93.
Oka et al. "Human cytotoxic T-lymphocyte responses specific for peptides of the wild-type Wilms' tumor gene (WT1) product" Immunogenetics. Feb. 16, 2000;51(2):99-107.
Oka et al. "Induction of WT1 (Wilms' tumor gene)-specific cytotoxic T lymphocytes by WT1 peptide vaccine and the resultant cancer regression" Proceedings of the National Academy of Sciences of the United States of America. Sep. 21, 2004;101(38):13885-90.
Oka et al. "Cancer immunotherapy targeting Wilms' tumor gene WT1 product" The Journal of Immunology. Feb. 15, 2000;164(4):1873-80.
Parkhurst et al. "Improved induction of melanoma-reactive CTL with peptides from the melanoma antigen gp100 modified at HLA-A* 0201-binding residues" The Journal of Immunology. Sep. 15, 1996;157(6):2539-48.
Parmiani et al. "Cancer immunotherapy with peptide-based vaccines: what have we achieved? Where are we going?" Journal of the National Cancer Institute. Jun. 5, 2002;94(11):805-18.
Pinilla-Ibarz et al. "Improved human T-cell responses against synthetic HLA-0201 analog peptides derived from the WT1 oncoprotein" Leukemia. Nov. 1, 2006;20(11):2025-33.
Pinilla-Ibarz et al. "Synthetic peptide analogs derived from bcr/abl fusion proteins and the induction of heteroclitic human T-cell responses" Haematologica. Jan. 1, 2005;90(10):1324-32.
Pinilla-Ibarz et al. "Vaccination of patients with chronic myelogenous leukemia with bcr-abl oncogene breakpoint fusion peptides generates specific immune responses" Blood. Mar. 1, 2000;95(5):1781-7.
Pinilla-Ibarz et al. "Synthetic analogue bcr/abl fusion peptides improve class I immunogenicity to the native protein" InBlood Nov. 16, 2000 (vol. 96, No. 11, pp. 510A-510A).
Pospori et al. "Specificity for the tumor-associated self-antigen WT1 drives the development of fully functional memory T cells in the absence of vaccination" Blood. Jun. 23, 2011;117(25):6813-24.
Rammensee eet al. "MHC ligands and peptide motifs: first listing" Immunogenetics. Feb. 1, 1995;41(4):178-228.
Rezvani et al. "Leukemia-associated antigen-specific T-cell responses following combined PR1 and WT1 peptide vaccination in patients with myeloid malignancies" Blood. Jan. 1, 2008;111(1):236-42.
Rezvani et al. Repeated PR1 and WT1 peptide vaccination in Montanide-adjuvant fails to induce sustained high-avidity, epitope-specific CD8+ T cells in myeloid malignancies. Haematologica. Mar. 1, 2011;96(3):432-40.
Rezvani et al. "T-cell responses directed against multiple HLA-A* 0201-restricted epitopes derived from Wilms' tumor 1 protein in patients with leukemia and healthy donors: identification, quantification, and characterization" Clinical Cancer Research. Dec. 15, 2005;11(24):8799-807.
Rosenberg et al. "Immunologic and therapeutic evaluation of a synthetic peptide vaccine for the treatment of patients with metastatic melanoma". Nature medicine. Mar. 1998;4(3):321.
Scardino et al. "HER-2/neu and hTERT cryptic epitopes as novel targets for broad spectrum tumor immunotherapy". The Journal of Immunology. Jun. 1, 2002;168(11):5900-6.
Scharnhorst et al. "WT1 proteins: functions in growth and differentiation" Gene. Aug. 8, 2001;273(2):141-61.
Scheibenbogen et al. "CD8 T-cell responses to Wilms tumor gene product WT1 and proteinase 3 in patients with acute myeloid leukemia" Blood. Sep. 15, 2002;100(6):2132-7.
Slansky et al. "Enhanced antigen-specific antitumor immunity with altered peptide ligands that stabilize the MHC-peptide-TCR complex". Immunity. Oct. 1, 2000;13(4):529-38.
Sloand et al. "T-cell immune responses to Wilms tumor 1 protein in myelodysplasia responsive to immunosuppressive therapy" Blood. Mar. 3, 2011;117(9):2691-9.
Smithgall et al. "Identification of a novel WT1 HLA A* 0201-restricted CTL epitope using whole gene in vitro priming" In Blood Nov. 16, 2001 (vol. 98, No. 11, pp. 121A-121A).
Sugiyama H. "WT1 (Wilms' tumor gene 1): biology and cancer immunotherapy" Japanese journal of clinical oncology. Apr. 15, 2010:hyp194.
Supplementary European Search Report for Europpean Application No. 13736176.2 dated May 2, 2016.
Tamaki et al. "The Wilms' tumor gene WT1 is a good marker for diagnosis of disease progression of myelodysplnstic syndromes" Leukemia. Mar. 1, 1999;13:393-9.
Tatsumi et al. "Wilms' tumor gene WT1-shRNA as a potent apoptosis-inducing agent for solid tumors" International journal of oncology. Mar. 1, 2008;32(3):701-12.
Ten Bosch et al. "A BCR-ABL oncoprotein p210b2a2 fusion region sequence is recognized by HLA-DR2a restricted cytotoxic T lymphocytes and presented by HLA-DR matched cells transfected with an li(b2a2) construct" Blood, 1999. 94(3): p. 1038-45.
The MGC project Team: UniProt Accession Q6PI38; Dec. 14, 2011; [online]; available on the internet: http://www.uniprot.org/uniprot/Q6PI38.txt?version=42; downloaded on May 7, 2013.
Tourdot et al. "A general strategy to enhance immunogenicity of low-affinity HLA-A2. 1-associated peptides: implication in the identification of cryptic tumor epitopes" European journal of immunology. Dec. 1, 2000;30(12):3411-21.
Trojan et al. "Generation of cytotoxic T lymphocytes against native and altered peptides of human leukocyte antigen-A* 0201 restricted

(56) References Cited

OTHER PUBLICATIONS epitopes from the human epithelial cell adhesion molecule" Cancer research. Jun. 15, 2001;61(12):4761-5.

Tsuboi et al. "Cytotoxic T-lymphocyte responses elicited to Wilms' tumor gene WT1 product by DNA vaccination" Journal of clinical immunology. May 1, 2000;20(3):195-202.

Tyler et al. "WT1-specific immune responses in patients with high-risk multiple myeloma undergoing allogeneic T cell-depleted hematopoietic stem cell transplantation followed by donor lymphocyte infusions" Blood. Nov. 18, 2011;118(21):1993-.

Valmori et al. "Optimal activation of tumor-reactive T cells by selected antigenic peptide analogues" International immunology. Dec. 1, 1999;11(12):1971-80.

Watson et al. "A prophylactic vaccine for breast cancer?" Breast Cancer Research. Aug. 31, 2010;12(4):310.

Weber et al. "WT1 peptide-specific T cells generated from peripheral blood of healthy donors: possible implications for adoptive immunotherapy after allogeneic stem cell transplantation" Leukemia. Sep. 1, 2009;23(9):1634-42.

Xue et al. "Elimination of human leukemia cells in NOD/SCID mice by WT1-TCR gene-transduced human T cells" Blood. Nov. 1, 2005;106(9):3062-7.

Yang et al. "A tumor suppressor and oncogene: the WT1 story" Leukemia. May 1, 2007;21(5):868-76.

Yotnda et al. "Cytotoxic T cell response against the chimeric p210 BCR-ABL protein in patients with chronic myelogenous leukemia" Journal of Clinical Investigation. May 15, 1998;101(10):2290.

Yu et al. "Methods for prediction of peptide binding to MHC molecules: a comparative study" Molecular Medicine. Mar. 2002;8(3):137.

Zhang et al. "Advances in dendritic cell-based vaccine of cancer" Cancer Biotherapy and Radiopharmaceuticals. Dec. 1, 2002;17(6):601-19.

Zügel et al. "Termination of peripheral tolerance to a T cell epitope by heteroclitic antigen analogues". The Journal of Immunology. Aug. 15, 1998;161(4):1705-9.

SEQUENCE LISTING

<160> NUMBER OF SEQ ID NOS: 59

<210> SEQ ID NO 1
<211> LENGTH: 15
<212> TYPE: PRT
<213> ORGANISM: Homo sapiens

<400> SEQUENCE: 1

Leu Val Arg His His Asn Met His Gln Arg Asn Met Thr Lys Leu
1               5                   10                  15

<210> SEQ ID NO 2
<211> LENGTH: 19
<212> TYPE: PRT
<213> ORGANISM: Homo sapiens

<400> SEQUENCE: 2

Arg Ser Asp Glu Leu Val Arg His His Asn Met His Gln Arg Asn Met
1               5                   10                  15

Thr Lys Leu

<210> SEQ ID NO 3
<211> LENGTH: 15
<212> TYPE: PRT
<213> ORGANISM: Homo sapiens

<400> SEQUENCE: 3

Asn Lys Arg Tyr Phe Lys Leu Ser His Leu Gln Met His Ser Arg
1               5                   10                  15

<210> SEQ ID NO 4
<211> LENGTH: 22
<212> TYPE: PRT
<213> ORGANISM: Homo sapiens

<400> SEQUENCE: 4

Pro Gly Cys Asn Lys Arg Tyr Phe Lys Leu Ser His Leu Gln Met His
1               5                   10                  15

Ser Arg Lys His Thr Gly
            20

<210> SEQ ID NO 5
<211> LENGTH: 9
<212> TYPE: PRT
<213> ORGANISM: Homo sapiens

<400> SEQUENCE: 5

Arg Met Phe Pro Asn Ala Pro Tyr Leu
1               5

<210> SEQ ID NO 6
<211> LENGTH: 9
<212> TYPE: PRT
<213> ORGANISM: Homo sapiens

<400> SEQUENCE: 6

Tyr Met Phe Pro Asn Ala Pro Tyr Leu
1               5

<210> SEQ ID NO 7
<211> LENGTH: 9
<212> TYPE: PRT
<213> ORGANISM: Homo sapiens

```
<400> SEQUENCE: 7

Ser Leu Gly Glu Gln Gln Tyr Ser Val
1               5

<210> SEQ ID NO 8
<211> LENGTH: 9
<212> TYPE: PRT
<213> ORGANISM: Homo sapiens

<400> SEQUENCE: 8

Tyr Leu Gly Glu Gln Gln Tyr Ser Val
1               5

<210> SEQ ID NO 9
<211> LENGTH: 9
<212> TYPE: PRT
<213> ORGANISM: Homo sapiens

<400> SEQUENCE: 9

Ala Leu Leu Pro Ala Val Pro Ser Leu
1               5

<210> SEQ ID NO 10
<211> LENGTH: 9
<212> TYPE: PRT
<213> ORGANISM: Homo sapiens

<400> SEQUENCE: 10

Tyr Leu Leu Pro Ala Val Pro Ser Leu
1               5

<210> SEQ ID NO 11
<211> LENGTH: 9
<212> TYPE: PRT
<213> ORGANISM: Homo sapiens

<400> SEQUENCE: 11

Asn Leu Gly Ala Thr Leu Lys Gly Val
1               5

<210> SEQ ID NO 12
<211> LENGTH: 9
<212> TYPE: PRT
<213> ORGANISM: Homo sapiens

<400> SEQUENCE: 12

Tyr Leu Gly Ala Thr Leu Lys Gly Val
1               5

<210> SEQ ID NO 13
<211> LENGTH: 9
<212> TYPE: PRT
<213> ORGANISM: Homo sapiens

<400> SEQUENCE: 13

Asp Leu Asn Ala Leu Leu Pro Ala Val
1               5

<210> SEQ ID NO 14
<211> LENGTH: 9
<212> TYPE: PRT
<213> ORGANISM: Homo sapiens

<400> SEQUENCE: 14
```

Tyr Leu Asn Ala Leu Leu Pro Ala Val
1               5

<210> SEQ ID NO 15
<211> LENGTH: 9
<212> TYPE: PRT
<213> ORGANISM: Homo sapiens

<400> SEQUENCE: 15

Gly Val Phe Arg Gly Ile Gln Asp Val
1               5

<210> SEQ ID NO 16
<211> LENGTH: 9
<212> TYPE: PRT
<213> ORGANISM: Homo sapiens

<400> SEQUENCE: 16

Gly Leu Arg Arg Gly Ile Gln Asp Val
1               5

<210> SEQ ID NO 17
<211> LENGTH: 9
<212> TYPE: PRT
<213> ORGANISM: Homo sapiens

<400> SEQUENCE: 17

Lys Arg Tyr Phe Lys Leu Ser His Leu
1               5

<210> SEQ ID NO 18
<211> LENGTH: 9
<212> TYPE: PRT
<213> ORGANISM: Homo sapiens

<400> SEQUENCE: 18

Lys Leu Tyr Phe Lys Leu Ser His Leu
1               5

<210> SEQ ID NO 19
<211> LENGTH: 9
<212> TYPE: PRT
<213> ORGANISM: Homo sapiens

<400> SEQUENCE: 19

Ala Leu Leu Leu Arg Thr Pro Tyr Ser
1               5

<210> SEQ ID NO 20
<211> LENGTH: 9
<212> TYPE: PRT
<213> ORGANISM: Homo sapiens

<400> SEQUENCE: 20

Ala Leu Leu Leu Arg Thr Pro Tyr Val
1               5

<210> SEQ ID NO 21
<211> LENGTH: 9
<212> TYPE: PRT
<213> ORGANISM: Homo sapiens

<400> SEQUENCE: 21

Cys Met Thr Trp Asn Gln Met Asn Leu
1               5

```
<210> SEQ ID NO 22
<211> LENGTH: 9
<212> TYPE: PRT
<213> ORGANISM: Homo sapiens

<400> SEQUENCE: 22

Tyr Met Thr Trp Asn Gln Met Asn Leu
1               5

<210> SEQ ID NO 23
<211> LENGTH: 9
<212> TYPE: PRT
<213> ORGANISM: Homo sapiens

<400> SEQUENCE: 23

Asn Met His Gln Arg Asn Met Thr Lys
1               5

<210> SEQ ID NO 24
<211> LENGTH: 9
<212> TYPE: PRT
<213> ORGANISM: Homo sapiens

<400> SEQUENCE: 24

Asn Met Tyr Gln Arg Asn Met Thr Lys
1               5

<210> SEQ ID NO 25
<211> LENGTH: 9
<212> TYPE: PRT
<213> ORGANISM: Homo sapiens

<400> SEQUENCE: 25

Asn Met His Gln Arg Val Met Thr Lys
1               5

<210> SEQ ID NO 26
<211> LENGTH: 9
<212> TYPE: PRT
<213> ORGANISM: Homo sapiens

<400> SEQUENCE: 26

Asn Met Tyr Gln Arg Val Met Thr Lys
1               5

<210> SEQ ID NO 27
<211> LENGTH: 9
<212> TYPE: PRT
<213> ORGANISM: Homo sapiens

<400> SEQUENCE: 27

Gln Met Asn Leu Gly Ala Thr Leu Lys
1               5

<210> SEQ ID NO 28
<211> LENGTH: 9
<212> TYPE: PRT
<213> ORGANISM: Homo sapiens

<400> SEQUENCE: 28

Gln Met Tyr Leu Gly Ala Thr Leu Lys
1               5
```

```
<210> SEQ ID NO 29
<211> LENGTH: 9
<212> TYPE: PRT
<213> ORGANISM: Homo sapiens

<400> SEQUENCE: 29

Gln Met Asn Leu Gly Val Thr Leu Lys
1               5

<210> SEQ ID NO 30
<211> LENGTH: 9
<212> TYPE: PRT
<213> ORGANISM: Homo sapiens

<400> SEQUENCE: 30

Gln Met Tyr Leu Gly Val Thr Leu Lys
1               5

<210> SEQ ID NO 31
<211> LENGTH: 10
<212> TYPE: PRT
<213> ORGANISM: Homo sapiens

<400> SEQUENCE: 31

Phe Met Cys Ala Tyr Pro Gly Cys Asn Lys
1               5                   10

<210> SEQ ID NO 32
<211> LENGTH: 10
<212> TYPE: PRT
<213> ORGANISM: Homo sapiens

<400> SEQUENCE: 32

Phe Met Tyr Ala Tyr Pro Gly Cys Asn Lys
1               5                   10

<210> SEQ ID NO 33
<211> LENGTH: 10
<212> TYPE: PRT
<213> ORGANISM: Homo sapiens

<400> SEQUENCE: 33

Phe Met Cys Ala Tyr Pro Phe Cys Asn Lys
1               5                   10

<210> SEQ ID NO 34
<211> LENGTH: 10
<212> TYPE: PRT
<213> ORGANISM: Homo sapiens

<400> SEQUENCE: 34

Phe Met Tyr Ala Tyr Pro Phe Cys Asn Lys
1               5                   10

<210> SEQ ID NO 35
<211> LENGTH: 10
<212> TYPE: PRT
<213> ORGANISM: Homo sapiens

<400> SEQUENCE: 35

Lys Leu Ser His Leu Gln Met His Ser Arg
1               5                   10

<210> SEQ ID NO 36
<211> LENGTH: 10
```

```
<212> TYPE: PRT
<213> ORGANISM: Homo sapiens

<400> SEQUENCE: 36

Lys Leu Tyr His Leu Gln Met His Ser Arg
1               5                   10

<210> SEQ ID NO 37
<211> LENGTH: 10
<212> TYPE: PRT
<213> ORGANISM: Homo sapiens

<400> SEQUENCE: 37

Lys Leu Ser His Leu Gln Met His Ser Lys
1               5                   10

<210> SEQ ID NO 38
<211> LENGTH: 10
<212> TYPE: PRT
<213> ORGANISM: Homo sapiens

<400> SEQUENCE: 38

Lys Leu Tyr His Leu Gln Met His Ser Lys
1               5                   10

<210> SEQ ID NO 39
<211> LENGTH: 19
<212> TYPE: PRT
<213> ORGANISM: Homo sapiens

<400> SEQUENCE: 39

Ser Gly Gln Ala Arg Met Phe Pro Asn Ala Pro Tyr Leu Pro Ser Cys
1               5                   10                  15

Leu Glu Ser

<210> SEQ ID NO 40
<211> LENGTH: 15
<212> TYPE: PRT
<213> ORGANISM: Homo sapiens

<400> SEQUENCE: 40

Gln Ala Arg Met Phe Pro Asn Ala Pro Tyr Leu Pro Ser Cys Leu
1               5                   10                  15

<210> SEQ ID NO 41
<211> LENGTH: 19
<212> TYPE: PRT
<213> ORGANISM: Homo sapiens

<400> SEQUENCE: 41

Ser Gly Gln Ala Tyr Met Phe Pro Asn Ala Pro Tyr Leu Pro Ser Cys
1               5                   10                  15

Leu Glu Ser

<210> SEQ ID NO 42
<211> LENGTH: 15
<212> TYPE: PRT
<213> ORGANISM: Homo sapiens

<400> SEQUENCE: 42

Gln Ala Tyr Met Phe Pro Asn Ala Pro Tyr Leu Pro Ser Cys Leu
1               5                   10                  15
```

<210> SEQ ID NO 43
<211> LENGTH: 168
<212> TYPE: PRT
<213> ORGANISM: Homo sapiens

<400> SEQUENCE: 43

Met Gly His His His His His His His His Ser Ser Gly His
1               5                   10                  15

Ile Glu Gly Arg His Met Arg Arg Val Pro Gly Val Ala Pro Thr Leu
            20                  25                  30

Val Arg Ser Ala Ser Glu Thr Ser Glu Lys Arg Pro Phe Met Cys Ala
        35                  40                  45

Tyr Pro Gly Cys Asn Lys Arg Tyr Phe Lys Leu Ser His Leu Gln Met
    50                  55                  60

His Ser Arg Lys His Thr Gly Glu Lys Pro Tyr Gln Cys Asp Phe Lys
65                  70                  75                  80

Asp Cys Glu Arg Arg Phe Phe Arg Ser Asp Gln Leu Lys Arg His Gln
                85                  90                  95

Arg Arg His Thr Gly Val Lys Pro Phe Gln Cys Lys Thr Cys Gln Arg
            100                 105                 110

Lys Phe Ser Arg Ser Asp His Leu Lys Thr His Thr Arg Thr His Thr
        115                 120                 125

Gly Glu Lys Pro Phe Ser Cys Arg Trp Pro Ser Cys Gln Lys Lys Phe
    130                 135                 140

Ala Arg Ser Asp Glu Leu Val Arg His His Asn Met His Gln Arg Asn
145                 150                 155                 160

Met Thr Lys Leu Gln Leu Ala Leu
                165

<210> SEQ ID NO 44
<211> LENGTH: 18
<212> TYPE: PRT
<213> ORGANISM: Homo sapiens

<400> SEQUENCE: 44

Gly Ala Thr Leu Lys Gly Val Ala Ala Gly Ser Ser Ser Ser Val Lys
1               5                   10                  15

Trp Thr

<210> SEQ ID NO 45
<211> LENGTH: 15
<212> TYPE: PRT
<213> ORGANISM: Homo sapiens

<400> SEQUENCE: 45

Leu Lys Gly Val Ala Ala Gly Ser Ser Ser Val Lys Trp Thr
1               5                   10                  15

<210> SEQ ID NO 46
<211> LENGTH: 449
<212> TYPE: PRT
<213> ORGANISM: Homo sapiens

<400> SEQUENCE: 46

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr

```
            35                  40                  45
Gly Ser Leu Gly Gly Pro Ala Pro Pro Ala Pro Pro Pro Pro
 50                  55                  60

Pro Pro Pro Pro His Ser Phe Ile Lys Gln Glu Pro Ser Trp Gly Gly
 65                  70                  75                  80

Ala Glu Pro His Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
                100                 105                 110

Gly Pro Pro Pro Pro Ser Gln Ala Ser Ser Gly Gln Ala Arg Met Phe
                115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
                275                 280                 285

His Thr His Gly Val Phe Arg Gly Ile Gln Asp Val Arg Arg Val Pro
                290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
                355                 360                 365

Gln Leu Lys Arg His Gln Arg Arg His Thr Gly Val Lys Pro Phe Gln
                370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
                435                 440                 445

Leu
```

<210> SEQ ID NO 47
<211> LENGTH: 453
<212> TYPE: PRT
<213> ORGANISM: Homo sapiens

<400> SEQUENCE: 47

```
Ala Ala Glu Ala Ser Ala Glu Arg Leu Gln Gly Arg Arg Ser Arg Gly
  1               5                  10                  15

Ala Ser Gly Ser Glu Pro Gln Gln Met Gly Ser Asp Val Arg Asp Leu
             20                  25                  30

Asn Ala Leu Leu Pro Ala Val Pro Ser Leu Gly Gly Gly Gly Gly Cys
         35                  40                  45

Ala Leu Pro Val Ser Gly Ala Ala Gln Trp Ala Pro Val Leu Asp Phe
     50                  55                  60

Ala Pro Pro Gly Ala Ser Ala Tyr Gly Ser Leu Gly Gly Pro Ala Pro
 65                  70                  75                  80

Pro Pro Ala Pro Pro Pro Pro Pro Pro Pro His Ser Phe Ile
             85                  90                  95

Lys Gln Glu Pro Ser Trp Gly Gly Ala Glu Pro His Glu Glu Gln Cys
            100                 105                 110

Leu Ser Ala Phe Thr Val His Phe Ser Gly Gln Phe Thr Gly Thr Ala
        115                 120                 125

Gly Ala Cys Arg Tyr Gly Pro Phe Gly Pro Pro Pro Ser Gln Ala
    130                 135                 140

Ser Ser Gly Gln Ala Arg Met Phe Pro Asn Ala Pro Tyr Leu Pro Ser
145                 150                 155                 160

Cys Leu Glu Ser Gln Pro Ala Ile Arg Asn Gln Gly Tyr Ser Thr Val
                165                 170                 175

Thr Phe Asp Gly Thr Pro Ser Tyr Gly His Thr Pro Ser His His Ala
            180                 185                 190

Ala Gln Phe Pro Asn His Ser Phe Lys His Glu Asp Pro Met Gly Gln
        195                 200                 205

Gln Gly Ser Leu Gly Glu Gln Gln Tyr Ser Val Pro Pro Pro Val Tyr
    210                 215                 220

Gly Cys His Thr Pro Thr Asp Ser Cys Thr Gly Ser Gln Ala Leu Leu
225                 230                 235                 240

Leu Arg Thr Pro Tyr Ser Ser Asp Asn Leu Tyr Gln Met Thr Ser Gln
                245                 250                 255

Leu Glu Cys Met Thr Trp Asn Gln Met Asn Leu Gly Ala Thr Leu Lys
            260                 265                 270

Gly His Ser Thr Gly Tyr Glu Ser Asp Asn His Thr Thr Pro Ile Leu
        275                 280                 285

Cys Gly Ala Gln Tyr Arg Ile His Thr His Gly Val Phe Arg Gly Ile
    290                 295                 300

Gln Asp Val Arg Arg Val Pro Gly Val Ala Pro Thr Leu Val Arg Ser
305                 310                 315                 320

Ala Ser Glu Thr Ser Glu Lys Arg Pro Phe Met Cys Ala Tyr Pro Gly
                325                 330                 335

Cys Asn Lys Arg Tyr Phe Lys Leu Ser His Leu Gln Met His Ser Arg
            340                 345                 350

Lys His Thr Gly Glu Lys Pro Tyr Gln Cys Asp Phe Lys Asp Cys Glu
        355                 360                 365

Arg Arg Phe Ser Arg Ser Asp Gln Leu Lys Arg His Gln Arg Arg His
    370                 375                 380
```

```
Thr Gly Val Lys Pro Phe Gln Cys Lys Thr Cys Gln Arg Lys Phe Ser
385                 390                 395                 400

Arg Ser Asp His Leu Lys Thr His Thr Arg Thr His Thr Gly Glu Lys
                405                 410                 415

Pro Phe Ser Cys Arg Trp Pro Ser Cys Gln Lys Lys Phe Ala Arg Ser
            420                 425                 430

Asp Glu Leu Val Arg His His Asn Met His Gln Arg Asn Met Thr Lys
        435                 440                 445

Leu Gln Leu Ala Leu
    450

<210> SEQ ID NO 48
<211> LENGTH: 514
<212> TYPE: PRT
<213> ORGANISM: Homo sapiens

<400> SEQUENCE: 48

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
```

```
                    290                 295                 300
Thr Trp Asn Gln Met Asn Leu Gly Ala Thr Leu Lys Gly Val Ala Ala
305                 310                 315                 320

Gly Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Pro Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
            420                 425                 430

Ser Arg Ser Asp Gln Leu Lys Arg His Gln Arg Arg His Thr Gly Val
        435                 440                 445

Lys Pro Phe Gln Cys Lys Thr Cys Gln Arg Lys Phe Ser Arg Ser Asp
    450                 455                 460

His Leu Lys Thr His Thr Arg Thr His Thr Gly Glu Lys Pro Phe Ser
465                 470                 475                 480

Cys Arg Trp Pro Ser Cys Gln Lys Lys Phe Ala Arg Ser Asp Glu Leu
                485                 490                 495

Val Arg His His Asn Met His Gln Arg Asn Met Thr Lys Leu Gln Leu
            500                 505                 510

Ala Leu

<210> SEQ ID NO 49
<211> LENGTH: 21
<212> TYPE: PRT
<213> ORGANISM: Homo sapiens

<400> SEQUENCE: 49

Thr Glu Tyr Lys Leu Val Val Val Gly Ala Pro Gly Val Gly Lys Ser
1               5                   10                  15

Ala Leu Thr Ile Gln
            20

<210> SEQ ID NO 50
<211> LENGTH: 23
<212> TYPE: PRT
<213> ORGANISM: Homo sapiens

<400> SEQUENCE: 50

Val His Ser Ile Pro Leu Thr Ile Asn Lys Glu Glu Ala Leu Gln Arg
1               5                   10                  15

Pro Val Ala Ser Asp Phe Glu
            20

<210> SEQ ID NO 51
<211> LENGTH: 9
<212> TYPE: PRT
<213> ORGANISM: Human immunodeficiency virus

<400> SEQUENCE: 51
```

Ile Leu Lys Glu Pro Val His Gly Val
1               5

<210> SEQ ID NO 52
<211> LENGTH: 9
<212> TYPE: PRT
<213> ORGANISM: Homo sapiens

<400> SEQUENCE: 52

Tyr Leu Lys Ala Leu Gln Arg Pro Tyr
1               5

<210> SEQ ID NO 53
<211> LENGTH: 28
<212> TYPE: DNA
<213> ORGANISM: Artificial
<220> FEATURE:
<223> OTHER INFORMATION: chemically synethesized

<400> SEQUENCE: 53
caggctgcaa taagagatat tttaagct                                      28

<210> SEQ ID NO 54
<211> LENGTH: 25
<212> TYPE: DNA
<213> ORGANISM: Artificial
<220> FEATURE:
<223> OTHER INFORMATION: chemically synthesized

<400> SEQUENCE: 54
gaagtcacac tggtatggtt tctca                                         25

<210> SEQ ID NO 55
<211> LENGTH: 29
<212> TYPE: DNA
<213> ORGANISM: Artificial
<220> FEATURE:
<223> OTHER INFORMATION: chemically synthesized

<400> SEQUENCE: 55
cttacagatg cacagcagga agcacactg                                     29

<210> SEQ ID NO 56
<211> LENGTH: 29
<212> TYPE: DNA
<213> ORGANISM: Artificial
<220> FEATURE:
<223> OTHER INFORMATION: chemically synthesized

<400> SEQUENCE: 56
cttacagatg cacagcagga agcacactg                                     29

<210> SEQ ID NO 57
<211> LENGTH: 31
<212> TYPE: DNA
<213> ORGANISM: Artificial
<220> FEATURE:
<223> OTHER INFORMATION: chemically synthesized

<400> SEQUENCE: 57
tggagataac actctaagca taactaaagg t                                  31

<210> SEQ ID NO 58
<211> LENGTH: 21
<212> TYPE: DNA
<213> ORGANISM: Artificial

```
<220> FEATURE:
<223> OTHER INFORMATION: chemically synthesized

<400> SEQUENCE: 58
gatgtagttg cttgggaccc a                                              21

<210> SEQ ID NO 59
<211> LENGTH: 28
<212> TYPE: DNA
<213> ORGANISM: Artificial
<220> FEATURE:
<223> OTHER INFORMATION: chemically synthesized

<400> SEQUENCE: 59
ccatttttgg tttgggcttc acaccatt                                       28
```

IMMUNOGENIC WT-1 PEPTIDES AND METHODS OF USE THEREOF

GOVERNMENT INTEREST STATEMENT

This invention was made with government support under CA023766 and CA270043 awarded by the National Institutes of Health. The government has certain rights in the invention.

FIELD OF INVENTION

This invention provides peptides, compositions and vaccines comprising same, and methods of treating, reducing the incidence of, and inducing immune responses to a WT1-expressing cancer, comprising administering same.

BACKGROUND OF THE INVENTION

Wilms tumor (WT), a pediatric nephroblastoma that occurs with a frequency of 1 in 10,000 births, has been the subject of intense clinical and basic research for several years. The tumor is embryonic in origin, it is detected in children usually during the first 5 years of life and can occur unilaterally or bilaterally. A WT arises when condensed metanephric mesenchymal cells of the developing kidney fail to properly differentiate. The implication of the Wilms tumor 1 (WT1) tumor suppressor gene in the etiology of WT illustrated the impact that genetic alterations can have on both development and tumorigenesis.

SUMMARY OF THE INVENTION

This invention provides peptides, compositions, and immunogenic compositions such as vaccines comprising same, and methods of treating, reducing the incidence of, and inducing immune responses to a WT1-expressing cancer, comprising administering same.

In one embodiment, the present invention provides an isolated, mutated WT1 peptide, comprising: (a) a binding motif of a human leukocyte antigen (HLA) Class II molecule; and (b) a binding motif of an HLA class I molecule comprising a point mutation in one or more anchor residues of the binding motif of an HLA class I molecule. In another embodiment, the peptide is 11 or more amino acids in length. In certain other embodiments, the peptide is 11-22, 11-30, 16-22 or 16-30 amino acids in length. In another embodiment, the point mutation is in 1-3 anchor residues of the HLA class I molecule binding motif. In another embodiment, the point mutation is in 1 anchor residue of the HLA class I molecule binding motif. In another embodiment, the point mutation is in 2 anchor residues of the HLA class I molecule binding motif. In another embodiment, the point mutation is in 1-2 anchor residues of the HLA class I molecule binding motif. In another embodiment, the point mutation is in 2-3 anchor residues of the HLA class I molecule binding motif. In another embodiment, the point mutation is in 1-4 anchor residues of the HLA class I molecule binding motif. Each possibility represents a separate embodiment of the present invention.

In another embodiment, the present invention provides an isolated peptide comprising the amino acid (AA) sequence SGQAYMFPNAPYLPSCLES (SEQ ID No: 41). In another embodiment, the AA sequence of the isolated peptide consists of SEQ ID No: 41. In another embodiment, the AA sequence of the isolated peptide consists of a fragment of SEQ ID No: 41. In another embodiment, the AA sequence of the isolated peptide comprises a fragment of SEQ ID No: 41. Each possibility represents a separate embodiment of the present invention.

In another embodiment, the present invention provides an isolated peptide comprising the AA sequence SGQARMFPNAPYLPSCLES (SEQ ID No: 39). In another embodiment, the AA sequence of the isolated peptide consists of SEQ ID No: 39. In another embodiment, the AA sequence of the isolated peptide consists of a fragment of SEQ ID No: 39. In another embodiment, the AA sequence of the isolated peptide comprises a fragment of SEQ ID No: 39. Each possibility represents a separate embodiment of the present invention.

In another embodiment, the present invention provides an isolated peptide comprising the AA sequence QAYMFPNAPYLPSCL (SEQ ID No: 42). In another embodiment, the AA sequence of the isolated peptide consists of SEQ ID No: 42. In another embodiment, the AA sequence of the isolated peptide consists of a fragment of SEQ ID No: 42. In another embodiment, the AA sequence of the isolated peptide comprises a fragment of SEQ ID No: 42. Each possibility represents a separate embodiment of the present invention.

In another embodiment, the present invention provides a composition comprising an isolated peptide of the invention in combination with at least 1 additional WT1 peptide. In certain embodiments, a composition comprising at least 2 different isolated peptides of the present invention is provided. In certain embodiments, a composition comprising at least 3 or at least 4 different isolated peptides of the present invention is provided. Each possibility represents a separate embodiment of the present invention. In certain embodiments, the composition of the present invention is a vaccine.

The additional WT1 peptide, in another embodiment, has the sequence QARMFPNAPYLPSCL (SEQ ID No: 40). In another embodiment, the additional WT1 peptide comprises the sequence QARMFPNAPYLPSCL. LVRHHN MHQR NMTKL (SEQ ID No: 1); RSDELVRHHNMHQRNMTKL (SEQ ID No: 2); NKRYFKLSHLQMHSR (SEQ ID No: 3); and PGCNKRYFKLSHLQMHSRKHTG (SEQ ID No: 4). In another embodiment, the AA sequence of the additional WT1 peptide is selected from the sequences set forth in SEQ ID No: 5-38. In another embodiment, the additional WT peptide is a heteroclitic peptide selected from SEQ ID No: 5-38. In another embodiment, the additional WT peptide is a wild-type peptide selected from SEQ ID No: 5-38. In another embodiment, the additional WT peptide is another heteroclitic WT1 peptide. In another embodiment, the additional WT peptide is another wild-type WT1 peptide. In another embodiment, the additional WT peptide is any other WT1 peptide known in the art. Each possibility represents a separate embodiment of the present invention.

In another embodiment, the present invention provides a method of treating a subject with a WT1-expressing cancer, the method comprising administering to the subject a peptide or composition of the present invention, thereby treating a subject with a WT1-expressing cancer.

In another embodiment, the present invention provides a method of reducing the incidence of a WT1-expressing cancer, or its relapse, in a subject, the method comprising administering to the subject a peptide or composition of the present invention, thereby reducing the incidence of a WT1-expressing cancer, or its relapse, in a subject.

In another embodiment, the present invention provides a method of inducing formation and proliferation of a WT1 protein-specific CTL, the method comprising contacting a lymphocyte population with a peptide or composition of the present invention, thereby inducing formation and proliferation of a WT1 protein-specific CTL.

In another embodiment, the present invention provides a method of inducing formation and proliferation of (a) a WT1 protein-specific CD8+ lymphocyte; and (b) a CD4+ lymphocyte specific for the WT1 protein, the method comprising contacting a lymphocyte population with a peptide or composition of the present invention, thereby inducing formation and proliferation of (a) a WT1 protein-specific CD8+ lymphocyte; and (b) a CD4+ lymphocyte specific for the WT1 protein.

BRIEF DESCRIPTION OF THE FIGURES

FIG. 5A. Gamma interferon ELISPOT after stimulation with WT1 peptides of CD3+ T cells from healthy donors with different HLA-DRB1 types. FIG. 5B. CD3+ T cells (A: HLA-DRB1*1001/1501; B: HLA-DRB1*0701/1202; C: HLA-DRB1*0301/901; D: HLA-DRB1*0407/1302) were stimulated twice with peptide WT1DR 328 or WT1DR 423. Stimulated T cells were challenged in an IFN-gamma ELISPOT assay with the following: Grey Bars: unchallenged control; Black Bars: CD14+ cells pulsed with stimulating peptide (either WT1DR 328 or WT1DR 423); White Bars: CD14+ cells pulsed with irrelevant CD4+ peptide epitope (RAS); Hatched Bars: unpulsed CD14+ cells. *-p<0.05 compared to controls. Y axis: number of spots per 1×105 CD3+ T cells. X axis: peptide used for T cell stimulations.

FIG. 6A. CD3+ T cells from an HLA A0201/301 DRB1*1301/1302 healthy donor were stimulated with autologous DCs previously incubated with 697 tumor lysates, then challenged in an IFN-gamma ELISPOT assay with autologous DCs previously incubated with either 697 tumor lysate, individual WT1 peptides, control peptides or unpulsed DCs (X axis). FIG. 6B. CD3+ T cells from an HLA A0201/101 DRB1*0301/1601 healthy donor were stimulated with autologous DCs previously incubated with tumor lysates from either JMN (Black Bars), or MeWo (White Bars). T cells were challenged in an IFN-gamma ELISPOT assay with autologous DCs previously incubated with JMN or MeWo tumor lysates, individual WT1DR peptides, or control class II peptide (X axis). Hatched bars: background level of spots from autologous DCs incubated in the absence of T cells. *-P<0.05 compared to control peptides. Y axis: number of spots per $1 \times 10^5$ CD3+ cells.

FIG. 7A. CD3+ gamma interferon ELISPOT with peptides WT1DR 122 and WT1DR 122A1. CD3+ T cells from healthy donors with different HLA-DRB1 types (A: HLA-DRB1*1401; FIG. 7B: HLA-DRB1*0104/1104) were stimulated twice with either peptide WT1DR 122 or WT1DR 122A1, then challenged in an IFN-gamma ELISPOT assay with the following: CD14+ cells pulsed with peptide WT1DR 122 (Grey Bars); CD14+ cells pulsed with peptide WT1DR 122A1 (Black Bars); CD14+ cells pulsed with irrelevant CD4 peptide epitope (White Bars; RAS); unpulsed CD14+ cells (Hatched Bars). *-p<0.05 compared to controls. Y axis: number of spots per $1 \times 10^5$ CD3+ T cells. X axis: peptide used for stimulations.

DETAILED DESCRIPTION OF THE INVENTION

Figure 1A:
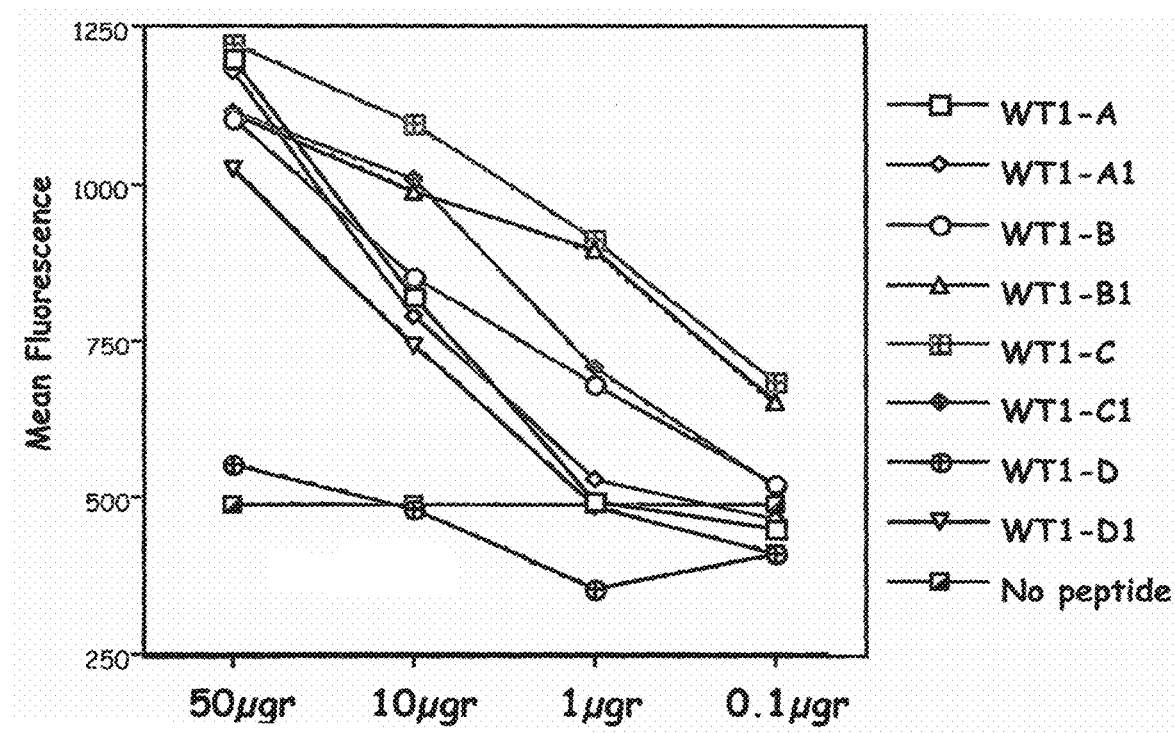
FIG. 1: T2 stabilization assay of native and synthetic WT-1 peptides to HLA A0201 cells (A) and HLA A0301 cells (B-E). Fluorescence index is ratio between median fluorescence with peptide tested: median fluorescence with no peptide. X axis: concentration per well of the peptide tested.
Figure 1B:
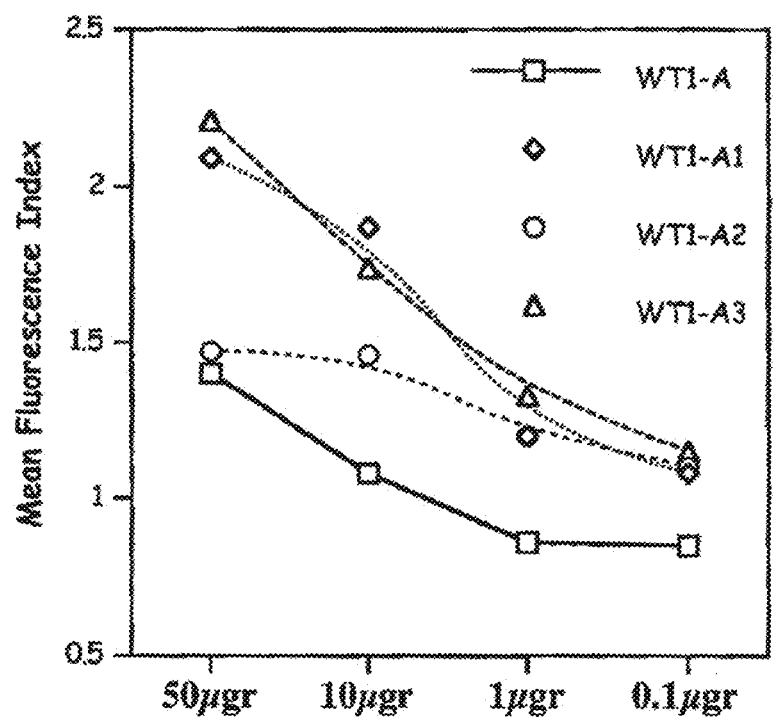
Figure 1C:
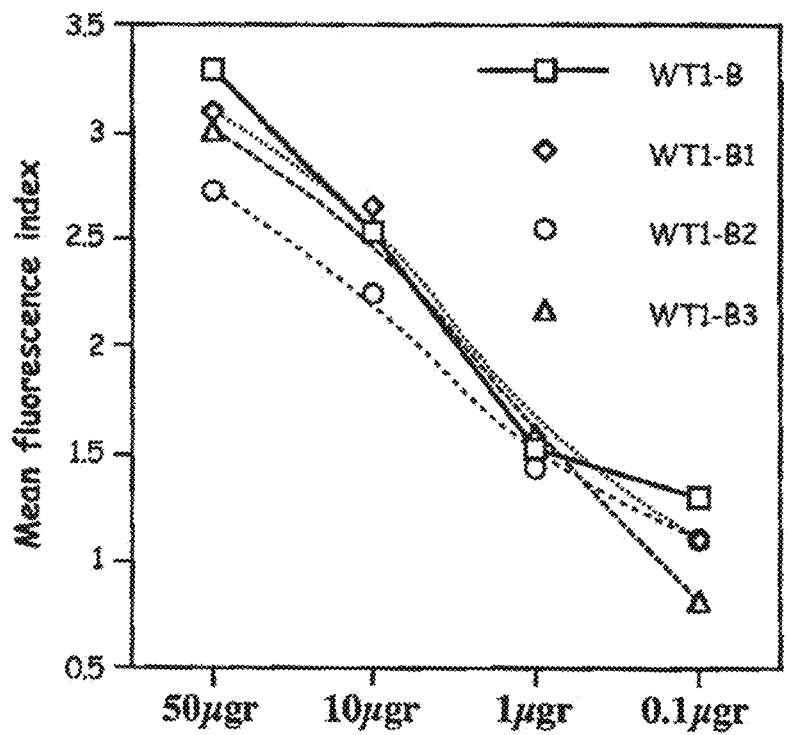
Figure 1D:
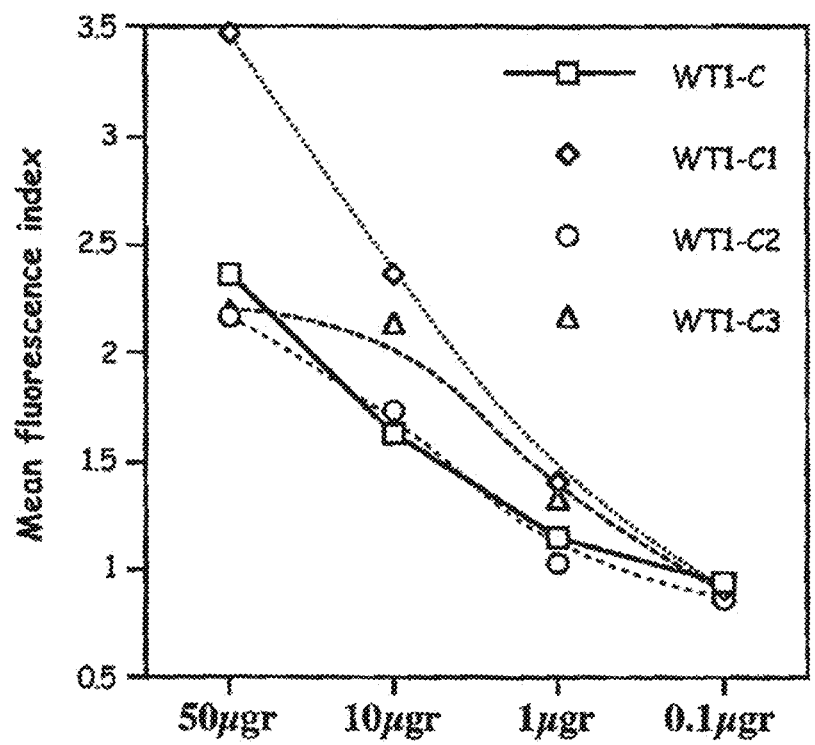
Figure 1E:
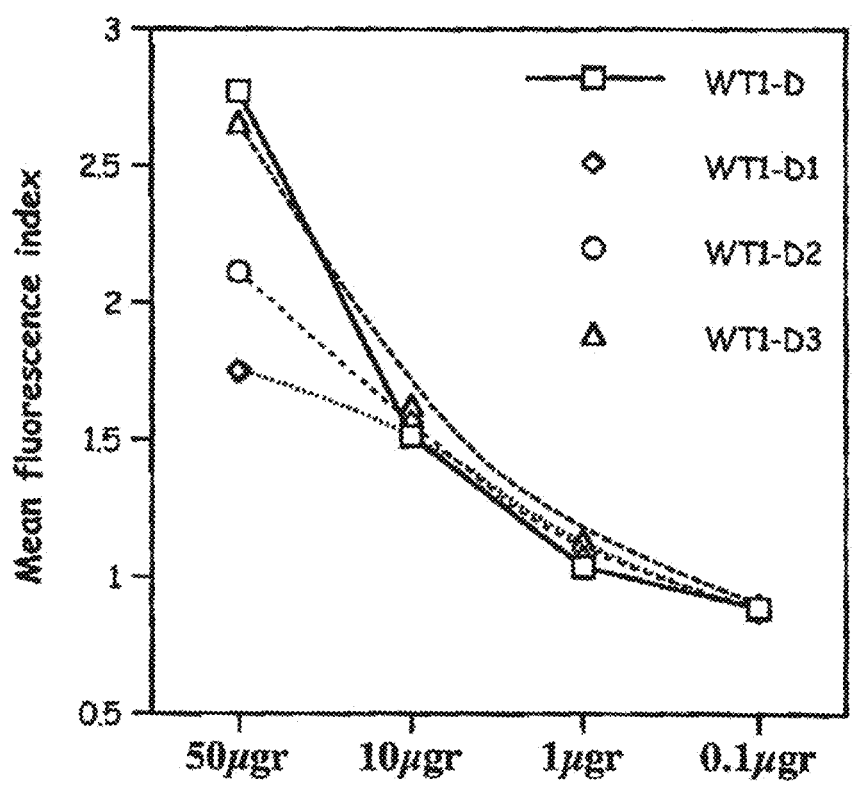

This invention provides immunogenic peptides, and compositions and vaccines comprising same, and methods of treating, reducing the incidence of, and inducing immune responses to a WT1-expressing cancer, comprising administering one or more of same.

In one embodiment, the present invention provides an isolated, mutated WT1 peptide, comprising: (a) a binding motif of a human leukocyte antigen (HLA) Class II molecule; and (b) a binding motif of an HLA class I molecule, having a point mutation in 1 or more anchor residues of the binding motif of an HLA class I molecule. In another embodiment, the peptide is 11 or more aa in length. Each possibility represents a separate embodiment of the present invention.

The "point mutation," in another embodiment, indicates that the fragment is mutated with respect to the native sequence of the protein, thus creating the HLA class I molecule binding motif. In another embodiment, the "point mutation" strengthens the binding capacity of an HLA class I molecule binding motif present in the native sequence. Each possibility represents a separate embodiment of the present invention.

In another embodiment, the point mutation is in 1-3 anchor residues of the HLA class I molecule binding motif. In another embodiment, the point mutation is in 1 anchor residue of the HLA class I molecule binding motif. In another embodiment, the point mutation is in 2 anchor residues of the HLA class I molecule binding motif. In another embodiment, the point mutation is in 1-2 anchor residues of the HLA class I molecule binding motif. In another embodiment, the point mutation is in 2-3 anchor residues of the HLA class I molecule binding motif. In another embodiment, the point mutation is in 1-4 anchor residues of the HLA class I molecule binding motif. Each possibility represents a separate embodiment of the present invention.

In another embodiment, a peptide of the present invention is 11-453 amino acids (AA) in length. In another embodiment, the length is 12-453 AA. In another embodiment, the length is 13-453 AA. In another embodiment, the length is 14-453 AA. In another embodiment, the length is 15-453 AA. In another embodiment, the length is 16-453 AA. In another embodiment, the length is 17-453 AA. In another embodiment, the length is 18-453 AA. In another embodiment, the length is 19-453 AA. In another embodiment, the length is 20-453 AA.

In another embodiment, the length is 11-449 AA. In another embodiment, the length is 12-449 AA. In another embodiment, the length is 13-449 AA. In another embodiment, the length is 14-449 AA. In another embodiment, the length is 15-449 AA. In another embodiment, the length is 16-449 AA. In another embodiment, the length is 17-449 AA. In another embodiment, the length is 18-449 AA. In another embodiment, the length is 19-449 AA. In another embodiment, the length is 20-449 AA.

In another embodiment, the length is 11-30 AA. In another embodiment, the length is 16-22 AA. In another embodiment, the length is 19 AA. In another embodiment, the peptide is 15-23 AA in length. In another embodiment, the length is 15-24 AA. In another embodiment, the length is 15-25 AA. In another embodiment, the length is 15-26 AA. In another embodiment, the length is 15-27 AA. In another embodiment, the length is 15-28 AA. In another embodiment, the length is 14-30 AA. In another embodiment, the length is 14-29 AA. In another embodiment, the length is 14-28 AA. In another embodiment, the length is 14-26 AA. In another embodiment, the length is 14-24 AA. In another embodiment, the length is 14-22 AA. In another embodiment, the length is 14-20 AA. In another embodiment, the length is 16-30 AA. In another embodiment, the length is 16-28 AA. In another embodiment, the length is 16-26 AA. In another embodiment, the length is 16-24 AA. In another embodiment, the length is 16-22 AA. In another embodiment, the length is 18-30 AA. In another embodiment, the length is 18-28 AA. In another embodiment, the length is 18-26 AA. In another embodiment, the length is 18-24 AA. In another embodiment, the length is 18-22 AA. In another embodiment, the length is 18-20 AA. In another embodiment, the length is 20-30 AA. In another embodiment, the length is 20-28 AA. In another embodiment, the length is 20-26 AA. In another embodiment, the length is 20-24 AA. In another embodiment, the length is 22-30 AA. In another embodiment, the length is 22-28 AA. In another embodiment, the length is 22-26 AA. In another embodiment, the length is 24-30 AA. In another embodiment, the length is 24-28 AA. In another embodiment, the length is 24-26 AA.

In another embodiment, a peptide of methods and compositions of the present invention is longer than the minimum length for binding to an HLA class II molecule, which is, in another embodiment, about 12 AA. In another embodiment, increasing the length of the HLA class II-binding peptide enables binding to more than one HLA class II molecule. In another embodiment, increasing the length enables binding to an HLA class II molecule whose binding motif is not known. In another embodiment, increasing the length enables binding to an HLA class I molecule. In another embodiment, the binding motif of the HLA class I molecule is known. In another embodiment, the binding motif of the HLA class I molecule is not known. Each possibility represents a separate embodiment of the present invention.

Each of the above peptide lengths represents a separate embodiment of the present invention.

HLA molecules, known in another embodiment as major histocompatibility complex (MHC) molecules, bind peptides and present them to immune cells. Thus, in another embodiment, the immunogenicity of a peptide is partially determined by its affinity for HLA molecules. HLA class I molecules interact with CD8 molecules, which are generally present on cytotoxic T lymphocytes (CTL). HLA class II molecules interact with CD4 molecules, which are generally present on helper T lymphocytes.

In another embodiment, a peptide of the present invention is immunogenic. In another embodiment, the term "immunogenic" refers to an ability to stimulate, elicit or participate in an immune response. In another embodiment, the immune response elicited is a cell-mediated immune response. In another embodiment, the immune response is a combination of cell-mediated and humoral responses.

In another embodiment, T cells that bind to the HLA molecule-peptide complex become activated and induced to proliferate and lyse cells expressing a protein comprising the peptide. T cells are typically initially activated by "professional" antigen presenting cells ("APC"; e.g. dendritic cells, monocytes, and macrophages), which present costimulatory molecules that encourage T cell activation rather than anergy or apoptosis. In another embodiment, the response is heteroclitic, as described herein, such that the CTL lyses a neoplastic cell expressing a protein which has an AA sequence homologous to a peptide of this invention, or a different peptide than that used to first stimulate the T cell.

In another embodiment, an encounter of a T cell with a peptide of this invention induces its differentiation into an effector and/or memory T cell. Subsequent encounters between the effector or memory T cell and the same peptide, or, in another embodiment, with a heteroclitic peptide of this invention, leads to a faster and more intense immune response. Such responses are gauged, in another embodiment, by measuring the degree of proliferation of the T cell population exposed to the peptide. In another embodiment, such responses are gauged by any of the methods enumerated hereinbelow.

In another embodiment, as described herein, the subject is exposed to a peptide, or a composition/cell population comprising a peptide of this invention, which differs from the native protein expressed, wherein subsequently a host immune response cross-reactive with the native protein/antigen develops.

In another embodiment, peptides, compositions, and vaccines of this invention stimulate an immune response that results in tumor cell lysis.

In another embodiment, the HLA class I molecule binding motif of a peptide of the present invention is contained within the HLA class II molecule binding motif of the peptide. In another embodiment, the HLA class I molecule binding motif overlaps with the HLA class II molecule binding motif. In another embodiment, the HLA class I molecule binding motif does not overlap with the HLA class II molecule binding motif. Each possibility represents a separate embodiment of the present invention.

The HLA class II molecule whose binding motif is contained in a peptide of the present invention is, in another embodiment, an HLA-DR molecule. In another embodiment, the HLA class II molecule is an HLA-DP molecule. In another embodiment, the HLA class II molecule is an HLA-DQ molecule.

In another embodiment, the HLA class II molecule is an HLA-DRB molecule. In another embodiment, the HLA class II molecule is DRB101. In another embodiment, the HLA class II molecule is DRB301. In another embodiment, the HLA class II molecule is DRB401. In another embodiment, the HLA class II molecule is DRB701. In another embodiment, the HLA class II molecule is DRB1101. In another embodiment, the HLA class II molecule is DRB1501. In another embodiment, the HLA class II molecule is any other HLA-DRB molecule known in the art. In another embodiment, the HLA class II molecule is an HLA-DRA molecule. In another embodiment, the HLA class II molecule is an HLA-DQA1 molecule. In another embodiment, the HLA class II molecule is an HLA-DQB1 molecule. In another embodiment, the HLA class II molecule is an HLA-DPA1 molecule. In another embodiment, the HLA class II molecule is an HLA-DPB1 molecule. In another embodiment, the HLA class II molecule is an HLA-DMA molecule. In another embodiment, the HLA class II molecule is an HLA-DMB molecule. In another embodiment, the HLA class II molecule is an HLA-DOA molecule. In another embodiment, the HLA class II molecule is an HLA-DOB molecule. In another embodiment, the HLA class II molecule is any other HLA class II-molecule known in the art.

In another embodiment, a peptide of the present invention binds to 2 distinct HLA class II molecules. In another embodiment, the peptide binds to three distinct HLA class II molecules. In another embodiment, the peptide binds to four distinct HLA class II molecules. In another embodiment, the peptide binds to five distinct HLA class II molecules. In another embodiment, the peptide binds to six distinct HLA class II molecules. In another embodiment, the peptide binds to more than six distinct HLA class II molecules.

In another embodiment, the HLA class II molecules that are bound by a peptide of the present invention are encoded by two or more distinct alleles at a given HLA class II locus. In another embodiment, the HLA class II molecules are encoded by three distinct alleles at a locus. In another embodiment, the HLA class II molecules are encoded by four distinct alleles at a locus. In another embodiment, the HLA class II molecules are encoded by five distinct alleles at a locus. In another embodiment, the HLA class II molecules are encoded by six distinct alleles at a locus. In another embodiment, the HLA class II molecules are encoded by more than six distinct alleles at a locus.

In another embodiment, the HLA class II molecules bound by the peptide are encoded by HLA class II genes at two distinct loci. In another embodiment, the HLA class II molecules are encoded by HLA class II genes at 2 or more distinct loci. In another embodiment, the HLA class II molecules are encoded by HLA class II genes at 3 distinct loci. In another embodiment, the HLA class II molecules are encoded by HLA class II genes at 3 or more distinct loci. In another embodiment, the HLA class II molecules are encoded by HLA class II genes at 4 distinct loci. In another embodiment, the HLA class II molecules are encoded by HLA class II genes at 4 or more distinct loci. In another embodiment, the HLA class II molecules are encoded by HLA class II genes at 5 distinct loci. In another embodiment, the HLA class II molecules are encoded by HLA class II genes at 5 or more distinct loci. In another embodiment, the HLA class II molecules are encoded by HLA class II genes at 6 distinct loci. In another embodiment, the HLA class II molecules are encoded by HLA class II genes at 6 or more distinct loci. In another embodiment, the HLA class II molecules are encoded by HLA class II genes at more than 6 distinct loci. Each possibility represents a separate embodiment of the present invention.

In another embodiment, a peptide of the present invention binds to 2 distinct HLA-DRB molecules. In another embodiment, the peptide binds to three distinct HLA-DRB molecules. In another embodiment, the peptide binds to four distinct HLA-DRB molecules. In another embodiment, the peptide binds to five distinct HLA-DRB molecules. In another embodiment, the peptide binds to six distinct HLA-DRB molecules. In another embodiment, the peptide binds to more than six distinct HLA-DRB molecules.

In another embodiment, the HLA class II molecules bound by the WT1 peptide are encoded by HLA class II genes at 2 distinct loci. In another embodiment, the HLA molecules bound are encoded by HLA class II genes at 2 or more distinct loci. In another embodiment, the HLA molecules bound are encoded by HLA class II genes at 3 distinct loci. In another embodiment, the HLA molecules bound are encoded by HLA class II genes at 3 or more distinct loci. In another embodiment, the HLA molecules bound are encoded by HLA class II genes at 4 distinct loci. In another embodiment, the HLA molecules bound are encoded by HLA class II genes at 4 or more distinct loci. In another embodiment, the HLA molecules bound are encoded by HLA class II genes at more than 4 distinct loci. In other embodiments, the loci are selected from HLA-DRB loci. In another embodiment, the HLA class II-binding peptide is an HLA-DRA binding peptide. In another embodiment, the peptide is an HLA-DQA1 binding peptide. In another embodiment, the peptide is an HLA-DQB1 binding peptide. In another embodiment, the peptide is an HLA-DPA1 binding peptide. In another embodiment, the peptide is an HLA-DPB1 binding peptide. In another embodiment, the peptide is an HLA-DMA binding peptide. In another embodiment, the peptide is an HLA-DMB binding peptide. In another embodiment, the peptide is an HLA-DOA binding peptide. In another embodiment, the peptide is an HLA-DOB binding peptide. In another embodiment, the peptide binds to any other HLA class II molecule known in the art. Each possibility represents a separate embodiment of the present invention.

In another embodiment, a peptide of the present invention binds to HLA-DRB molecules that are encoded by 2 distinct HLA-DRB alleles selected from DRB 101, DRB 301, DRB 401, DRB 701, DRB 1101, and DRB 1501. In another embodiment, the peptide binds to HLA-DRB molecules encoded by 3 distinct HLA-DRB alleles selected from DRB 101, DRB 301, DRB 401, DRB 701, DRB 1101, and DRB 1501. In another embodiment, the peptide binds to HLA-DRB molecules encoded by 4 distinct HLA-DRB alleles selected from DRB 101, DRB 301, DRB 401, DRB 701, DRB 1101, and DRB 1501. In another embodiment, the peptide binds to HLA-DRB molecules encoded by 5 distinct HLA-DRB alleles selected from DRB 101, DRB 301, DRB 401, DRB 701, DRB 1101, and DRB 1501. In another embodiment, the peptide binds to HLA-DRB molecules encoded by each of the following HLA-DRB alleles: DRB 101, DRB 301, DRB 401, DRB 701, DRB 1101, and DRB 1501. Each possibility represents a separate embodiment of the present invention.

Each of the above HLA class II molecule, types, classes, and combinations thereof represents a separate embodiment of the present invention.

The HLA class I molecule whose binding motif is contained in a peptide of the present invention is, in another embodiment, an HLA-A molecule. In another embodiment, the HLA class I molecule is an HLA-B molecule. In another embodiment, the HLA class I molecule is an HLA-C molecule. In another embodiment, the HLA class I molecule is an HLA-A0201 molecule. In another embodiment, the molecule is HLA A1. In another embodiment, the HLA class I molecule is HLA A2. In another embodiment, the HLA class I molecule is HLA A2.1. In another embodiment, the HLA class I molecule is HLA A3. In another embodiment, the HLA class I molecule is HLA A3.2. In another embodiment, the HLA class I molecule is HLA A11. In another embodiment, the HLA class I molecule is HLA A24. In another embodiment, the HLA class I molecule is HLA B7. In another embodiment, the HLA class I molecule is HLA B27. In another embodiment, the HLA class I molecule is HLA B8. Each possibility represents a separate embodiment of the present invention.

In another embodiment, the HLA class I molecule-binding WT1 peptide of methods and compositions of the present invention binds to a superfamily of HLA class I molecules. In another embodiment, the superfamily is the A2 superfamily. In another embodiment, the superfamily is the A3 superfamily. In another embodiment, the superfamily is the A24 superfamily. In another embodiment, the superfamily is the B7 superfamily. In another embodiment, the superfamily is the B27 superfamily. In another embodiment, the superfamily is the B44 superfamily. In another embodiment, the superfamily is the C1 superfamily. In another embodiment, the superfamily is the C4 superfamily. In another embodiment, the superfamily is any other superfamily known in the art. Each possibility represents a separate embodiment of the present invention.

In another embodiment, an HLA class I molecule binding motif of a peptide of the present invention exhibits an increased affinity for the HLA class I molecule, relative to the unmutated counterpart of the peptide. In another embodiment, the point mutation increases the affinity of the isolated, mutated WT1 peptide for the HLA class I molecule. In another embodiment, the increase in affinity is relative to the affinity (for the same HLA class I molecule) of the isolated, unmutated WT1 peptide wherefrom the isolated, mutated WT1 peptide was derived. Each possibility represents a separate embodiment of the present invention.

In another embodiment, an HLA class I molecule-binding WT peptide of methods and compositions of the present invention has a length of 9-13 AA. In another embodiment, the length is 8-13 AA. In another embodiment, the peptide has any of the lengths of a peptide of the present invention enumerated herein.

In another embodiment, the HLA class I molecule-binding WT peptide has length of 8 AA. In another embodiment, the peptide has length of 9 AA. In another embodiment, the peptide has length of 10 AA. As provided herein, native and heteroclitic peptides of 9-10 AA exhibited substantial binding to HLA class I molecules and ability to elicit cytokine secretion and cytolysis by CTL.

In another embodiment, an HLA class I molecule-binding WT1 peptide embedded within a WT1 peptide of the present invention has 1 of the above lengths. Each possibility represents a separate embodiment of the present invention.

In another embodiment, the HLA class I molecule that is bound by the HLA class I molecule-binding WT1 peptide is an HLA-A molecule. In another embodiment, the HLA class I-molecule is an HLA-A2 molecule. In another embodiment, the HLA class I-molecule is an HLA-A3 molecule. In another embodiment, the HLA class I-molecule is an HLA-A11 molecule. In another embodiment, the HLA class I-molecule is an HLA-B8 molecule. In another embodiment, the HLA class I-molecule is an HLA-0201 molecule. In another embodiment, the HLA class I-molecule binds any other HLA class I molecule known in the art. Each possibility represents a separate embodiment of the present invention.

In another embodiment, a peptide of the present invention retains ability to bind multiple HLA class II molecules, as exhibited by the isolated WT1 peptide wherefrom the peptide of the present invention was derived.

The WT1 molecule from which a peptide of the present invention is derived has, in another embodiment, the sequence:

```
MGSDVRDLNALLPAVPSLGGGGGCALPVSGAAQWAPVLDFAPPGASAYGS

LGGPAPPPAPPPPPPPPPHSFIKQEPSWGGAEPHEEQCLSAFTVHFSGQF

TGTAGACRYGPFGPPPPSQASSGQARMFPNAPYLPSCLESQPAIRNQGYS
```

-continued
```
TVTFDGTPSYGHTPSHHAAQFPNHSFKHEDPMGQQGSLGEQQYSVPPPVY

GCHTPTDSCTGSQALLLRTPYSSDNLYQMTSQLECMTWNQMNLGATLKGV

AAGSSSSVKWTEGQSNHSTGYESDNHTTPILCGAQYRIHTHGVFRGIQDV

RRVPGVAPTLVRSASETSEKRPFMCAYPGCNKRYFKLSHLQMHSRKHTGE

KPYQCDFKDCERRFSRSDQLKRHQRRHTGVKPFQCKTCQRKFSRSDHLKT

HTRTHTGKTSEKPFSCRWPSCQKKFARSDELVRHHNMHQRNMTKLQLAL
(GenBank Accession number AY245105; SEQ ID No: 46)
```

In another embodiment, the WT1 molecule has the sequence:

```
AAEASAERLQGRRSRGASGSEPQQMGSDVRDLNALLPAVPSLGGGGGCAL

PVSGAAQWAPVLDFAPPGASAYGSLGGPAPPPAPPPPPPPPHSFIKQEP

SWGGAEPHEEQCLSAFTVHFSGQFTGTAGACRYGPFGPPPPSQASSGQAR

MFPNAPYLPSCLESQPAIRNQGYSTVTFDGTPSYGHTPSHHAAQFPNHSF

KHEDPMGQQGSLGEQQYSVPPPVYGCHTPTDSCTGSQALLLRTPYSSDNL

YQMTSQLECMTWNQMNLGATLKGHSTGYESDNHTTPILCGAQYRIHTHGV

FRGIQDVRRVPGVAPTLVRSASETSEKRPFMCAYPGCNKRYFKLSHLQMH

SRKHTGEKPYQCDFKDCERRFSRSDQLKRHQRRHTGVKPFQCKTCQRKFS

RSDHLKTHTRTHTGEKPFSCRWPSCQKKFARSDELVRHHNMHQRNMTKLQ

LAL
(GenBank Accession number NM_000378; SEQ ID No:
47).
```

In another embodiment, the WT1 molecule has the sequence:

```
MQDPASTCVPEPASQHTLRSGPGCLQQPEQQGVRDPGGIWAKLGAAEASA

ERLQGRRSRGASGSEPQQMGSDVRDLNALLPAVPSLGGGGGCALPVSGAA

QWAPVLDFAPPGASAYGSLGGPAPPPAPPPPPPPPHSFIKQEPSWGGAE

PHEEQCLSAFTVHFSGQFTGTAGACRYGPFGPPPPSQASSGQARMFPNAP

YLPSCLESQPAIRNQGYSTVTFDGTPSYGHTPSHHAAQFPNHSFKHEDPM

GQQGSLGEQQYSVPPPVYGCHTPTDSCTGSQALLLRTPYSSDNLYQMTSQ

LECMTWNQMNLGATLKGVAAGSSSSVKWTEGQSNHSTGYESDNHTTPILC

GAQYRIHTHGVFRGIQDVRRVPGVAPTLVRSASETSEKRPFMCAYPGCNK

RYFKLSHLQMHSRKHTGEKPYQCDFKDCERRFSRSDQLKRHQRRHTGVKP

FQCKTCQRKFSRSDHLKTHTRTHTGEKPFSCRWPSCQKKFARSDELVRHH

NMHQRNMTKLQLAL
(GenBank Accession number NP_077742; SEQ ID No:
48).
```

In another embodiment, the WT1 molecule comprises the sequence:

```
                                      SEQ ID No: 43)
MGHHHHHHHHHHSSGHIEGRHMRRVPGVAPTLVRSASETSEKRPFMCAYP

GCNKRYFKLSHLQMHSRKHTGEKPYQCDFKDCERRFFRSDQLKRHQRRHT

GVKPFQCKTCQRKFSRSDHLKTHTRTHTGEKPFSCRWPSCQKKFARSDEL

VRHHNMHQRNMTKLQLAL.
```

In other embodiments, the WT1 protein comprises one of the sequences set forth in one of the following GenBank sequence entries: NM_024426, NM_024425, NM_024424, NM_000378, 595530, D13624, D12496, D12497, AH003034, or X77549. In other embodiments, the WT1 protein has one of the sequences set forth in one of the above GenBank sequence entries. In another embodiment, the WT1 protein is any WT1 protein known in the art. In another embodiment, the WT1 protein has any other WT1 sequence known in the art.

In another embodiment, a peptide of the present invention is derived from a fragment of a WT1 protein. In another embodiment, the process of derivation comprises introduction of the point mutation in the anchor residues of the HLA class I molecule binding motif. In another embodiment, the process of derivation consists of introduction of the point mutation in the anchor residues of the HLA class I molecule binding motif. In another embodiment, a peptide of the present invention differs from the corresponding fragment of a WT1 protein only by the point mutation in the HLA class I molecule binding motif anchor residue. In another embodiment, an HLA class I molecule binding motif of a peptide of the present invention differs from the corresponding WT1 sequence only by the point mutation in the anchor residue. Each possibility represents a separate embodiment of the present invention.

In another embodiment, the process of derivation of a peptide of the present invention further comprises one or more modifications of an amino acid (AA) to an AA analogue. In another embodiment, the process of derivation further comprises a modification of one or more peptide bond connecting two or more of the AA. In another embodiment, the AA analogue or peptide bond modification is one of the AA analogues or peptide bond modifications enumerated below. Each possibility represents a separate embodiment of the present invention.

The unmutated fragment of a WT1 protein wherefrom a peptide of the present invention (the "counterpart" in the wild-type sequence) is derived, in another embodiment, has the sequence SGQARMFPNAPYLPSCLES (SEQ ID No: 39). In another embodiment, the unmutated WT1 fragment has the sequence QARMFPNAPYLPSCL (SEQ ID No: 40). In another embodiment, the unmutated WT1 fragment has the sequence LVRHHNMHQRNMTKL (SEQ ID No: 1; Example 3). In another embodiment, the unmutated WT1 fragment has the sequence RSDELVRHHNMHQRNMTKL (SEQ ID No: 2; Example 3). In another embodiment, the unmutated WT1 fragment has the sequence NKRYFKLSHLQMHSR (SEQ ID No: 3; Example 3). In another embodiment, the unmutated WT1 fragment has the sequence PGCNKRYFKLSHLQMHSRKHTG (SEQ ID No: 4; Example 3). In another embodiment, the unmutated WT1 fragment is any other WT1 fragment that contains an HLA class II molecule binding motif. In another embodiment, the unmutated WT1 fragment is any other WT1 fragment that contains an HLA-DR molecule binding motif. In another embodiment, the unmutated WT1 fragment contains multiple HLA-DR molecule binding motifs. In another embodiment, the unmutated WT1 fragment is any other WT1 fragment that contains an HLA-DRB molecule binding motif. In another embodiment, the unmutated WT1 fragment contains multiple HLA-DRB molecule binding motifs. Methods for designing and deriving peptides of the present invention are described, for example, in Examples 3 and 5. Each possibility represents a separate embodiment of the present invention.

In another embodiment, a peptide of the present invention differs from it counterpart only in the point mutation that it contains. In another embodiment, a peptide of the present invention differs from it counterpart only in a mutation in HLA class I anchor residue(s). Each possibility represents a separate embodiment of the present invention.

In another embodiment, a peptide of the present invention retains the ability to bind an HLA class II molecule, as exhibited by the unmutated WT1 fragment wherefrom the peptide was derived. In another embodiment, a peptide of the present invention retains ability to bind multiple HLA class II molecules, as exhibited by the unmutated WT1 fragment. Each possibility represents a separate embodiment of the present invention.

The HLA class I molecule binding motif contained in a peptide of the present invention, in another embodiment, has the sequence YMFPNAPYL (SEQ ID No: 6). In another embodiment, the motif has the sequence YLGEQQYSV (SEQ ID NO: 8). In another embodiment, the motif has the sequence YLLPAVPSL (SEQ ID NO: 10). In another embodiment, the motif has the sequence YLGATLKGV (SEQ ID NO: 12). In another embodiment, the motif has the sequence YLNALLPAV (SEQ ID NO: 14). In another embodiment, the motif has the sequence GLRRGIQDV (SEQ ID NO: 16). In another embodiment, the motif has the sequence KLYFKLSHL (SEQ ID NO: 18). In another embodiment, the motif has the sequence ALLLRTPYV (SEQ ID NO: 20). In another embodiment, the motif has the sequence YMTWNQMNL (SEQ ID NO: 22). In another embodiment, the motif has the sequence NMYQRNMTK (SEQ ID NO: 24). In another embodiment, the motif has the sequence NMHQRVMTK (SEQ ID NO: 25). In another embodiment, the motif has the sequence NMYQRVMTK (SEQ ID NO: 26). In another embodiment, the motif has the sequence QMYLGATLK (SEQ ID NO: 28). In another embodiment, the motif has the sequence QMNLGVTLK (SEQ ID NO: 29). In another embodiment, the motif has the sequence QMYLGVTLK (SEQ ID NO: 30). In another embodiment, the motif has the sequence FMYAYPGCNK (SEQ ID NO: 32). In another embodiment, the motif has the sequence FMCAYPFCNK (SEQ ID NO: 33). In another embodiment, the motif has the sequence FMYAYPFCNK (SEQ ID NO: 34). In another embodiment, the motif has the sequence KLYHLQMHSR (SEQ ID NO: 36). In another embodiment, the motif has the sequence KLSHLQMHSK (SEQ ID NO: 37). In another embodiment, the motif has the sequence KLYHLQMHSK (SEQ ID NO: 38). In another embodiment, the motif is any other HLA class I motif known in the art. In another embodiment, the motif is any other HLA-A motif known in the art. Each possibility represents a separate embodiment of the present invention.

In another embodiment, the present invention provides an isolated peptide comprising the amino acid sequence SGQAYMFPNAPYLPSCLES (SEQ ID No: 41). In another embodiment, the AA sequence of the isolated peptide consists of SEQ ID No: 41. In another embodiment, the AA sequence of the isolated peptide consists of a fragment of SEQ ID No: 41. In another embodiment, the AA sequence of the isolated peptide comprises a fragment of SEQ ID No: 41. Each possibility represents a separate embodiment of the present invention.

In another embodiment, the present invention provides an isolated peptide comprising the amino acid sequence SGQARMFPNAPYLPSCLES (SEQ ID No: 39). In another embodiment, the AA sequence of the isolated peptide consists of SEQ ID No: 39. In another embodiment, the AA sequence of the isolated peptide consists of a fragment of SEQ ID No: 39. In another embodiment, the AA sequence of the isolated peptide comprises a fragment of SEQ ID No: 39. Each possibility represents a separate embodiment of the present invention.

In another embodiment, the present invention provides an isolated peptide comprising the AA sequence QAYMFPNAPYLPSCL (SEQ ID No: 42). In another embodiment, the AA sequence of the isolated peptide consists of SEQ ID No: 42. In another embodiment, the AA sequence of the isolated peptide consists of a fragment of SEQ ID No: 42. In another embodiment, the AA sequence of the isolated peptide comprises a fragment of SEQ ID No: 42. Each possibility represents a separate embodiment of the present invention.

In another embodiment, the present invention provides an isolated peptide comprising the AA sequence GATLKGVAAGSSSSVKWT (SEQ ID No: 44; "WT1 244" from Examples). In another embodiment, the AA sequence of the isolated peptide consists of SEQ ID No: 44. In another embodiment, the AA sequence of the isolated peptide consists of a fragment of SEQ ID No: 44. In another embodiment, the AA sequence of the isolated peptide comprises a fragment of SEQ ID No: 44. Each possibility represents a separate embodiment of the present invention.

"Peptide," in another embodiment of methods and compositions of the present invention, refers to a compound of subunit AA connected by peptide bonds. In another embodiment, the peptide comprises an AA analogue. In another embodiment, the peptide is a peptidomimetic. In another embodiment, a peptide of the present invention comprises one of the AA analogues enumerated below. The subunits are, in another embodiment, linked by peptide bonds. In another embodiment, the subunit is linked by another type of bond, e.g. ester, ether, etc. In another embodiment, a peptide of the present invention is one of the types of peptidomimetics enumerated below. Each possibility represents a separate embodiment of the present invention.

In another embodiment, a peptide of methods and compositions of the present invention binds with high affinity to the HLA class I molecule whose binding motif is contained therein. For example, peptides WT1-A1, B1, and C1 exhibited stable binding to HLA-A0201 (Example 1). In other embodiments, the HLA class I molecule is any HLA class I molecule enumerated herein. In another embodiment, the peptide binds to the HLA class I molecule with medium affinity. In another embodiment, the peptide binds to the HLA class I molecule with significant affinity. In another embodiment, the peptide binds to the HLA class I molecule with measurable affinity. In another embodiment, the peptide exhibits stable binding to the HLA class I molecule. Each possibility represents a separate embodiment of the present invention.

In another embodiment, a peptide of methods and compositions of the present invention binds with high affinity to the HLA class II molecule whose binding motif is contained therein. In other embodiments, the HLA class II molecule is any HLA class II molecule enumerated herein. In another embodiment, the peptide binds with high affinity to more than 1 HLA class II molecules. In another embodiment, the peptide binds to the HLA class II molecule with medium affinity. In another embodiment, the peptide binds with medium affinity to more than 1 HLA class II molecules. In another embodiment, the peptide binds to the HLA class II molecule with significant affinity. In another embodiment, the peptide binds with significant affinity to more than 1 HLA class II molecules. In another embodiment, the peptide binds to the HLA class II molecule with measurable affinity.

In another embodiment, the peptide binds with measurable affinity to more than 1 HLA class II molecules. In another embodiment, the peptide exhibits stable binding to the HLA class II molecule. In another embodiment, the peptide exhibits stable binding to more than 1 HLA class II molecules. Each possibility represents a separate embodiment of the present invention.

In another embodiment, a peptide of methods and compositions of the present invention binds to both an HLA class I molecule and an HLA class II molecule with significant affinity. In another embodiment, the peptide binds to both an HLA class I molecule and an HLA class II molecule with high affinity. In another embodiment, the peptide binds to both an HLA class I molecule and an HLA class II molecule with medium affinity. In another embodiment, the peptide binds to both an HLA class I molecule and an HLA class II molecule with measurable affinity. Each possibility represents a separate embodiment of the present invention.

"Fragment," in another embodiment, refers to a peptide of 11 or more AA in length. In another embodiment, a peptide fragment of the present invention is 16 or more AA long. In another embodiment, the fragment is 12 or more AA long. In another embodiment, the fragment is 13 or more AA. In another embodiment, the fragment is 14 or more AA. In another embodiment, the fragment is 15 or more AA. In another embodiment, the fragment is 17 or more AA. In another embodiment, the fragment is 18 or more AA. In another embodiment, the fragment is 19 or more AA. In another embodiment, the fragment is 22 or more AA. In another embodiment, the fragment is 8-12 AA. In another embodiment, the fragment is about 8-12 AA. In another embodiment, the fragment is 16-19 AA. In another embodiment, the fragment is about 16-19 AA. In another embodiment, the fragment 10-25 AA. In another embodiment, the fragment is about 10-25 AA. In another embodiment, the fragment has any other length. Each possibility represents a separate embodiment of the present invention.

In another embodiment, the present invention provides a composition comprising an isolated peptide of the invention in combination with at least 1 additional WT1 peptide. In certain embodiments, a composition comprising at least 2 different isolated peptides of the present invention is provided. In certain embodiments, a composition comprising at least 3 or at least 4 different isolated peptides of the present invention is provided. Each possibility represents a separate embodiment of the present invention. In certain embodiments, the composition of the present invention is a vaccine.

The additional WT1 peptide, in another embodiment, has the sequence QARMFPNAPYLPSCL (SEQ ID No: 40). In another embodiment, the additional WT1 peptide comprises the sequence QARMFPNAPYLPSCL. In another embodiment, the additional WT1 peptide comprises the sequence LVRHHNMHQRNMTKL (SEQ ID No: 1). In another embodiment, the additional WT1 peptide comprises the sequence LVRHHNMHQRNMTKL. In another embodiment, the additional WT1 peptide comprises the sequence RSDELVRHHNMHQRNMTKL (SEQ ID No: 2). In another embodiment, the additional WT1 peptide comprises the sequence RSDELVRHHNMHQRNMTKL. In another embodiment, the additional WT1 peptide comprises the sequence NKRYFKLSHLQMHSR (SEQ ID No: 3). In another embodiment, the additional WT1 peptide comprises the sequence NKRYFKLSHLQMHSR. In another embodiment, the additional WT1 peptide comprises the sequence PGCNKRYFKLSHLQMHSRKHTG (SEQ ID No: 4). In another embodiment, the additional WT1 peptide comprises the sequence PGCNKRYFKLSHLQMHSRKHTG. In another embodiment, the additional WT1 peptide has a sequence selected from the sequences set forth in SEQ ID No: 5-38. In another embodiment, the additional WT1 peptide is a heteroclitic peptide having a sequence selected from SEQ ID No: 5-38. In another embodiment, the additional WT1 peptide is a wild-type peptide having a sequence selected from SEQ ID No: 5-38. In another embodiment, the additional WT1 peptide is another heteroclitic WT1 peptide. In another embodiment, the additional WT1 peptide is another wild-type WT1 peptide.

In another embodiment, any other immunogenic WT1 peptide known in the art is utilized as an additional WT1 peptide. In another embodiment, any combination of immunogenic WT1 peptides known in the art is utilized.

Each additional WT1 peptide, and each combination thereof, represents a separate embodiment of the present invention.

In another embodiment, the additional WT1 peptide has a length of 8-22 AA. In another embodiment, the additional WT1 peptide has a length of 8-30 AA. In another embodiment, the additional WT1 peptide has a length of 11-30 AA. In another embodiment, the length is 16-22 AA. In another embodiment, the length is 19 AA. In another embodiment, the peptide is 15-23 AA in length. In another embodiment, the length is 15-24 AA. In another embodiment, the length is 15-25 AA. In another embodiment, the length is 15-26 AA. In another embodiment, the length is 15-27 AA. In another embodiment, the length is 15-28 AA. In another embodiment, the length is 14-30 AA. In another embodiment, the length is 14-29 AA. In another embodiment, the length is 14-28 AA. In another embodiment, the length is 14-26 AA. In another embodiment, the length is 14-24 AA. In another embodiment, the length is 14-22 AA. In another embodiment, the length is 14-20 AA. In another embodiment, the length is 16-30 AA. In another embodiment, the length is 16-28 AA. In another embodiment, the length is 16-26 AA. In another embodiment, the length is 16-24 AA. In another embodiment, the length is 16-22 AA. In another embodiment, the length is 18-30 AA. In another embodiment, the length is 18-28 AA. In another embodiment, the length is 18-26 AA. In another embodiment, the length is 18-24 AA. In another embodiment, the length is 18-22 AA. In another embodiment, the length is 18-20 AA. In another embodiment, the length is 20-30 AA. In another embodiment, the length is 20-28 AA. In another embodiment, the length is 20-26 AA. In another embodiment, the length is 20-24 AA. In another embodiment, the length is 22-30 AA. In another embodiment, the length is 22-28 AA. In another embodiment, the length is 22-26 AA. In another embodiment, the length is 24-30 AA. In another embodiment, the length is 24-28 AA. In another embodiment, the length is 24-26 AA.

In another embodiment, the additional WT1 peptide has any other length. Each possibility represents a separate embodiment of the present invention.

In another embodiment, a peptide of methods and compositions of the present invention binds an HLA class II molecule with significant affinity, while a peptide derived from the original peptide binds an HLA class I molecule with significant affinity.

In another embodiment, "affinity" refers to the concentration of peptide necessary for inhibiting binding of a standard peptide to the indicated MHC molecule by 50%. In another embodiment, "high affinity" refers to an affinity is such that a concentration of about 500 nanomolar (nM) or less of the peptide is required for 50% inhibition of binding of a standard peptide. In another embodiment, a concentration of about 400 nM or less of the peptide is required. In another embodiment, the binding affinity is 300 nM. In another embodiment, the binding affinity is 200 nM. In another embodiment, the binding affinity is 150 nM. In another embodiment, the binding affinity is 100 nM. In another embodiment, the binding affinity is 80 nM. In another embodiment, the binding affinity is 60 nM. In another embodiment, the binding affinity is 40 nM. In another embodiment, the binding affinity is 30 nM. In another embodiment, the binding affinity is 20 nM. In another embodiment, the binding affinity is 15 nM. In another embodiment, the binding affinity is 10 nM. In another embodiment, the binding affinity is 8 nM. In another embodiment, the binding affinity is 6 nM. In another embodiment, the binding affinity is 4 nM. In another embodiment, the binding affinity is 3 nM. In another embodiment, the binding affinity is 2 nM. In another embodiment, the binding affinity is 1.5 nM. In another embodiment, the binding affinity is 1 nM. In another embodiment, the binding affinity is 0.8 nM. In another embodiment, the binding affinity is 0.6 nM. In another embodiment, the binding affinity is 0.5 nM. In another embodiment, the binding affinity is 0.4 nM. In another embodiment, the binding affinity is 0.3 nM. In another embodiment, the binding affinity is less than 0.3 nM.

In another embodiment, "affinity" refers to a measure of binding strength to the MHC molecule. In another embodiment, affinity is measured using a method known in the art to measure competitive binding affinities. In another embodiment, affinity is measured using a method known in the art to measure relative binding affinities. In another embodiment, the method is a competitive binding assay. In another embodiment, the method is radioimmunoassay or RIA. In another embodiment, the method is BiaCore analyses. In another embodiment, the method is any other method known in the art. In another embodiment, the method yields an IC50 in relation to an IC50 of a reference peptide of known affinity.

Each type of affinity and method of measuring affinity represents a separate embodiment of the present invention.

In another embodiment, "high affinity" refers to an IC50 of 0.5-100 nM. In another embodiment, the IC50 is 1-100 nM. In another embodiment, the IC50 is 1.5-200 nM. In another embodiment, the IC50 is 2-100 nM. In another embodiment, the IC50 is 3-100 nM. In another embodiment, the IC50 is 4-100 nM. In another embodiment, the IC50 is 6-100 nM. In another embodiment, the IC50 is 10-100 nM. In another embodiment, the IC50 is 30-100 nM. In another embodiment, the IC50 is 3-80 nM. In another embodiment, the IC50 is 4-60 nM. In another embodiment, the IC50 is 5-50 nM. In another embodiment, the IC50 is 6-50 nM. In another embodiment, the IC50 is 8-50 nM. In another embodiment, the IC50 is 10-50 nM. In another embodiment, the IC50 is 20-50 nM. In another embodiment, the IC50 is 6-40 nM. In another embodiment, the IC50 is 8-30 nM. In another embodiment, the IC50 is 10-25 nM. In another embodiment, the IC50 is 15-25 nM. Each affinity and range of affinities represents a separate embodiment of the present invention.

In another embodiment, "medium affinity" refers to an IC50 of 100-500 nM. In another embodiment, the IC50 is 100-300 nM. In another embodiment, the IC50 is 100-200 nM. In another embodiment, the IC50 is 50-100 nM. In another embodiment, the IC50 is 50-80 nM. In another embodiment, the IC50 is 50-60 nM. Each affinity and range of affinities represents a separate embodiment of the present invention.

"Significant affinity" refers, in another embodiment, to sufficient affinity to mediate recognition of a target cell by a T cell carrying a T cell receptor (TCR) that recognizes the MHC molecule-peptide complex. In another embodiment, the term refers to sufficient affinity to mediate recognition of a cancer cell by a T cell carrying a TCR that recognizes the MHC molecule-peptide complex. In another embodiment, the term refers to sufficient affinity to mediate activation of a naive T cell by a dendritic cell presenting the peptide. In another embodiment, the term refers to sufficient affinity to mediate activation of a naive T cell by an APC presenting the peptide. In another embodiment, the term refers to sufficient affinity to mediate re-activation of a memory T cell by a dendritic cell presenting the peptide. In another embodiment, the term refers to sufficient affinity to mediate re-activation of a memory T cell by an APC presenting the peptide. In another embodiment, the term refers to sufficient affinity to mediate re-activation of a memory T cell by a somatic cell presenting the peptide. Each possibility represents a separate embodiment of the present invention.

"Measurable affinity" refers, in another embodiment, to sufficient affinity to be measurable by an immunological assay. In another embodiment, the immunological assay is any assay enumerated herein. Each possibility represents a separate embodiment of the present invention.

In another embodiment, a peptide of methods and compositions of the present invention binds to a superfamily of HLA molecules. Superfamilies of HLA molecules share very similar or identical binding motifs. In another embodiment, the superfamily is a HLA class I superfamily. In another embodiment, the superfamily is a HLA class II superfamily. Each possibility represents a separate embodiment of the present invention.

The terms "HLA-binding peptide," "HLA class I molecule-binding peptide," and "HLA class II molecule-binding peptide" refer, in another embodiment, to a peptide that binds an HLA molecule with measurable affinity. In another embodiment, the terms refer to a peptide that binds an HLA molecule with high affinity. In another embodiment, the terms refer to a peptide that binds an HLA molecule with sufficient affinity to activate a T cell precursor. In another embodiment, the terms refer to a peptide that binds an HLA molecule with sufficient affinity to mediate recognition by a T cell. The HLA molecule is, in other embodiments, any of the HLA molecules enumerated herein. Each possibility represents a separate embodiment of the present invention.

In another embodiment, a peptide of methods and compositions of the present invention is heteroclitic. "Heteroclitic" refers, in another embodiment, to a peptide that generates an immune response that recognizes the original peptide from which the heteroclitic peptide was derived (e.g. the peptide not containing the anchor residue mutations). In another embodiment, "original peptide" refers to a fragment of WT1 protein. For example, a peptide termed "WT1 122A1," having the sequence SGQAYMFPNAPYLPSCLES (SEQ ID No: 41), was generated from the wild-type WT1 peptide SGQARMFPNAPYLPSCLES (SEQ ID No: 39) by mutation of residue 5 to arginine (Example 5). The mutation introduced the CD8$^+$ heteroclitic WT1A1 peptide YMFPNAPYL (SEQ ID No: 6) into the WT 1 peptide. In another embodiment, "heteroclitic" refers to a peptide that generates an immune response that recognizes the original peptide from which the heteroclitic peptide was derived, wherein the immune response generated by vaccination with the heteroclitic peptide is greater than the immune response generated by vaccination with the original peptide. In another embodiment, a "heteroclitic" immune response refers to an immune response that recognizes the original peptide from which the improved peptide was derived (e.g. the peptide not containing the anchor residue mutations). In another embodiment, a "heteroclitic" immune response refers to an immune response that recognizes the original peptide from which the heteroclitic peptide was derived, wherein the immune response generated by vaccination with the heteroclitic peptide is greater than the immune response generated by vaccination with the original peptide. In another embodiment, the magnitude of the immune response generated by vaccination with the heteroclitic peptide is greater than the immune response substantially equal to the response to vaccination with the original peptide. In another embodiment, the magnitude of the immune response generated by vaccination with the heteroclitic peptide is greater than the immune response less than the response to vaccination with the original peptide. Each possibility represents a separate embodiment of the present invention.

In another embodiment, a heteroclitic peptide of the present invention induces an immune response that is increased at least 2-fold relative to the WT1 peptide from which the heteroclitic peptide was derived ("native peptide"). In another embodiment, the increase is 3-fold relative to the native peptide. In another embodiment, the increase is 5-fold relative to the native peptide. In another embodiment, the increase is 7-fold relative to the native peptide. In another embodiment, the increase is 10-fold relative to the native peptide. In another embodiment, the increase is 15-fold relative to the native peptide. In another embodiment, the increase is 20-fold relative to the native peptide. In another embodiment, the increase is 30-fold relative to the native peptide. In another embodiment, the increase is 50-fold relative to the native peptide. In another embodiment, the increase is 100-fold relative to the native peptide. In another embodiment, the increase is 150-fold relative to the native peptide. In another embodiment, the increase is 200-fold relative to the native peptide. In another embodiment, the increase is 300-fold relative to the native peptide. In another embodiment, the increase is 500-fold relative to the native peptide. In another embodiment, the increase is 1000-fold relative to the native peptide. In another embodiment, the increase is more than 1000-fold relative to the native peptide. Each possibility represents a separate embodiment of the present invention.

In another embodiment, a heteroclitic peptide of the present invention is an HLA class I heteroclitic peptide. In another embodiment, a heteroclitic peptide of the present invention is an HLA class II heteroclitic peptide. In another embodiment, a heteroclitic class II peptide of the present invention is mutated in a class II binding residue. In another embodiment, a heteroclitic class II peptide of the present invention is identified and tested in a manner analogous to identification and testing of HLA class I heteroclitic peptides, as exemplified herein. Each possibility represents a separate embodiment of the present invention.

"Anchor motifs" or "anchor residues" refers, in another embodiment, to one or a set of preferred residues at particular positions in an HLA-binding sequence. For example, residues at positions 1, 2, 3, 6, and 9 are used as anchor residues in the Examples herein. In another embodiment, the HLA-binding sequence is an HLA class II-binding sequence. In another embodiment, the HLA-binding sequence is an HLA class I-binding sequence. In another embodiment, the positions corresponding to the anchor motifs are those that play a significant role in binding the HLA molecule. In another embodiment, the anchor residue is a primary anchor motif. In another embodiment, the anchor residue is a secondary anchor motif. Each possibility represents a separate embodiment of the present invention.

In another embodiment, "anchor residues" are residues in positions 1, 3, 6, and 9 of the HLA class I binding motif. In another embodiment, the term refers to positions 1, 2, 6, and 9 of the HLA class I binding motif. In another embodiment, the term refers to positions 1, 6, and 9 of the HLA class I binding motif. In another embodiment, the term refers to positions 1, 2, and 9 of the HLA class I binding motif. In another embodiment, the term refers to positions 1, 3, and 9 of the HLA class I binding motif. In another embodiment, the term refers to positions 2 and 9 of the HLA class I binding motif. In another embodiment, the term refers to positions 6 and 9 of the HLA class I binding motif. Each possibility represents a separate embodiment of the present invention.

Methods for identifying MHC class II epitopes are well known in the art. In another embodiment, the MHC class II epitope is predicted using TEPITOPE (Meister G E, Roberts C G et al, Vaccine 1995 13: 581-91). In another embodiment, the MHC class II epitope is identified using EpiMatrix (De Groot A S, Jesdale B M et al, AIDS Res Hum Retroviruses 1997 13: 529-31). In another embodiment, the MHC class II epitope is identified using the Predict Method (Yu K, Petrovsky N et al, Mol Med. 2002 8: 137-48). In another embodiment, the MHC class II epitope is identified using the SYFPEITHI epitope prediction algorithm (Examples). SYFPEITHI is a database comprising more than 4500 peptide sequences known to bind class I and class II MHC molecules. SYFPEITHI provides a score based on the presence of certain amino acids in certain positions along the MHC-binding groove. Ideal amino acid anchors are valued at 10 points, unusual anchors are worth 6-8 points, auxiliary anchors are worth 4-6 points, preferred residues are worth 1-4 points; negative amino acid effect on the binding score between −1 and −3. The maximum score for HLA-A*0201 is 36.

In another embodiment, the MHC class II epitope is identified using Rankpep. Rankpep uses position specific scoring matrices (PSSMs) or profiles from sets of aligned peptides known to bind to a given MHC molecule as the predictor of MHC-peptide binding. Rankpep includes information on the score of the peptide and the % optimum or percentile score of the predicted peptide relative to that of a consensus sequence that yields the maximum score, with the selected profile. Rankpep includes a selection of 102 and 80 PSSMs for the prediction of peptide binding to MHC I and MHC II molecules, respectively. Several PSSMs for the prediction of peptide binders of different sizes are usually available for each MHC I molecule.

In another embodiment, the MHC class II epitope is identified using SVMHC (Donnes P, Elofsson A. Prediction of MHC class I binding peptides, using SVMHC. BMC Bioinformatics. 2002 Sep. 11; 3:25). In another embodiment, the MHC class II epitope is identified using any other method known in the art. The above methods are utilized, in another embodiment, to identify MHC class II binding will be perturbed by introduction of an MHC class I anchor residue mutation into the WT1 sequence. Each possibility represents a separate embodiment of the present invention.

Methods for identifying MHC class I epitopes are well known in the art. In another embodiment, the MHC class I epitope is predicted using BIMAS software (Example 1). The BIMAS score is based on the calculation of the theoretical half-life of the MHC-I/$\beta_2$-microglobulin/peptide complex, which is a measure of peptide-binding affinity. The program uses information about HLA-I peptides of 8-10 amino acids in length. The higher the binding affinity of a peptide to the MHC, the higher the likelihood that this peptide represents an epitope. The BIMAS algorithm assumes that each amino acid in the peptide contributes independently to binding to the class I molecule. Dominant anchor residues, which are critical for binding, have coefficients in the tables that are significantly higher than 1. Unfavorable amino acids have positive coefficients that are less than 1. If an amino acid is not known to make either a favorable or unfavorable contribution to binding, then is assigned the value 1. All the values assigned to the amino acids are multiplied and the resulting running score is multiplied by a constant to yield an estimate of half-time of dissociation.

In another embodiment, the MHC class I epitope is identified using SYFPEITHI. In another embodiment, the MHC class I epitope is identified using SVMHC (Donnes P, Elofsson A. Prediction of MHC class I binding peptides, using SVMHC. BMC Bioinformatics. 2002 Sep. 11; 3:25). In another embodiment, the MHC class I epitope is identified using NetMHC-2.0 (Sensitive quantitative predictions of peptide-MHC binding by a 'Query by Committee' artificial neural network approach. Buus S, Lauemoller S L, Worning P, Kesmir C, Frimurer T, Corbet S, Fomsgaard A, Hilden J, Holm A, Brunak S. Tissue Antigens., 62:378-84, 2003). In another embodiment, the MHC class I epitope is identified using any other method known in the art. The above methods are utilized, in another embodiment, to identify MHC class I epitopes that can be created by introduction of an anchor residue mutation into the WT1 sequence. Each possibility represents a separate embodiment of the present invention.

In another embodiment, the mutation that enhances MHC binding is in the residue at position 1 of the HLA class I binding motif. In another embodiment, the residue is changed to tyrosine. In another embodiment, the residue is changed to glycine. In another embodiment, the residue is changed to threonine. In another embodiment, the residue is changed to phenylalanine. In another embodiment, the residue is changed to any other residue known in the art. In another embodiment, a substitution in position 1 (e.g. to tyrosine) stabilizes the binding of the position 2 anchor residue.

In another embodiment, the mutation is in position 2 of the HLA class I binding motif. In another embodiment, the residue is changed to leucine. In another embodiment, the residue is changed to valine. In another embodiment, the residue is changed to isoleucine. In another embodiment, the residue is changed to methionine. In another embodiment, the residue is changed to any other residue known in the art.

In another embodiment, the mutation is in position 6 of the HLA class I binding motif. In another embodiment, the residue is changed to valine. In another embodiment, the residue is changed to cysteine. In another embodiment, the residue is changed to glutamine. In another embodiment, the residue is changed to histidine. In another embodiment, the residue is changed to any other residue known in the art.

In another embodiment, the mutation is in position 9 of the HLA class I binding motif. In another embodiment, the mutation changes the residue at the C-terminal position thereof. In another embodiment, the residue is changed to valine. In another embodiment, the residue is changed to threonine. In another embodiment, the residue is changed to isoleucine. In another embodiment, the residue is changed to leucine. In another embodiment, the residue is changed to alanine. In another embodiment, the residue is changed to cysteine. In another embodiment, the residue is changed to any other residue known in the art.

In another embodiment, the point mutation is in a primary anchor residue. In another embodiment, the HLA class I primary anchor residues are positions 2 and 9. In another embodiment, the point mutation is in a secondary anchor residue. In another embodiment, the HLA class I secondary anchor residues are positions 1 and 8. In another embodiment, the HLA class I secondary anchor residues are positions 1, 3, 6, 7, and 8. In another embodiment, the point mutation is in a position selected from positions 4, 5, and 8. Each possibility represents a separate embodiment of the present invention.

In another embodiment, the point mutation is in 1 or more residues in positions selected from positions 1, 2, 8, and 9 of the HLA class I binding motif. In another embodiment, the point mutation is in 1 or more residues in positions selected from positions 1, 3, 6, and 9. In another embodiment, the point mutation is in 1 or more residues in positions selected from positions 1, 2, 6, and 9. In another embodiment, the point mutation is in 1 or more residues in positions selected from positions 1, 6, and 9. In another embodiment, the point mutation is in 1 or more residues in positions selected from positions 1, 2, and 9. In another embodiment, the point mutation is in 1 or more residues in positions selected from positions 1, 3, and 9. In another embodiment, the point mutation is in 1 or more residues in positions selected from positions 2 and 9. In another embodiment, the point mutation is in 1 or more residues in positions selected from positions 6 and 9. Each possibility represents a separate embodiment of the present invention.

In another embodiment, the mutation is in the 4 position of the HLA class I binding motif. In another embodiment, the mutation is in the 5 position of the HLA class I binding motif. In another embodiment, the mutation is in the 7 position of the HLA class I binding motif. In another embodiment, the mutation is in the 8 position of the HLA class I binding motif. Each possibility represents a separate embodiment of the present invention.

Each of the above anchor residues and substitutions represents a separate embodiment of the present invention.

As provided herein, certain peptides of the present invention exhibited significant ability to stimulate both CD4$^+$ and CD8$^+$ T cells (Examples 6-10). Moreover, the peptides exhibited enhanced immuno-stimulating activity, relative to the native peptides from which they were derived. In addition, the peptides exhibited an ability to co-stimulate CD4$^+$ and CD8$^+$ immune responses to WT1 protein. In addition, the peptides exhibited an ability to stimulate an anti-WT1 immune response comprising both CD4$^+$ and CD8$^+$ T cells.

In another embodiment, the HLA class II binding site in a peptide of the present invention is created or improved by mutation of an HLA class II motif anchor residue. In another embodiment, the anchor residue that is modified is in the P1 position. In another embodiment, the anchor residue is at the P2 position. In another embodiment, the anchor residue is at the P6 position. In another embodiment, the anchor residue is at the P9 position. In another embodiment, the anchor residue is selected from the P1, P2, P6, and P9 positions. In another embodiment, the anchor residue is at the P3 position. In another embodiment, the anchor residue is at the P4 position. In another embodiment, the anchor residue is at the P5 position. In another embodiment, the anchor residue is at the P6 position. In another embodiment, the anchor residue is at the P8 position. In another embodiment, the anchor residue is at the P10 position. In another embodiment, the anchor residue is at the P11 position. In another embodiment, the anchor residue is at the P12 position. In another embodiment, the anchor residue is at the P13 position. In another embodiment, the anchor residue is at any other anchor residue of an HLA class II molecule that is known in the art. In another embodiment, residues other than P1, P2, P6, and P9 serve as secondary anchor residues; therefore, mutating them can improve HLA class II binding. In another embodiment, any combination of the above residues is mutated. Each possibility represents a separate embodiment of the present invention.

In another embodiment, the present invention provides a method of inducing an anti-mesothelioma immune response in a subject, the method comprising the step of contacting the subject with an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby inducing an anti-mesothelioma immune response in a subject.

In another embodiment, the present invention provides a method of treating a subject with a mesothelioma, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby treating a subject with a mesothelioma.

In another embodiment, the present invention provides a method of reducing an incidence of a mesothelioma, or its relapse, in a subject, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby reducing an incidence of a mesothelioma, or its relapse, in a subject.

"Fragment of a WT1 protein," in another embodiment, refers to any of the definitions of fragment found herein. Each definition represents a separate embodiment of the present invention.

As provided herein, mesothelioma cells express WT1 protein (Example 10). In addition, mesothelioma cells process and present peptides of the present invention or the corresponding native peptides (Example 6). Moreover, the presentation is robust enough to elicit anti-WT1 specific immune responses (Example 6). Thus, mesothelioma cells can be targeted by anti-WT1 immune therapy.

In another embodiment, a peptide of the present invention is homologous to a peptide enumerated in the Examples. The terms "homology," "homologous," etc, when in reference to any protein or peptide, refer, in another embodiment, to a percentage of AA residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in another embodiment, determined by computer algorithm for sequence alignment, by methods well described in the art. In other embodiments, computer algorithm analysis of nucleic acid sequence homology includes the utilization of any number of software packages available, such as, for example, the BLAST, DOMAIN, BEAUTY (BLAST Enhanced Alignment Utility), GEN-PEPT and TREMBL packages.

In another embodiment, "homology" refers to identity to a sequence selected from SEQ ID No: 1-4, 6, 39, 41, and 42 of greater than 70%. In another embodiment, "homology" refers to identity to a sequence selected from SEQ ID No: 1-4, 6, 39, 41, and 42 of greater than 72%. In another embodiment, "homology" refers to identity to one of SEQ ID No: 1-4, 6, 39, 41, and 42 of greater than 75%. In another embodiment, "homology" refers to identity to a sequence selected from SEQ ID No: 1-4, 6, 39, 41, and 42 of greater than 78%. In another embodiment, "homology" refers to identity to one of SEQ ID No: 1-4, 6, 39, 41, and 42 of greater than 80%. In another embodiment, "homology" refers to identity to one of SEQ ID No: 1-4, 6, 39, 41, and 42 of greater than 82%. In another embodiment, "homology" refers to identity to a sequence selected from SEQ ID No: 1-4, 6, 39, 41, and 42 of greater than 83%. In another embodiment, "homology" refers to identity to one of SEQ ID No: 1-4, 6, 39, 41, and 42 of greater than 85%. In another embodiment, "homology" refers to identity to one of SEQ ID No: 1-4, 6, 39, 41, and 42 of greater than 87%. In another embodiment, "homology" refers to identity to a sequence selected from SEQ ID No: 1-4, 6, 39, 41, and 42 of greater than 88%. In another embodiment, "homology" refers to identity to one of SEQ ID No: 1-4, 6, 39, 41, and 42 of greater than 90%. In another embodiment, "homology" refers to identity to one of SEQ ID No: 1-4, 6, 39, 41, and 42 of greater than 92%. In another embodiment, "homology" refers to identity to a sequence selected from SEQ ID No: 1-4, 6, 39, 41, and 42 of greater than 93%. In another embodiment, "homology" refers to identity to one of SEQ ID No: 1-4, 6, 39, 41, and 42 of greater than 95%. In another embodiment, "homology" refers to identity to a sequence selected from SEQ ID No: 1-4, 6, 39, 41, and 42 of greater than 96%. In another embodiment, "homology" refers to identity to one of SEQ ID No: 1-4, 6, 39, 41, and 42 of greater than 97%. In another embodiment, "homology" refers to identity to one of SEQ ID No: 1-4, 6, 39, 41, and 42 of greater than 98%. In another embodiment, "homology" refers to identity to one of SEQ ID No: 1-4, 6, 39, 41, and 42 of greater than 99%. In another embodiment, "homology" refers to identity to one of SEQ ID No: 1-4, 6, 39, 41, and 42 of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). In another embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Each of the above homologues and variants of peptides enumerated in the Examples represents a separate embodiment of the present invention.

In another embodiment, the present invention provides a composition comprising a peptide of this invention. In another embodiment, the composition further comprises a pharmaceutically acceptable carrier. In another embodiment, the composition further comprises an adjuvant. In another embodiment, the composition comprises 2 or more peptides of the present invention. In another embodiment, the composition further comprises any of the additives, compounds, or excipients set forth hereinbelow. In another embodiment, the adjuvant is QS21, Freund's complete or incomplete adjuvant, aluminum phosphate, aluminum hydroxide, BCG or alum. In other embodiments, the carrier is any carrier enumerated herein. In other embodiments, the adjuvant is any adjuvant enumerated herein. Each possibility represents a separate embodiment of the present invention.

In another embodiment, this invention provides a vaccine comprising a peptide of the present invention. In another embodiment, the vaccine further comprises a carrier. In another embodiment, the vaccine further comprises an adjuvant. In another embodiment, the vaccine further comprises a combination of a carrier and an adjuvant. In another embodiment, the vaccine further comprises an APC. In another embodiment, the vaccine further comprises a combination of an APC and a carrier or an adjuvant. In another embodiment, the vaccine is a cell-based composition. Each possibility represents a separate embodiment of the present invention.

In another embodiment, this invention provides an immunogenic composition comprising a peptide of the present invention. In another embodiment, the immunogenic composition further comprises a carrier. In another embodiment, the immunogenic composition further comprises an adjuvant. In another embodiment, the immunogenic composition further comprises a combination of a carrier and an adjuvant. Each possibility represents a separate embodiment of the present invention.

In another embodiment, the term "vaccine" refers to a material or composition that, when introduced into a subject, provides a prophylactic or therapeutic response for a particular disease, condition, or symptom of same. In another embodiment, this invention comprises peptide-based vaccines, wherein the peptide comprises any embodiment listed herein, optionally further including immunomodulating compounds such as cytokines, adjuvants, etc.

In other embodiments, a composition or vaccine of methods and compositions of the present invention further comprises an adjuvant. In another embodiment, the adjuvant is Montanide ISA 51. Montanide ISA 51 contains a natural metabolizable oil and a refined emulsifier. In another embodiment, the adjuvant is GM-CSF. In another embodiment, the adjuvant is KLH. Recombinant GM-CSF is a human protein grown, in another embodiment, in a yeast (S. cerevisiae) vector. GM-CSF promotes clonal expansion and differentiation of hematopoietic progenitor cells, APC, and dendritic cells and T cells.

In another embodiment, the adjuvant is a cytokine. In another embodiment, the adjuvant is a growth factor. In another embodiment, the adjuvant is a cell population. In another embodiment, the adjuvant is QS21. In another embodiment, the adjuvant is Freund's incomplete adjuvant. In another embodiment, the adjuvant is aluminum phosphate. In another embodiment, the adjuvant is aluminum hydroxide. In another embodiment, the adjuvant is BCG. In another embodiment, the adjuvant is alum. In another embodiment, the adjuvant is an interleukin. In another embodiment, the adjuvant is a chemokine. In another embodiment, the adjuvant is any other type of adjuvant known in the art. In another embodiment, the WT1 vaccine comprises two of the above adjuvants. In another embodiment, the WT1 vaccine comprises more than two of the above adjuvants. Each possibility represents a separate embodiment of the present invention.

In another embodiment, the present invention provides a cell comprising a peptide of the present invention. In another embodiment, the cell is an antigen-presenting cell. In another embodiment, the present invention provides a composition or vaccine comprising an antigen-presenting cell of the present invention.

In another embodiment, the present invention provides a nucleic acid molecule encoding a peptide of the present invention. In another embodiment, the present invention provides a composition or vaccine comprising a nucleic acid molecule of the present invention.

In another embodiment, the present invention provides a vector comprising a nucleic acid molecule of the present invention. In another embodiment, the present invention provides a composition or vaccine comprising a vector of the present invention.

In other embodiments, a composition or vaccine of the present invention can comprise any of the embodiments of WT1 peptides of the present invention and combinations thereof. Each possibility represents a separate embodiment of the present invention.

In another embodiment, the present invention provides a composition or vaccine comprising a peptide of the present invention and another WT peptide. In another embodiment, the composition or vaccine comprises a peptide of the present invention and 2 other WT peptides. In another embodiment, the composition comprises a peptide of the present invention and more than 2 other WT peptides.

In another embodiment, a composition of the present invention comprises two peptides that are derived from the same WT1 fragment, each containing a different HLA class I heteroclitic peptide. In another embodiment, the two HLA class I heteroclitic peptides contain mutations in different HLA class I molecule anchor residues. In another embodiment, the two HLA class I heteroclitic peptides contain different mutations in the same anchor residue(s). Each possibility represents a separate embodiment of the present invention.

In another embodiment, the peptides in a composition of the present invention bind to two distinct HLA class II molecules. In another embodiment, the peptides bind to three distinct HLA class II molecules. In another embodiment, the peptides bind to four distinct HLA class II molecules. In another embodiment, the peptides bind to five distinct HLA class II molecules. In another embodiment, the peptides bind to more than five distinct HLA class II molecules. In another embodiment, the peptides in the composition bind to the same HLA class II molecules.

In another embodiment, each of the peptides in a composition of the present invention binds to a set of HLA class II molecules. In another embodiment, each of the peptides binds to a distinct set of HLA class II molecules. In another embodiment, the peptides in the composition bind to the same set of HLA class II molecules. In another embodiment, two of the peptides bind to a distinct but overlapping set of HLA class II molecules. In another embodiment, two or more of the peptides bind to the same set of HLA class II molecules, while another of the peptides binds to a distinct set. In another embodiment, two or more of the peptides bind to an overlapping set of HLA class II molecules, while another of the peptides binds to a distinct set.

In another embodiment, the peptides in a composition of the present invention bind to two distinct HLA class I molecules. In another embodiment, the peptides bind to three distinct HLA class I molecules. In another embodiment, the peptides bind to four distinct HLA class I molecules. In another embodiment, the peptides bind to five distinct HLA class I molecules. In another embodiment, the peptides bind to more than five distinct HLA class I molecules. In another embodiment, the peptides in the composition bind to the same HLA class I molecules.

In another embodiment, each of the peptides in a composition of the present invention binds to a set of HLA class I molecules. In another embodiment, each of the peptides binds to a distinct set of HLA class I molecules. In another embodiment, the peptides in the composition bind to the same set of HLA class I molecules. In another embodiment, two of the peptides bind to a distinct but overlapping set of HLA class I molecules. In another embodiment, two or more of the peptides bind to the same set of HLA class I molecules, while another of the peptides binds to a distinct set. In another embodiment, two or more of the peptides bind to an overlapping set of HLA class I molecules, while another of the peptides binds to a distinct set.

In another embodiment, a "set of HLA class II molecules" or "set of HLA class I molecules" refers to the HLA molecules encoded by different alleles at a particular locus. In another embodiment, the term refers to HLA molecules with a particular binding specificity. In another embodiment, the term refers to HLA molecules with a particular peptide consensus sequence. In another embodiment, the term refers to a superfamily of HLA class II molecules. Each possibility represents a separate embodiment of the present invention.

Each of the above compositions and types of compositions represents a separate embodiment of the present invention.

Any embodiments described herein regarding peptides, compositions and_vaccines of this invention may be employed in any of the methods of this invention. Each combination of peptide, composition or vaccine with a method represents a separate embodiment thereof.

In another embodiment, the present invention provides a method of treating a subject with a WT1-expressing cancer, the method comprising administering to the subject a peptide of the present invention, thereby treating a subject with a WT1-expressing cancer. In another embodiment, the present invention provides a method of treating a subject with a WT1-expressing cancer, the method comprising administering to the subject a composition of the present invention, thereby treating a subject with a WT1-expressing cancer. In another embodiment, the present invention provides a method of treating a subject with a WT1-expressing cancer, the method comprising administering to the subject an immunogenic composition such as a vaccine of the present invention, thereby treating a subject with a WT1-expressing cancer.

In another embodiment, the present invention provides a method of suppressing or halting the progression of a WT1-expressing cancer in a subject, the method comprising administering to the subject a peptide of the present invention, thereby suppressing or halting the progression of a WT1-expressing cancer. In another embodiment, the present invention provides a method of suppressing or halting the progression of a WT1-expressing cancer in a subject, the method comprising administering to the subject a composition of the present invention, thereby suppressing or halting the progression of a WT1-expressing cancer. In another embodiment, the present invention provides a method of suppressing or halting the progression of a WT1-expressing cancer in a subject, the method comprising administering to the subject an immunogenic composition such as a vaccine of the present invention, thereby suppressing or halting the progression of a WT1-expressing cancer In another embodiment, the present invention provides a method of reducing the incidence of a WT1-expressing cancer in a subject, the method comprising administering to the subject a peptide of the present invention, thereby reducing the incidence of a WT1-expressing cancer in a subject. In another embodiment, the present invention provides a method of reducing the incidence of a WT1-expressing cancer in a subject, the method comprising administering to the subject a composition of the present invention, thereby reducing the incidence of a WT1-expressing cancer in a subject. In another embodiment, the present invention provides a method of reducing the incidence of a WT1-expressing cancer in a subject, the method comprising administering to the subject an immunogenic composition such as a vaccine of the present invention, thereby reducing the incidence of a WT1-expressing cancer in a subject.

In another embodiment, the present invention provides a method of reducing the incidence of relapse of a WT1-expressing cancer in a subject, the method comprising administering to the subject a peptide of the present invention, thereby reducing the incidence of relapse of a WT1-expressing cancer in a subject. In another embodiment, the present invention provides a method of reducing the incidence of relapse of a WT1-expressing cancer in a subject, the method comprising administering to the subject a composition of the present invention, thereby reducing the incidence of relapse of a WT1-expressing cancer in a subject. In another embodiment, the present invention provides a method of reducing the incidence of relapse of a WT1-expressing cancer in a subject, the method comprising administering to the subject an immunogenic composition such as a vaccine of the present invention, thereby reducing the incidence of relapse of a WT1-expressing cancer in a subject In another embodiment, the present invention provides a method of overcoming a T cell tolerance of a subject to a WT1-expressing cancer, the method comprising administering to the subject a peptide of the present invention, thereby overcoming a T cell tolerance to a WT1-expressing cancer. In another embodiment, the present invention provides a method of overcoming a T cell tolerance of a subject to a WT1-expressing cancer, the method comprising administering to the subject a composition of the present invention, thereby overcoming a T cell tolerance to a WT1-expressing cancer. In another embodiment, the present invention provides a method of overcoming a T cell tolerance of a subject to a WT1-expressing cancer, the method comprising administering to the subject an immunogenic composition such as a vaccine of the present invention, thereby overcoming a T cell tolerance to a WT1-expressing cancer In another embodiment, the present invention provides a method of treating a subject having a WT1-expressing cancer, comprising (a) inducing in a donor formation and proliferation of human cytotoxic T lymphocytes (CTL) that recognize a malignant cell of the cancer by a method of the present invention; and (b) infusing the human CTL into the subject, thereby treating a subject having a cancer.

In another embodiment, the present invention provides a method of treating a subject having a WT1-expressing cancer, comprising (a) inducing ex vivo formation and proliferation of human CTL that recognize a malignant cell of the cancer by a method of the present invention, wherein the human immune cells are obtained from a donor; and (b) infusing the human CTL into the subject, thereby treating a subject having a cancer.

Methods for ex vivo immunotherapy are well known in the art and are described, for example, in Davis I D et al (Blood dendritic cells generated with Flt3 ligand and CD40 ligand prime CD8+ T cells efficiently in cancer patients. J Immunother. 2006 Sep.-Oct.; 29(5):499-511) and Mitchell M S et al (The cytotoxic T cell response to peptide analogs of the HLA-A*0201-restricted MUC1 signal sequence epitope, M1.2. Cancer Immunol Immunother. 2006 Jul. 28). Each method represents a separate embodiment of the present invention.

In another embodiment, the present invention provides a method of inducing formation and proliferation of a WT1 protein-specific CTL, the method comprising contacting a lymphocyte population with an immunogenic composition such as a vaccine of the present invention, thereby inducing formation and proliferation of a WT1 protein-specific CTL. In another embodiment, the immunogenic composition comprises an antigen-presenting cell (APC) associated with a peptide of the present invention. In another embodiment, the present invention provides a method of inducing formation and proliferation of a WT1 protein-specific CTL, the method comprising contacting a lymphocyte population with a peptide or composition of the present invention, thereby inducing formation and proliferation of a WT1 protein-specific CTL. In another embodiment, the present invention provides a method of inducing formation and proliferation of a WT1 protein-specific CTL, the method comprising contacting a lymphocyte population with an vaccine of the present invention, thereby inducing formation and proliferation of a WT1 protein-specific CTL. In another embodiment, the CTL is specific for a WT1-expressing cell. In another embodiment, the target cell is a cell of a WT1-expressing cancer. Each possibility represents a separate embodiment of the present invention.

In another embodiment, the present invention provides a method of inducing in a subject formation and proliferation of a WT1 protein-specific CTL, the method comprising contacting the subject with an immunogenic composition such as a vaccine of the present invention, thereby inducing in a subject formation and proliferation of a WT1 protein-specific CTL. In another embodiment, the immunogenic composition comprises an APC associated with a mixture of peptides of the present invention. In another embodiment, the present invention provides a method of inducing in a subject formation and proliferation of a WT1 protein-specific CTL, the method comprising contacting the subject with a peptide or composition of the present invention, thereby inducing in a subject formation and proliferation of a WT1 protein-specific CTL. In another embodiment, the present invention provides a method of inducing in a subject formation and proliferation of a WT1 protein-specific CTL, the method comprising contacting the subject with an vaccine of the present invention, thereby inducing in a subject formation and proliferation of a WT1 protein-specific CTL. In another embodiment, the target cell is a cell of a WT1-expressing cancer. In another embodiment, the subject has the WT1-expressing cancer. In another embodiment, the CTL is specific for a WT1-expressing cell. In another embodiment, the subject is a lymphocyte donor (in another embodiment, a donor for a patient that has the WT1-expressing cancer.

In another embodiment, the present invention provides a method of inducing formation and proliferation of both (a) a WT1 protein-specific CD8+ lymphocyte; and (b) a CD4+ lymphocyte specific for the WT1 protein, the method comprising contacting a lymphocyte population with an immunogenic composition such as a vaccine of the present invention, thereby inducing formation and proliferation of both (a) a WT1 protein-specific CD8+ lymphocyte; and (b) a CD4+ lymphocyte specific for the WT1 protein. In another embodiment, the immunogenic composition comprises an APC associated with a mixture of peptides of the present invention. In another embodiment, the present invention provides a method of inducing formation and proliferation of both (a) a WT1 protein-specific CD8+ lymphocyte; and (b) a CD4+ lymphocyte specific for the WT1 protein, the method comprising contacting a lymphocyte population with a peptide or composition of the present invention, thereby inducing formation and proliferation of both (a) a WT1 protein-specific CD8+ lymphocyte; and (b) a CD4+ lymphocyte specific for the WT1 protein. In another embodiment, the present invention provides a method of inducing formation and proliferation of both (a) a WT1 protein-specific CD8+ lymphocyte; and (b) a CD4+ lymphocyte specific for the WT1 protein, the method comprising contacting a lymphocyte population with a vaccine of the present invention, thereby inducing formation and proliferation of both (a) a WT1 protein-specific CD8+ lymphocyte; and (b) a CD4+ lymphocyte specific for the WT1 protein. In another embodiment, the CTL is specific for a WT1-expressing cell. In another embodiment, the target cell is a cell of a WT1-expressing cancer.

In another embodiment, the present invention provides a method of inducing in a subject formation and proliferation of both (a) a WT1 protein-specific CD8+ lymphocyte; and (b) a CD4+ lymphocyte specific for the WT1 protein, the method comprising contacting the subject with an immunogenic composition such as a vaccine of the present invention, thereby inducing in a subject formation and proliferation of both (a) a WT1 protein-specific CD8+ lymphocyte; and (b) a CD4+ lymphocyte specific for the WT1 protein. In another embodiment, the immunogenic composition comprises an APC associated with a mixture of peptides of the present invention. In another embodiment, the present invention provides a method of inducing in a subject formation and proliferation of both (a) a WT1 protein-specific CD8+ lymphocyte; and (b) a CD4+ lymphocyte specific for the WT1 protein, the method comprising contacting the subject with a peptide or composition of the present invention, thereby inducing in a subject formation and proliferation of both (a) a WT1 protein-specific CD8+ lymphocyte; and (b) a CD4+ lymphocyte specific for the WT1 protein. In another embodiment, the present invention provides a method of inducing in a subject formation and proliferation of both (a) a WT1 protein-specific CD8+ lymphocyte; and (b) a CD4+ lymphocyte specific for the WT1 protein, the method comprising contacting the subject with a vaccine of the present invention, thereby inducing in a subject formation and proliferation of both (a) a WT1 protein-specific CD8+ lymphocyte; and (b) a CD4+ lymphocyte specific for the WT1 protein. In another embodiment, the target cell is a cell of a WT1-expressing cancer. In another embodiment, the subject has the WT1-expressing cancer. In another embodiment, the CTL is specific for a WT1-expressing cell. In another embodiment, the subject is a lymphocyte donor (in another embodiment, a donor for a patient that has the WT1-expressing cancer.

In another embodiment, this invention provides a method of generating a heteroclitic immune response in a subject, wherein the heteroclitic immune response is directed against a WT1-expressing cancer, the method comprising administering to the subject a peptide or composition of the present invention, thereby generating a heteroclitic immune response. In another embodiment, this invention provides a method of generating a heteroclitic immune response in a subject, wherein the heteroclitic immune response is directed against a WT1-expressing cancer, the method comprising administering to the subject an immunogenic composition such as a vaccine of the present invention, thereby generating a heteroclitic immune response. In another embodiment, this invention provides a method of generating a heteroclitic immune response in a subject, wherein the heteroclitic immune response is directed against a WT1-expressing cancer, the method comprising administering to the subject a vaccine of the present invention, thereby generating a heteroclitic immune response.

Each method represents a separate embodiment of the present invention.

In another embodiment, a target cell of an immune response elicited by a method of the present invention presents the peptide of the present invention, or a corresponding WT1 fragment, on an HLA class I molecule. In another embodiment, the HLA molecule is an HLA class I molecule. In another embodiment, the HLA molecule is an HLA class II molecule. In another embodiment, the peptide or a fragment thereof is presented on both an HLA class I molecule and an HLA class II molecule. In other embodiments, the HLA class I molecule is any HLA class I subtype or HLA class I molecule known in the art. In other embodiments, the HLA class I molecule is any HLA class I subtype or HLA class I molecule enumerated herein. In other embodiments, the HLA class II molecule is any HLA class II subtype or HLA class II molecule known in the art. In other embodiments, the HLA class II molecule is any HLA class II subtype or HLA class II molecule enumerated herein. In another embodiment, the immune response against the peptide or fragment is a heteroclitic immune response. Each possibility represents a separate embodiment of the present invention.

In another embodiment, the WT1-expressing cancer is an acute myelogenous leukemia (AML). In another embodiment, the WT1-expressing cancer is associated with a myelodysplastic syndrome (MDS). In another embodiment, the WT1-expressing cancer is an MDS. In another embodiment, the WT1-expressing cancer is a non-small cell lung cancer (NSCLC). In another embodiment, the WT1-expressing cancer is a Wilms' tumor. In another embodiment, the WT1-expressing cancer is a leukemia. In another embodiment, the WT1-expressing cancer is a hematological cancer. In another embodiment, the WT1-expressing cancer is a lymphoma. In another embodiment, the WT1-expressing cancer is a desmoplastic small round cell tumor. In another embodiment, the WT1-expressing cancer is a mesothelioma. In another embodiment, the WT1-expressing cancer is a malignant mesothelioma. In another embodiment, the WT1-expressing cancer is a gastric cancer. In another embodiment, the WT1-expressing cancer is a colon cancer. In another embodiment, the WT1-expressing cancer is a lung cancer. In another embodiment, the WT1-expressing cancer is a breast cancer. In another embodiment, the WT1-expressing cancer is a germ cell tumor. In another embodiment, the WT1-expressing cancer is an ovarian cancer. In another embodiment, the WT1-expressing cancer is a uterine cancer. In another embodiment, the WT1-expressing cancer is a thyroid cancer. In another embodiment, the WT1-expressing cancer is a hepatocellular carcinoma. In another embodiment, the WT1-expressing cancer is a thyroid cancer. In another embodiment, the WT1-expressing cancer is a liver cancer. In another embodiment, the WT1-expressing cancer is a renal cancer. In another embodiment, the WT1-expressing cancer is a kaposi's sarcoma. In another embodiment, the WT1-expressing cancer is a sarcoma. In another embodiment, the WT1-expressing cancer is any other carcinoma or sarcoma.

In another embodiment, the WT1-expressing cancer is a solid tumor. In another embodiment, the solid tumor is associated with a WT1-expressing cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

In another embodiment, a cancer or tumor treated by a method of the present invention is suspected to express WT1. In another embodiment, WT1 expression has not been verified by testing of the actual tumor sample. In another embodiment, the cancer or tumor is of a type known to express WT1 in many cases. In another embodiment, the type expresses WT1 in the majority of cases.

Each type of WT1-expressing cancer or tumor, and cancer or tumor suspected to express WT1, represents a separate embodiment of the present invention.

In another embodiment, multiple peptides of this invention are used to stimulate an immune response in methods of the present invention.

As provided herein, heteroclitic peptides that elicit antigen-specific $CD8^+$ T cell responses can be created using methods of the present invention (Examples 1-2). As provided in Examples 3-4, WT1 peptides that elicit $CD4^+$ T cell responses to multiple HLA class II molecules can be identified. $CD4^+$ T cells recognize peptides bound to the HLA class II molecule on APC. In another embodiment, antigen-specific $CD4^+$ T cell responses assist in induction and maintenance of $CD8^+$ cytotoxic T cell (CTL) responses.

In another embodiment, peptides of the present invention exhibit an enhanced ability to elicit CTL responses, due to their ability to bind both HLA class I and HLA class II molecules. In another embodiment, vaccines of the present invention have the advantage of activating or eliciting both $CD4^+$ and $CD8^+$ T cells that recognize WT1 antigens. In another embodiment, activation or eliciting both $CD4^+$ and $CD8^+$ T cells provides a synergistic anti-WT1 immune response, relative to activation of either population alone. In another embodiment, the enhanced immunogenicity of peptides of the present invention is exhibited in individuals of multiple HLA class II subtypes, due to the ability of peptides of the present invention to bind multiple HLA class II subtypes. Each possibility represents a separate embodiment of the present invention.

In another embodiment, activated $CD4^+$ cells enhance immunity by licensing dendritic cells, thereby sustaining the activation and survival of the cytotoxic T cells. In another embodiment, activated CD4⁺ T cells induce tumor cell death by direct contact with the tumor cell or by activation of the apoptosis pathway. Mesothelioma tumor cells, for example, are able to process and present antigens in the context of HLA class I and class II molecules.

The methods disclosed herein will be understood by those in the art to enable design of other WT1-derived peptides that are capable of binding both HLA class I and HLA class II molecules. The methods further enable design of immunogenic compositions and vaccines combining WT1-derived peptides of the present invention. Each possibility represents a separate embodiment of the present invention.

In another embodiment, peptides, vaccines, and/or immunogenic compositions of the present invention have the advantage of activating or eliciting WT1-specific CD4⁺ T cells containing multiple different HLA class II alleles. In another embodiment, the vaccines have the advantage of activating or eliciting WT1-specific CD4⁺ T cells in a substantial proportion of the population. In another embodiment, the peptides activate WT1-specific CD4⁺ T cells in 10% of the population. In another embodiment, the peptides activate WT1-specific CD4⁺ T cells in 15% of the population. In another embodiment, the peptides activate WT1-specific CD4⁺ T cells in 20% of the population. In another embodiment, the peptides activate WT1-specific CD4⁺ T cells in 25% of the population. In another embodiment, the peptides activate WT1-specific CD4⁺ T cells in 30% of the population. In another embodiment, the peptides activate WT1-specific CD4⁺ T cells in 35% of the population. In another embodiment, the peptides activate WT1-specific CD4⁺ T cells in 40% of the population. In another embodiment, the peptides activate WT1-specific CD4⁺ T cells in 45% of the population. In another embodiment, the peptides activate WT1-specific CD4⁺ T cells in 50% of the population. In another embodiment, the peptides activate WT1-specific CD4⁺ T cells in 55% of the population. In another embodiment, the peptides activate WT1-specific CD4⁺ T cells in 60% of the population. In another embodiment, the peptides activate WT1-specific CD4⁺ T cells in 70% of the population. In another embodiment, the peptides activate WT1-specific CD4⁺ T cells in 75% of the population. In another embodiment, the peptides activate WT1-specific CD4⁺ T cells in 80% of the population. In another embodiment, the peptides activate WT1-specific CD4⁺ T cells in 85% of the population. In another embodiment, the peptides activate WT1-specific CD4⁺ T cells in 90% of the population. In another embodiment, the peptides activate WT1-specific CD4⁺ T cells in 95% of the population. In another embodiment, the peptides activate WT1-specific CD4⁺ T cells in greater than 95% of the population. In another embodiment, the vaccines activate or elicit WT1-specific CD4⁺ T cells in a substantial proportion of a particular population (e.g. American Caucasians). Each possibility represents a separate embodiment of the present invention.

In another embodiment, peptides, vaccines, and/or immunogenic compositions of the present invention elicit enhanced WT1-specific CTL responses in individuals carrying both the HLA class I molecule and the HLA class II molecule whose binding motifs are present in the peptide. In another embodiment, due to the binding of multiple HLA class I molecules and/or multiple HLA class II molecules, the peptides elicit enhanced WT1-specific CTL responses in a substantial proportion of the population. In another embodiment, the peptides elicit enhanced WT1-specific CTL responses in 10% of the population. In another embodiment, the peptides elicit enhanced WT1-specific CTL responses in 15% of the population. In another embodiment, the peptides elicit enhanced WT1-specific CTL responses in 20% of the population. In another embodiment, the peptides elicit enhanced WT1-specific CTL responses in 25% of the population. In another embodiment, the peptides elicit enhanced WT1-specific CTL responses in 30% of the population. In another embodiment, the peptides elicit enhanced WT1-specific CTL responses in 35% of the population. In another embodiment, the peptides elicit enhanced WT1-specific CTL responses in 40% of the population. In another embodiment, the peptides elicit enhanced WT1-specific CTL responses in 45% of the population. In another embodiment, the peptides elicit enhanced WT1-specific CTL responses in 50% of the population. In another embodiment, the peptides elicit enhanced WT1-specific CTL responses in 55% of the population. In another embodiment, the peptides elicit enhanced WT1-specific CTL responses in 60% of the population. In another embodiment, the peptides elicit enhanced WT1-specific CTL responses in 70% of the population. In another embodiment, the peptides elicit enhanced WT1-specific CTL responses in 75% of the population. In another embodiment, the peptides elicit enhanced WT1-specific CTL responses in 80% of the population. In another embodiment, the peptides elicit enhanced WT1-specific CTL responses in 85% of the population. In another embodiment, the peptides elicit enhanced WT1-specific CTL responses in 90% of the population. In another embodiment, the peptides elicit enhanced WT1-specific CTL responses in 95% of the population. In another embodiment, the peptides elicit enhanced WT1-specific CTL responses in greater than 95% of the population. In another embodiment, the vaccines activate or elicit WT1-specific CD4⁺ T cells in a substantial proportion of a particular population (e.g. American Caucasians). Each possibility represents a separate embodiment of the present invention.

In another embodiment, methods of the present invention provide for an improvement in an immune response that has already been mounted by a subject. In another embodiment, methods of the present invention comprise administering the peptide, composition, or vaccine 2 or more times. In another embodiment, the peptides are varied in their composition, concentration, or a combination thereof. In another embodiment, the peptides provide for the initiation of an immune response against an antigen of interest in a subject in which an immune response against the antigen of interest has not already been initiated. In another embodiment, the CTL that are induced proliferate in response to presentation of the peptide on the APC or cancer cell. In other embodiments, reference to modulation of the immune response involves, either or both the humoral and cell-mediated arms of the immune system, which is accompanied by the presence of Th2 and Th1 T helper cells, respectively, or in another embodiment, each arm individually.

In other embodiments, the methods affecting the growth of a tumor result in (1) the direct inhibition of tumor cell division, or (2) immune cell mediated tumor cell lysis, or both, which leads to a suppression in the net expansion of tumor cells. Each possibility represents a separate embodiment of the present invention.

Inhibition of tumor growth by either of these two mechanisms can be readily determined by one of ordinary skill in the art based upon a number of well known methods. In another embodiment, tumor inhibition is determined by measuring the actual tumor size over a period of time. In another embodiment, tumor inhibition can be determined by estimating the size of a tumor (over a period of time) utilizing methods well known to those of skill in the art. More specifically, a variety of radiologic imaging methods (e.g., single photon and positron emission computerized tomography; see generally, "Nuclear Medicine in Clinical Oncology," Winkler, C. (ed.) Springer-Verlag, New York, 1986), can be utilized to estimate tumor size. Such methods can also utilize a variety of imaging agents, including for example, conventional imaging agents (e.g., Gallium-67 citrate), as well as specialized reagents for metabolite imaging, receptor imaging, or immunologic imaging (e.g., radiolabeled monoclonal antibody specific tumor markers). In addition, non-radioactive methods such as ultrasound (see, "Ultrasonic Differential Diagnosis of Tumors", Kossoff and Fukuda, (eds.), Igaku-Shoin, N.Y., 1984), can also be utilized to estimate the size of a tumor.

In addition to the in vivo methods for determining tumor inhibition discussed above, a variety of in vitro methods can be utilized in order to determine in vivo tumor inhibition. Representative examples include lymphocyte mediated antitumor cytolytic activity determined for example, by a $^{51}$Cr release assay (Examples), tumor dependent lymphocyte proliferation (Ioannides, et al., J. Immunol. 146(5):1700-1707, 1991), in vitro generation of tumor specific antibodies (Herlyn, et al., J. Immunol. Meth. 73:157-167, 1984), cell (e.g., CTL, helper T-cell) or humoral (e.g., antibody) mediated inhibition of cell growth in vitro (Gazit, et al., Cancer Immunol Immunother 35:135-144, 1992), and, for any of these assays, determination of cell precursor frequency (Vose, Int. J. Cancer 30:135-142 (1982), and others.

In another embodiment, methods of suppressing tumor growth indicate a growth state that is curtailed compared to growth without contact with, or exposure to a peptide of this invention. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth refers, in other embodiments, to slowing, delaying, or stopping tumor growth, or to tumor shrinkage. Each possibility represents a separate embodiment of the present invention.

In another embodiment of methods and compositions of the present invention, WT1 expression is measured. In another embodiment, WT1 transcript expression is measured. In another embodiment, WT1 protein levels in the tumor are measured. Each possibility represents a separate embodiment of the present invention.

Methods of determining the presence and magnitude of an immune response are well known in the art. In another embodiment, lymphocyte proliferation assays, wherein T cell uptake of a radioactive substance, e.g. $^3$H-thymidine is measured as a function of cell proliferation. In other embodiments, detection of T cell proliferation is accomplished by measuring increases in interleukin-2 (IL-2) production, Ca$^{2+}$ flux, or dye uptake, such as 3-(4,5-dimethylthiazol-2-yl)-2, 5-diphenyl-tetrazolium. Each possibility represents a separate embodiment of the present invention.

In another embodiment, CTL stimulation is determined by means known to those skilled in the art, including detection of cell proliferation, cytokine production and others. Analysis of the types and quantities of cytokines secreted by T cells upon contacting ligand-pulsed targets can be a measure of functional activity. Cytokines can be measured by ELISA, ELISPOT assays or fluorescence-activated cell sorting (FACS) to determine the rate and total amount of cytokine production. (Fujihashi K. et al. (1993) J. Immunol. Meth. 160:181; Tanguay S. and Killion J. J. (1994) Lymphokine Cytokine Res. 13:259).

In another embodiment, CTL activity is determined by $^{51}$Cr-release lysis assay. Lysis of peptide-pulsed $^{51}$Cr-labeled targets by antigen-specific T cells can be compared for target cells pulsed with control peptide. In another embodiment, T cells are stimulated with a peptide of this invention, and lysis of target cells expressing the native peptide in the context of MHC can be determined. The kinetics of lysis as well as overall target lysis at a fixed timepoint (e.g., 4 hours) are used, in another embodiment, to evaluate ligand performance. (Ware C. F. et al. (1983) J Immunol 131: 1312).

Methods of determining affinity of a peptide for an HLA molecule are well known in the art. In another embodiment, affinity is determined by TAP stabilization assays (Examples).

In another embodiment, affinity is determined by competition radioimmunoassay. In another embodiment, the following protocol is utilized: Target cells are washed two times in PBS with 1% bovine serum albumin (BSA; Fisher Chemicals, Fairlawn, N.J.). Cells are resuspended at 10$^7$/ml on ice, and the native cell surface bound peptides are stripped for 2 minutes at 0° C. using citrate-phosphate buffer in the presence of 3 mg/ml beta$_2$ microglobulin. The pellet is resuspended at 5×10$^6$ cells/ml in PBS/1% BSA in the presence of 3 mg/ml beta$_2$ microglobulin and 30 mg/ml deoxyribonuclease, and 200 ml aliquots are incubated in the presence or absence of HLA-specific peptides for 10 min at 20° C., then with $^{125}$I-labeled peptide for 30 min at 20° C. Total bound $^{125}$I is determined after two washes with PBS/2% BSA and one wash with PBS. Relative affinities are determined by comparison of escalating concentrations of the test peptide versus a known binding peptide.

In another embodiment, a specificity analysis of the binding of peptide to HLA on surface of live cells (e.g. SKLY-16 cells) is conducted to confirm that the binding is to the appropriate HLA molecule and to characterize its restriction. This includes, in another embodiment, competition with excess unlabeled peptides known to bind to the same or disparate HLA molecules and use of target cells which express the same or disparate HLA types. This assay is performed, in another embodiment, on live fresh or 0.25% paraformaldehyde-fixed human PBMC, leukemia cell lines and EBV-transformed T-cell lines of specific HLA types. The relative avidity of the peptides found to bind MHC molecules on the specific cells are assayed by competition assays as described above against $^{125}$I-labeled peptides of known high affinity for the relevant HLA molecule, e.g., tyrosinase or HBV peptide sequence.

In another embodiment, a peptide of methods and compositions of the present invention comprises one or more non-classical amino acids such as: 1,2,3,4-tetrahydroisoquinoline-3-carboxylate (Kazmierski et al. (1991) J. Am Chem. Soc. 113:2275-2283); (2S,3S)-methyl-phenylalanine, (2S, 3R)-methyl-phenylalanine, (2R,3S)-methyl-phenylalanine and (2R,3R)-methyl-phenylalanine (Kazmierski and Hruby (1991) Tetrahedron Lett. 32(41): 5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1984) J. Takeda Res. Labs. 43:53-76) histidine isoquinoline carboxylic acid (Zechel et al. (1991) Int. J. Pep. Protein Res. 38(2):131-138); and HIC (histidine cyclic urea), (Dharanipragada et al. (1993) Int. J. Pep. Protein Res. 42(1):68-77) and ((1992) Acta. Crst., Crystal Struc. Comm 48(IV):1239-124).

In another embodiment, a peptide of methods and compositions of the present invention comprises one or more AA analogs or is a peptidomimetic, which, in other embodiments, induces or favors specific secondary structures. Such peptides comprise, in other embodiments, the following:

LL-Acp (LL-3-amino-2-propenidone-6-carboxylic acid), a β-turn inducing dipeptide analog (Kemp et al. (1985) J. Org. Chem. 50:5834-5838); β-sheet inducing analogs (Kemp et al. (1988) Tetrahedron Lett. 29:5081-5082); β-turn inducing analogs (Kemp et al. (1988) Tetrahedron Left. 29:5057-5060); alpha-helix inducing analogs (Kemp et al. (1988) Tetrahedron Left. 29:4935-4938); gamma-turn inducing analogs (Kemp et al. (1989) J. Org. Chem. 54:109:115); analogs provided by the following references: Nagai and Sato (1985) Tetrahedron Left. 26:647-650; and DiMaio et al. (1989) J. Chem. Soc. Perkin Trans. p. 1687; a Gly-Ala turn analog (Kahn et al. (1989) Tetrahedron Lett. 30:2317); amide bond isostere (Jones et al. (1988) Tetrahedron Left. 29(31):3853-3856); tretrazol (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 55(3):936-940. Conformationally restricted mimetics of beta turns and beta bulges, and peptides containing them, are described in U.S. Pat. No. 5,440,013, issued Aug. 8, 1995 to Kahn.

In other embodiments, a peptide of the invention is conjugated to one of various other molecules, as described hereinbelow, which can be via covalent or non-covalent linkage (complexed), the nature of which varies, in another embodiment, depending on the particular purpose. In another embodiment, the peptide is covalently or non-covalently complexed to a macromolecular carrier, (e.g. an immunogenic carrier), including, but not limited to, natural and synthetic polymers, proteins, polysaccharides, polypeptides (amino acids), polyvinyl alcohol, polyvinyl pyrrolidone, and lipids. In another embodiment, a peptide of this invention is linked to a substrate. In another embodiment, the peptide is conjugated to a fatty acid, for introduction into a liposome (U.S. Pat. No. 5,837,249). In another embodiment, a peptide of the invention is complexed covalently or non-covalently with a solid support, a variety of which are known in the art. In another embodiment, linkage of the peptide to the carrier, substrate, fatty acid, or solid support serves to increase an elicited an immune response.

In other embodiments, the carrier is thyroglobulin, an albumin (e.g. human serum albumin), tetanus toxoid, polyamino acids such as poly (lysine: glutamic acid), an influenza protein, hepatitis B virus core protein, keyhole limpet hemocyanin, an albumin, or another carrier protein or carrier peptide; hepatitis B virus recombinant vaccine, or an APC. Each possibility represents a separate embodiment of the present invention.

In another embodiment, the term "amino acid" refers to a natural or, in another embodiment, an unnatural or synthetic AA, and can include, in other embodiments, glycine, D- or L optical isomers, AA analogs, peptidomimetics, or combinations thereof.

In another embodiment, the terms "cancer," "neoplasm," "neoplastic" or "tumor," are used interchangeably and refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. In another embodiment, a tumor is detectable on the basis of tumor mass; e.g., by such procedures as CAT scan, magnetic resonance imaging (MRI), X-ray, ultrasound or palpation, and in another embodiment, is identified by biochemical or immunologic findings, the latter which is used to identify cancerous cells, as well, in other embodiments.

Methods for synthesizing peptides are well known in the art. In another embodiment, the peptides of this invention are synthesized using an appropriate solid-state synthetic procedure (see for example, Steward and Young, *Solid Phase Peptide Synthesis*, Freemantle, San Francisco, Calif. (1968); Merrifield (1967) Recent Progress in Hormone Res 23: 451). The activity of these peptides is tested, in other embodiments, using assays as described herein.

In another embodiment, the peptides of this invention are purified by standard methods including chromatography (e.g., ion exchange, affinity, and sizing column chromatography), centrifugation, differential solubility, or by any other standard technique for protein purification. In another embodiment, immuno-affinity chromatography is used, whereby an epitope is isolated by binding it to an affinity column comprising antibodies that were raised against that peptide, or a related peptide of the invention, and were affixed to a stationary support.

In another embodiment, affinity tags such as hexa-His (Invitrogen), Maltose binding domain (New England Biolabs), influenza coat sequence (Kolodziej et al. (1991) Meth. Enzymol. 194:508-509), glutathione-S-transferase, or others, are attached to the peptides of this invention to allow easy purification by passage over an appropriate affinity column. Isolated peptides can also be physically characterized, in other embodiments, using such techniques as proteolysis, nuclear magnetic resonance, and x-ray crystallography.

In another embodiment, the peptides of this invention are produced by in vitro translation, through known techniques, as will be evident to one skilled in the art. In another embodiment, the peptides are differentially modified during or after translation, e.g., by phosphorylation, glycosylation, cross-linking, acylation, proteolytic cleavage, linkage to an antibody molecule, membrane molecule or other ligand, (Ferguson et al. (1988) Ann. Rev. Biochem. 57:285-320).

In another embodiment, the peptides of this invention further comprise a detectable label, which in another embodiment, is fluorescent, or in another embodiment, luminescent, or in another embodiment, radioactive, or in another embodiment, electron dense. In other embodiments, the detectable label comprises, for example, green fluorescent protein (GFP), DS-Red (red fluorescent protein), secreted alkaline phosphatase (SEAP), beta-galactosidase, luciferase, $^{32}P$, $^{125}I$, $^{3}H$ and $^{14}C$, fluorescein and its derivatives, rhodamine and its derivatives, dansyl and umbelliferone, luciferin or any number of other such labels known to one skilled in the art. The particular label used will depend upon the type of immunoassay used.

In another embodiment, a peptide of this invention is linked to a substrate, which, in another embodiment, serves as a carrier. In another embodiment, linkage of the peptide to a substrate serves to increase an elicited an immune response.

In another embodiment, peptides of this invention are linked to other molecules, as described herein, using conventional cross-linking agents such as carbodimides. Examples of carbodimides are 1-cyclohexyl-3-(2-morpholinyl-(4-ethyl) carbodiimide (CMC), 1-ethyl-3-(3-dimethylaminopropyl) carbodiimide (EDC) and 1-ethyl-3-(4-azonia-44-dimethylpentyl) carbodiimide.

In other embodiments, the cross-linking agents comprise cyanogen bromide, glutaraldehyde and succinic anhydride.

In general, any of a number of homo-bifunctional agents including a homo-bifunctional aldehyde, a homo-bifunctional epoxide, a homo-bifunctional imido-ester, a homo-bifunctional N-hydroxysuccinimide ester, a homo-bifunctional maleimide, a homo-bifunctional alkyl halide, a homo-bifunctional pyridyl disulfide, a homo-bifunctional aryl halide, a homo-bifunctional hydrazide, a homo-bifunctional diazonium derivative and a homo-bifunctional photoreactive compound can be used. Also envisioned, in other embodiments, are hetero-bifunctional compounds, for example, compounds having an amine-reactive and a sulfhydryl-reactive group, compounds with an amine-reactive and a photoreactive group and compounds with a carbonyl-reactive and a sulfhydryl-reactive group.

In other embodiments, the homo-bifunctional cross-linking agents include the bifunctional N-hydroxysuccinimide esters dithiobis(succinimidylpropionate), disuccinimidyl suberate, and disuccinimidyl tartarate; the bifunctional imido-esters dimethyl adipimidate, dimethyl pimelimidate, and dimethyl suberimidate; the bifunctional sulfhydryl-reactive crosslinkers 1,4-di-[3'-(2'-pyridyldithio)propionamido]butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as a1a'-diiodo-p-xylene sulfonic acid and tri(2-chloroethyl)amine, respectively.

In other embodiments, hetero-bifunctional cross-linking agents used to link the peptides to other molecules, as described herein, include, but are not limited to, SMCC (succinimidyl-4-(N-maleimidomethyl)cyclohexane-1-carboxylate), MBS (m-maleimidobenzoyl-N-hydroxysuccinimide ester), SIAB (N-succinimidyl(4-iodoacteyl)aminobenzoate), SMPB (succinimidyl-4-(p-maleimidophenyl) butyrate), GMBS (N-(.gamma.-maleimidobutyryloxy) succinimide ester), MPBH (4-(4-N-maleimidopohenyl) butyric acid hydrazide), M2C2H (4-(N-maleimidomethyl) cyclohexane-1-carboxyl-hydrazide), SMPT (succinimidyloxycarbonyl-a-methyl-a-(2-pyridyldithio)toluene), and SPDP (N-succinimidyl 3-(2-pyridyldithio)propionate).

In another embodiment, the peptides of the invention are formulated as non-covalent attachment of monomers through ionic, adsorptive, or biospecific interactions. Complexes of peptides with highly positively or negatively charged molecules can be accomplished, in another embodiment, through salt bridge formation under low ionic strength environments, such as in deionized water. Large complexes can be created, in another embodiment, using charged polymers such as poly-(L-glutamic acid) or poly-(L-lysine), which contain numerous negative and positive charges, respectively. In another embodiment, peptides are adsorbed to surfaces such as microparticle latex beads or to other hydrophobic polymers, forming non-covalently associated peptide-superantigen complexes effectively mimicking cross-linked or chemically polymerized protein, in other embodiments. In another embodiment, peptides are non-covalently linked through the use of biospecific interactions between other molecules. For instance, utilization of the strong affinity of biotin for proteins such as avidin or streptavidin or their derivatives could be used to form peptide complexes. The peptides, according to this aspect, and in another embodiment, can be modified to possess biotin groups using common biotinylation reagents such as the N-hydroxysuccinimidyl ester of D-biotin (NHS-biotin), which reacts with available amine groups.

In another embodiment, a peptide of the present invention is linked to a carrier. In another embodiment, the carrier is KLH. In other embodiments, the carrier is any other carrier known in the art, including, for example, thyroglobulin, albumins such as human serum albumin, tetanus toxoid, polyamino acids such as poly (lysine:glutamic acid), influenza, hepatitis B virus core protein, hepatitis B virus recombinant vaccine and the like. Each possibility represents a separate embodiment of the present invention.

In another embodiment, the peptides of this invention are conjugated to a lipid, such as P3 CSS. In another embodiment, the peptides of this invention are conjugated to a bead.

In another embodiment, the compositions of this invention further comprise immunomodulating compounds. In other embodiments, the immunomodulating compound is a cytokine, chemokine, or complement component that enhances expression of immune system accessory or adhesion molecules, their receptors, or combinations thereof. In some embodiments, the immunomodulating compound include interleukins, for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components, or combinations thereof. In other embodiments, the immunomodulating compound stimulate expression, or enhanced expression of OX40, OX40L (gp34), lymphotactin, CD40, CD40L, B7.1, B7.2, TRAP, ICAM-1, 2 or 3, cytokine receptors, or combination thereof.

In another embodiment, the immunomodulatory compound induces or enhances expression of co-stimulatory molecules that participate in the immune response, which include, in some embodiments, CD40 or its ligand, CD28, CTLA-4 or a B7 molecule. In another embodiment, the immunomodulatory compound induces or enhances expression of a heat stable antigen (HSA) (Liu Y. et al. (1992) J. Exp. Med. 175:437-445), chondroitin sulfate-modified MHC invariant chain (Ii-CS) (Naujokas M. F. et al. (1993) Cell 74:257-268), or an intracellular adhesion molecule 1 (ICAM-1) (Van R. H. (1992) Cell 71:1065-1068), which assists, in another embodiment, co-stimulation by interacting with their cognate ligands on the T cells.

In another embodiment, the composition comprises a solvent, including water, dispersion media, cell culture media, isotonic agents and the like. In another embodiment, the solvent is an aqueous isotonic buffered solution with a pH of around 7.0. In another embodiment, the composition comprises a diluent such as water, phosphate buffered saline, or saline. In another embodiment, the composition comprises a solvent, which is non-aqueous, such as propyl ethylene glycol, polyethylene glycol and vegetable oils.

In another embodiment, the composition is formulated for administration by any of the many techniques known to those of skill in the art. For example, this invention provides for administration of the pharmaceutical composition parenterally, intravenously, subcutaneously, intradermally, intramucosally, topically, orally, or by inhalation.

In another embodiment, the vaccine comprising a peptide of this invention further comprises a cell population, which, in another embodiment, comprises lymphocytes, monocytes, macrophages, dendritic cells, endothelial cells, stem cells or combinations thereof, which, in another embodiment are autologous, syngeneic or allogeneic, with respect to each other. In another embodiment, the cell population comprises a peptide of the present invention. In another embodiment, the cell population takes up the peptide. Each possibility represents a separate embodiment of the present invention.

In another embodiment, the cell populations of this invention are obtained from in vivo sources, such as, for example, peripheral blood, leukopheresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, granulomatous tissue, or any other source where such cells can be obtained. In another embodiment, the cell populations are obtained from human sources, which are, in other embodiments, from human fetal, neonatal, child, or adult sources. In another embodiment, the cell populations of this invention are obtained from animal sources, such as, for example, porcine or simian, or any other animal of interest. In another embodiment, the cell populations of this invention are obtained from subjects that are normal, or in another embodiment, diseased, or in another embodiment, susceptible to a disease of interest.

In another embodiment, the cell populations of this invention are separated via affinity-based separation methods. Techniques for affinity separation include, in other embodiments, magnetic separation, using antibody-coated magnetic beads, affinity chromatography, cytotoxic agents joined to a monoclonal antibody or use in conjunction with a monoclonal antibody, for example, complement and cytotoxins, and "panning" with an antibody attached to a solid matrix, such as a plate, or any other convenient technique. In other embodiment, separation techniques include the use of fluorescence activated cell sorters, which can have varying degrees of sophistication, such as multiple color channels, low angle and obtuse light scattering detecting channels, impedance channels, etc. In other embodiments, any technique that enables separation of the cell populations of this invention can be employed, and is to be considered as part of this invention.

In another embodiment, the dendritic cells are from the diverse population of morphologically similar cell types found in a variety of lymphoid and non-lymphoid tissues, qualified as such (Steinman (1991) Ann. Rev. Immunol. 9:271-296). In another embodiment, the dendritic cells used in this invention are isolated from bone marrow, or in another embodiment, derived from bone marrow progenitor cells, or, in another embodiment, from isolated from/derived from peripheral blood, or in another embodiment, derived from, or are a cell line.

In another embodiment, the cell populations described herein are isolated from the white blood cell fraction of a mammal, such as a murine, simian or a human (See, e.g., WO 96/23060). The white blood cell fraction can be, in another embodiment, isolated from the peripheral blood of the mammal.

Methods of isolating dendritic cells are well known in the art. In another embodiment, the DC are isolated via a method which includes the following steps: (a) providing a white blood cell fraction obtained from a mammalian source by methods known in the art such as leukophoresis; (b) separating the white blood cell fraction of step (a) into four or more subfractions by countercurrent centrifugal elutriation; (c) stimulating conversion of monocytes in one or more fractions from step (b) to dendritic cells by contacting the cells with calcium ionophore, GM-CSF and IL-13 or GM-CSF and IL-4, (d) identifying the dendritic cell-enriched fraction from step (c); and (e) collecting the enriched fraction of step (d), preferably at about 4° C.

In another embodiment, the dendritic cell-enriched fraction is identified by fluorescence-activated cell sorting, which identifies, in another embodiment, at least one of the following markers: HLA-DR, HLA-DQ, or B7.2, and the simultaneous absence of the following markers: CD3, CD14, CD16, 56, 57, and CD 19, 20.

In another embodiment, the cell population comprises lymphocytes, which are, in another embodiment, T cells, or in another embodiment, B cells. The T cells are, in other embodiments, characterized as NK cells, helper T cells, cytotoxic T lymphocytes (CTL), TILs, naïve T cells, or combinations thereof. It is to be understood that T cells which are primary, or cell lines, clones, etc. are to be considered as part of this invention. In another embodiment, the T cells are CTL, or CTL lines, CTL clones, or CTLs isolated from tumor, inflammatory, or other infiltrates.

In another embodiment, hematopoietic stem or early progenitor cells comprise the cell populations used in this invention. In another embodiment, such populations are isolated or derived, by leukapheresis. In another embodiment, the leukapheresis follows cytokine administration, from bone marrow, peripheral blood (PB) or neonatal umbilical cord blood. In another embodiment the stem or progenitor cells are characterized by their surface expression of the surface antigen marker known as $CD34^+$, and exclusion of expression of the surface lineage antigen markers, Lin–.

In another embodiment, the subject is administered a peptide, composition or vaccine of this invention, in conjunction with bone marrow cells. In another embodiment, the administration together with bone marrow cells embodiment follows previous irradiation of the subject, as part of the course of therapy, in order to suppress, inhibit or treat cancer in the subject.

In another embodiment, the phrase "contacting a cell" or "contacting a population" refers to a method of exposure, which can be, in other embodiments, direct or indirect. In another embodiment, such contact comprises direct injection of the cell through any means well known in the art, such as microinjection. It is also envisaged, in another embodiment, that supply to the cell is indirect, such as via provision in a culture medium that surrounds the cell, or administration to a subject, via any route well known in the art, and as described herein.

In another embodiment, CTL generation of methods of the present invention is accomplished in vivo, and is effected by introducing into a subject an antigen presenting cell contacted in vitro with a peptide of this invention (See for example Paglia et al. (1996) J. Exp. Med. 183:317-322).

In another embodiment, the peptides of methods and compositions of the present invention are delivered to antigen-presenting cells (APC).

In another embodiment, the peptides are delivered to APC in the form of cDNA encoding the peptides. In another embodiment, the term "antigen-presenting cells" refers to dendritic cells (DC), monocytes/macrophages, B lymphocytes or other cell type(s) expressing the necessary MHC/co-stimulatory molecules, which effectively allow for T cell recognition of the presented peptide. In another embodiment, the APC is a cancer cell. Each possibility represents a separate embodiment of the present invention.

In another embodiment, the CTL are contacted with two or more antigen-presenting cell populations. In another embodiment, the two or more antigen presenting cell populations present different peptides. Each possibility represents a separate embodiment of the present invention.

In another embodiment, techniques that lead to the expression of antigen in the cytosol of APC (e.g. DC) are used to deliver the peptides to the APC. Methods for expressing antigens on APC are well known in the art. In another embodiment, the techniques include (1) the introduction into the APC of naked DNA encoding a peptide of this invention, (2) infection of APC with recombinant vectors expressing a peptide of this invention, and (3) introduction of a peptide of this invention into the cytosol of an APC using liposomes. (See Boczkowski D. et al. (1996) J. Exp. Med. 184:465-472; Rouse et al. (1994) J. Virol. 68:5685-5689; and Nair et al. (1992) J. Exp. Med. 175:609-612).

In another embodiment, foster antigen presenting cells such as those derived from the human cell line 174× CEM.T2, referred to as T2, which contains a mutation in its antigen processing pathway that restricts the association of endogenous peptides with cell surface MHC class I molecules (Zweerink et al. (1993) J. Immunol. 150:1763-1771), are used, as exemplified herein.

In another embodiment, any of the methods described herein is used to elicit CTL, which are elicited in vitro. In another embodiment, the CTL are elicited ex-vivo. In another embodiment, the CTL are elicited in vitro. The resulting CTL, are, in another embodiment, administered to the subject, thereby treating the condition associated with the peptide, an expression product comprising the peptide, or a homologue thereof. Each possibility represents a separate embodiment of the present invention.

In another embodiment, the method entails introduction of the genetic sequence that encodes the peptides of this invention. In another embodiment, the method comprises administering to the subject a vector comprising a nucleotide sequence, which encodes a peptide of the present invention (Tindle, R. W. et al. Virology (1994) 200:54). In another embodiment, the method comprises administering to the subject naked DNA which encodes a peptide, or in another embodiment, two or more peptides of this invention (Nabel, et al. PNAS-USA (1990) 90: 11307). In another embodiment, multi-epitope, analogue-based cancer vaccines are utilized (Fikes et al, ibid). Each possibility represents a separate embodiment of the present invention.

Nucleic acids can be administered to a subject via any means as is known in the art, including parenteral or intravenous administration, or in another embodiment, by means of a gene gun. In another embodiment, the nucleic acids are administered in a composition, which correspond, in other embodiments, to any embodiment listed herein.

Vectors for use according to methods of this invention can comprise, in another embodiment, any vector that facilitates or allows for the expression of a peptide of this invention. In another embodiment, "vectors" includes attenuated viruses, such as vaccinia or fowlpox, such as described in, e.g., U.S. Pat. No. 4,722,848, incorporated herein by reference. In another embodiment, the vector is BCG (Bacille Calmette Guerin), such as described in Stover et al. (Nature 351:456-460 (1991)). Other vectors useful for therapeutic administration or immunization of the peptides of the invention, e.g., Salmonella typhi vectors and the like, will be apparent to those skilled in the art from the description herein.

In another embodiment, the vector further encodes for an immunomodulatory compound, as described herein. In another embodiment, the subject is administered an additional vector encoding same, concurrent, prior to or following administration of the vector encoding a peptide of this invention to the subject.

In another embodiment, the peptides, compositions and vaccines of this invention are administered to a subject, or utilized in the methods of this invention, in combination with other anti-cancer compounds and chemotherapeutics, including monoclonal antibodies directed against alternate cancer antigens, or, in another embodiment, epitopes that consist of an AA sequence which corresponds to, or in part to, that from which the peptides of this invention are derived.

In another embodiment, the present invention provides a method of detecting a WT1-specific CD4$^+$ T cell response in a subject, the method comprising administering to the subject a peptide, vaccine, or immunogenic composition of the present invention. In another embodiment, a delayed-type hypersensitivity test used to detect the WT1-specific CD4$^+$ T cell response. In another embodiment, a peptide of present invention is superior to its unmutated counterpart in inducing a CD4$^+$ T cell response in a subject. Each possibility represents a separate embodiment of the present invention.

An immunogenic composition of methods and compositions of the present invention comprises, in another embodiment, an APC associated with a peptide of the present invention. In another embodiment, the immunogenic composition comprises an APC associated with a mixture of peptides of the present invention. In another embodiment, the immunogenic composition consists of an APC associated with a peptide of the present invention. In another embodiment, the immunogenic composition consists of an APC associated with a mixture of peptides of the present invention. Each possibility represents a separate embodiment of the present invention.

A composition of methods and compositions of the present invention is, in another embodiment, an immunogenic composition. In another embodiment, the composition is a pharmaceutical composition. In another embodiment, the composition is any other type of composition known in the art. Each possibility represents a separate embodiment of the present invention.

Various embodiments of dosage ranges are contemplated by this invention. In another embodiment, the dosage is 20 µg per peptide per day. In another embodiment, the dosage is 10 µg/peptide/day. In another embodiment, the dosage is 30 µg/peptide/day. In another embodiment, the dosage is 40 µg/peptide/day. In another embodiment, the dosage is 60 µg/peptide/day. In another embodiment, the dosage is 80 µg/peptide/day. In another embodiment, the dosage is 100 µg/peptide/day. In another embodiment, the dosage is 150 µg/peptide/day. In another embodiment, the dosage is 200 µg/peptide/day. In another embodiment, the dosage is 300 µg/peptide/day. In another embodiment, the dosage is 400 µg/peptide/day. In another embodiment, the dosage is 600 µg/peptide/day. In another embodiment, the dosage is 800 µg/peptide/day. In another embodiment, the dosage is 1000 µg/peptide/day.

In another embodiment, the dosage is 10 µg/peptide/dose. In another embodiment, the dosage is 30 µg/peptide/dose. In another embodiment, the dosage is 40 µg/peptide/dose. In another embodiment, the dosage is 60 µg/peptide/dose. In another embodiment, the dosage is 80 µg/peptide/dose. In another embodiment, the dosage is 100 µg/peptide/dose. In another embodiment, the dosage is 150 μg/peptide/dose. In another embodiment, the dosage is 200 μg/peptide/dose. In another embodiment, the dosage is 300 μg/peptide/dose. In another embodiment, the dosage is 400 μg/peptide/dose. In another embodiment, the dosage is 600 μg/peptide/dose. In another embodiment, the dosage is 800 μg/peptide/dose. In another embodiment, the dosage is 1000 μg/peptide/dose.

In another embodiment, the dosage is 10-20 μg/peptide/dose. In another embodiment, the dosage is 20-30 μg/peptide/dose. In another embodiment, the dosage is 20-40 μg/peptide/dose. In another embodiment, the dosage is 30-60 μg/peptide/dose. In another embodiment, the dosage is 40-80 μg/peptide/dose. In another embodiment, the dosage is 50-100 μg/peptide/dose. In another embodiment, the dosage is 50-150 μg/peptide/dose. In another embodiment, the dosage is 100-200 μg/peptide/dose. In another embodiment, the dosage is 200-300 μg/peptide/dose. In another embodiment, the dosage is 300-400 μg/peptide/dose. In another embodiment, the dosage is 400-600 μg/peptide/dose. In another embodiment, the dosage is 500-800 μg/peptide/dose. In another embodiment, the dosage is 800-1000 μg/peptide/dose.

In another embodiment, the total amount of peptide per dose or per day is one of the above amounts. In another embodiment, the total peptide dose per dose is one of the above amounts.

Each of the above doses represents a separate embodiment of the present invention.

In another embodiment, the present invention provides a kit comprising a peptide, composition or vaccine of the present invention. In another embodiment, the kit further comprises a label or packaging insert. In another embodiment, the kit is used for detecting a WT1-specific CD4 response through the use of a delayed-type hypersensitivity test. In another embodiment, the kit is used for any other method enumerated herein. In another embodiment, the kit is used for any other method known in the art. Each possibility represents a separate embodiment of the present invention.

EXPERIMENTAL DETAILS SECTION

Example 1: Binding of HLA-A0201 and -A0301 by Synthetic Peptide Analogues Derived from WT1

Materials and Experimental Methods

Peptides

Peptides were synthesized by Genemed Synthesis Inc, Calif. using fluorenylmethoxycarbonyl chemistry and solid phase synthesis, and were purified by high pressure liquid chromatography (HPLC). The quality of the peptides was assessed by HPLC analysis, and the expected molecular weight was measured using matrix-assisted laser desorption mass spectrometry. Peptides were sterile and >90% pure. The peptides were dissolved in DMSO and diluted in PBS at pH 7.4 or saline solution to yield a concentration of 5 milligrams per milliliter (mg/ml) and were stored at −80° C. For in vitro experiments, an irrelevant control peptide, HLA A24 consensus, was used.

Peptide Sequence Analysis

Peptide sequence analysis was performed using 2 databases. The first was the software of the Bioinformatics & Molecular Analysis Section (National Institutes of Health, Washington, D.C.) (Parker K C et al, Scheme for ranking potential HLA-A2 binding peptides based on independent binding of individual peptide side-chains. J Immunol 152: 163-175, 1994), which ranks 9-mer or 10-mer peptides on a predicted half-time dissociation coefficient from HLA class I molecules. The second database, SYFPEITHI prediction software, is described in Rammensee H G et al (SYFPEITHI: database for MHC ligands and peptide motifs. Immunogenetics 50: 213-219, 1999). Irrelevant control peptides used in in vitro experiments were: RAS (TEYKLVVVGAPGVGKSALTIQ; SEQ ID No: 49) or CML b2a2 (VHSIPLTINKEEALQRPVASDFE; SEQ ID No: 50) for Class II, and HIV pol (ILKEPVHGV; SEQ ID No: 51) or CML F (YLKALQRPY; SEQ ID No: 52) for Class I.

Cell Lines

Cell lines were cultured in RPMI 1640 medium supplemented with 5% FCS, penicillin, streptomycin, 2 mM glutamine and 2-mercaptoethanol at 37° C. in humidified air containing 5% $CO_2$. T2 is a human cell line lacking TAP1 and TAP2 and therefore unable to present peptides derived from cytosolic proteins. Raji cells are a human Burkitt lymphoma cells that exhibit a high level of TAP expression.

Human mesothelioma cell lines studied included: sarcomatoid (VAMT, H2373, H28), epithelioid (H2452) and biphasic (JMN, MSTO and H-Meso1A). Cell lines were obtained from the following sources: H-Meso1A: NCI, Bethesda, Md.; JMN and VAMT: Dr. Sirotnak, Memorial Sloan Kettering Cancer Center (MSKCC); H-2452 and H2373: Dr. Pass, Karmanos Cancer Institute, Wayne State University, Detroit, Mich.; H28 and MSTO: American Type Culture Collection (ATCC, Manassas, Va.). Cell lines were maintained in media recommended by the suppliers and incubated in a humidified incubator with 5% $CO_2$.

Mesothelioma cell lines Meso 11, Meso 34, Meso 37, Meso 47 and Meso 56 were obtained from Dr. M Gregoire (Institute of Biology, Nantes, France) and cultured in RPMI 1640 (Life Technologies)+10% fetal calf serum (FCS), 1% penicillin-streptomycin, and 1% L-glutamine. All cells were HLA typed by the Department of Cellular Immunology at MSKCC. Melanoma cell line Mewo (WT1$^-$ A201$^+$) was obtained from the ATCC. SKRC-52 renal cell carcinoma was obtained from L. Old of the Ludwig Institute. Leukemia cell lines were cultured in RPMI 1640+10% FCS, 1% penicillin-streptomycin, 2 mM glutamine and 2-mercaptoethanol at 37° C./5% $CO_2$. LAMA81, BV173 and 697, Ph$^+$ leukemias that are all WT1$^+$ and A0201$^+$, were provided by Dr. HJ Stauss (University College London). SKLY-16 is a human B cell lymphoma (WT1$^-$, A0201$^+$); K562, RwLeu4 and HL60, all WT1$^+$ leukemias, were obtained from the ATCC.

T2 Assay for Peptide Binding and Stabilization of HLA A0201 Molecules

T2 cells (TAP$^-$, HLA-A0201$^+$) were incubated overnight at 27° C. at a concentration of 1×10$^6$ cells/ml in FCS-free RPMI medium supplemented with 5 μg/ml human $\beta_2$m (Sigma, St Louis, Mo.) in the absence (negative control) or presence of either a positive reference tyrosinase peptide or test peptides at various final concentrations (50, 10, 1, and 0.1 micrograms (μg)/ml). Following a 4-hour incubation with 5 μg/ml brefeldin A (Sigma), T2 cells were labeled for 30 minutes at 4° C. with a saturating concentration of anti-HLA-A2.1 (BB7.2) mAb, then washed twice. Cells were then incubated for 30 minutes, 4° C. with a saturating concentration of FITC-conjugated goat IgG F(ab')2 anti-mouse Ig (Caltag, San Francisco, Calif.), washed twice, fixed in PBS/1% paraformaldehyde and analyzed using a FACS Calibur® cytofluorometer (Becton Dickinson, Immunocytometry Systems, San Jose, Calif.).

The mean intensity of fluorescence (MIF) observed for each peptide concentration (after dividing by the MIF in the absence of peptide) was used as an indication of peptide binding and expressed as a "fluorescence index." Stabilization assays were performed similarly. Following initial evaluation of peptide binding at time 0, cells were washed in RPMI complete medium to remove free peptides and incubated in the continuous presence of 0.5 µg/ml brefeldin-A for 2, 4, 6 or 8 hours.

The number of stable peptide-HLA-A2.1 complexes was estimated as described above by immunofluorescence. The half time of complexes is an estimate of the time required for a 50% reduction of the MIF value at time=0.

Results

Peptides having predicted affinity for HLA-A0201 and HLA-A0301 molecules were identified from the WT1 sequence. These WT1 native peptides were modified to generate heteroclitic peptides with increased predicted binding to HLA-A0201 and HLA-A0301 molecules, as shown in Tables 1-2. Several of the heteroclitic peptides significantly stabilized HLA-A0201 and HLA-A0301 molecules in thermostabilization assays using a TAP 1/2 negative cell line (T2) and Raji HLA-A0301 cells. Specifically, WT1-A1, B1, and C1 exhibited similar or increased binding compared to the corresponding native peptides WT1-A, B, and C. WT1-D1 exhibited similar or increased binding compared to corresponding native peptide WT1-D (FIG. 1A). A comparison of HLA A0301 binding of A3 WT1-A, -B, -C, and -D with each of their respective three analogues demonstrated similar binding (FIGS. 1B-5E).

Thus, heteroclitic WT1 peptides of the present invention exhibit enhanced binding to HLA class I molecules.

TABLE 1

HLA 0201-binding native peptides from WT1 and synthetic analogues

| Name | Sequence | SEQ ID NO: | BIMAS score |
|---|---|---|---|
| WT1 A (native) | RMFPNAPYL | 5 | 313 |
| WT1 A1 (analogue) | YMFPNAPYL | 6 | 1444 |
| WT1 B (native) | SLGEQQYSV | 7 | 285 |
| WT1 B1 (analogue) | YLGEQQYSV | 8 | 1311 |
| WT1 C (native) | ALLPAVPSL | 9 | 181 |
| WT1 C1 (analogue) | YLLPAVPSL | 10 | 836 |
| WT1 D (native) | NLGATLKGV | 11 | 159 |
| WT1 D1 (analogue) | YLGATLKGV | 12 | 735 |
| WT1 E (native) | DLNALLPAV | 13 | 11 |
| WT1 E1 (analogue) | YLNALLPAV | 14 | 735 |
| WT1 F (native) | GVFRGIQDV | 15 | 51 |
| WT1 F1 (analogue) | GLRRGIQDV | 16 | 12 |
| WT1 G (native) | KRYFKLSHL | 17 | 1 |
| WT1 G1 (analogue) | KLYFKLSHL | 18 | 550 |
| WT1 H (native) | ALLLRTPYS | 19 | 1 |

TABLE 1-continued

HLA 0201-binding native peptides from WT1 and synthetic analogues

| Name | Sequence | SEQ ID NO: | BIMAS score |
|---|---|---|---|
| WT1 H1 (analogue) | ALLLRTPYV | 20 | 1415 |
| WT1 J (native) | CMTWNQMNL | 21 | 15 |
| WT1 J1 (analogue) | YMTWNQMNL | 22 | 70 |

TABLE 2

HLA 0201-binding native peptides from WT1 and synthetic analogues

| Name | Sequence | SEQ ID | BIMAS score |
|---|---|---|---|
| A3 WT1 A (native) | NMHQRNMTK | 23 | 40 |
| A3 WT1 A1 (analogue) | NMYQRNMTK | 24 | 200 |
| A3WT1 A2 (analogue) | NMHQRVMTK | 25 | 120 |
| A3 WT1 A3 (analogue) | NMYQRVMTK | 26 | 600 |
| A3 WT1 B (native) | QMNLGATLK | 27 | 20 |
| A3WT1 B1 (analogue) | QMYLGATLK | 28 | 100 |
| A3WT1 B2 (analogue) | QMNLGVTLK | 29 | 60 |
| A3WT1 B3 (analogue) | QMYLGVTLK | 30 | 300 |
| A3WT1 C (native) | FMCAYPGCNK | 31 | 30 |
| A3WT1 C1 (analogue) | FMYAYPGCNK | 32 | 150 |
| A3 WT1 C2 (analogue) | FMCAYPFCNK | 33 | 90 |
| A3 WT1 C3 (analogue) | FMYAYPFCNK | 34 | 450 |
| A3WT1 D (native) | KLSHLQMHSR | 35 | 18 |
| A3WT1 D1 (analogue) | KLYHLQMHSR | 36 | 90 |
| A3 WT1 D2 (analogue) | KLSHLQMHSK | 37 | 90 |
| A3 WT1 D3 (analogue) | KLYHLQMHSK | 38 | 450 |

Example 2: Induction of Immune Responses Against Synthetic Peptide Analogues Derived from WT1

Materials and Experimental Methods

Peptide Stimulations

PBMC were purified from HLA-A0201 positive healthy donors and CML patients by centrifugation in Ficoll-Paque centrifugation medium (Amersham Biosciences). Peripheral blood dendritic cells (DC) were generated as follows: Monocyte-enriched PBMC fractions were isolated, using a plastic adherence technique, from total PBMC. The plastic-adherent cells were cultured further in RPMI 1640 medium (Invitrogen) containing 1-5% autologous plasma, 1000 units per milliliter (U/mL) recombinant human interleukin (IL)-4 (Schering-Plough, N.J.), and 1000 U/mL recombinant human granulocyte-macrophage colony-stimulating factor (GM-CSF) (Immunex, Seattle).

On days 2 and 4 of incubation, fresh culture medium supplemented with IL-4 and GM-CSF was added. On day 6, half of the medium was exchanged for culture medium containing IL-4, GM-CSF, 10 ng/mL recombinant human tumor necrosis factor (TNF)-alpha (R&D system) and 500 ng/ml trimeric soluble CD40L (Immunex, Seattle). On day 9, cells were harvested and used as APC for antigen stimulation. The cells expressed DC-associated antigens, such as CD80, CD83, CD86, and HLA class I and class II on their cell surfaces.

T lymphocytes were isolated from the same donors by use of negative selection by depletion with an anti-CD11b, anti-CD56 and CD19 monoclonal antibody (Miltenyi, Calif.). $1 \times 10^{\wedge}6$ T lymphocytes were cultured with $1 \times 10^{\wedge}5$ autologous DC in RPMI 1640 containing 5% heat-inactivated human autologous plasma with 10 µg/mL peptide and 2 µg/ml $\beta_2$ microglobulin, 5 ng/mL recombinant human IL-7 (Genzyme), and 0.1 ng/ml IL-12 in 24 well plates.

After culture for 3 days, 20 U/ml of recombinant IL-2 (Sandoz Pharmaceutical) was added. After 10 days, $1 \times 10^{\wedge}6$ cells were stimulated again by adding $2 \times 10^{\wedge}5$ autologous magnetically isolated CD14+ monocytes together with 10 ng/ml IL-7, 20 U/ml IL-2, and 10 µg/mL peptide. In some cases, after culture for another 7 days, the cells were stimulated a third time in the same manner. After the last stimulation, CD8+ T cells were isolated magnetically, and cytotoxicity and gamma-IFN secretion of these cells were determined.

Results

Figure 2A:
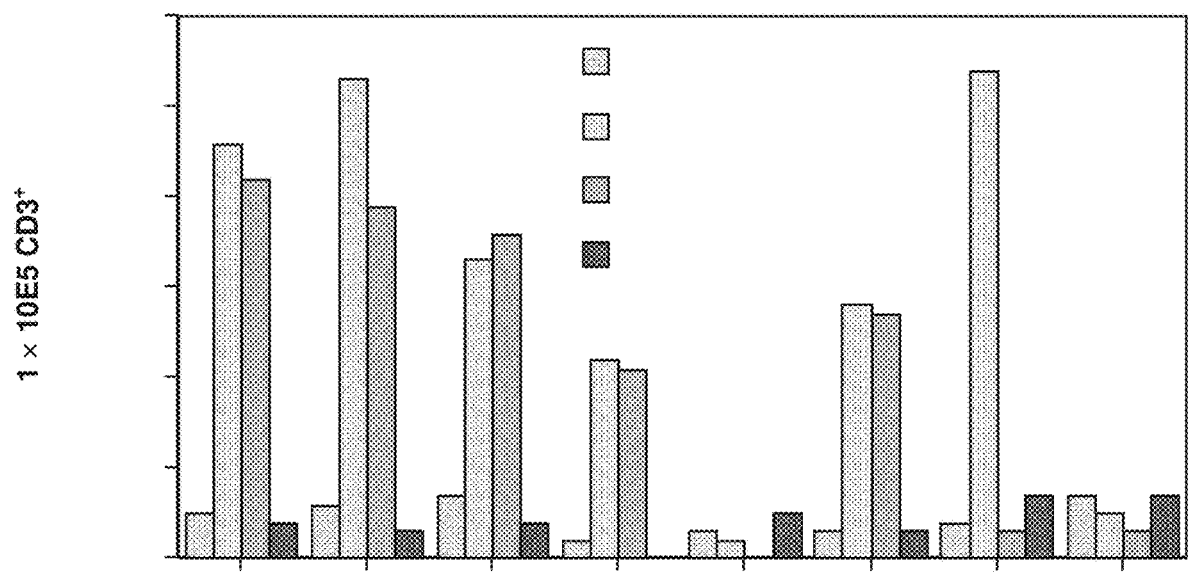
FIG. 2: CD8+/CD3+ gamma interferon (IFN) ELISPOT (A) and cytotoxicity (B) from healthy HLA A0201 donors against T2 cells pulsed with the following peptides: 1st bar in each series: no peptide; $2^{nd}$ bar: same peptide used for stimulation; $3^{rd}$ bar: corresponding native peptide; $4^{th}$ bar: negative control peptide. X axis: peptides used for stimulations. Experiments were performed in triplicate and confirmed 3-5 times.
Figure 2B:
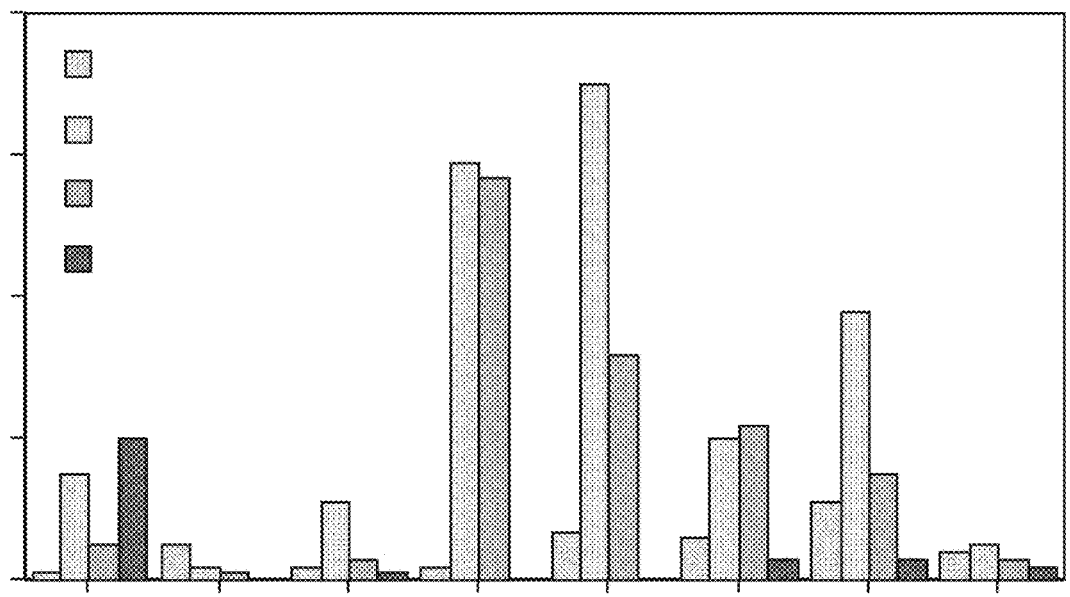
Figure 3A:
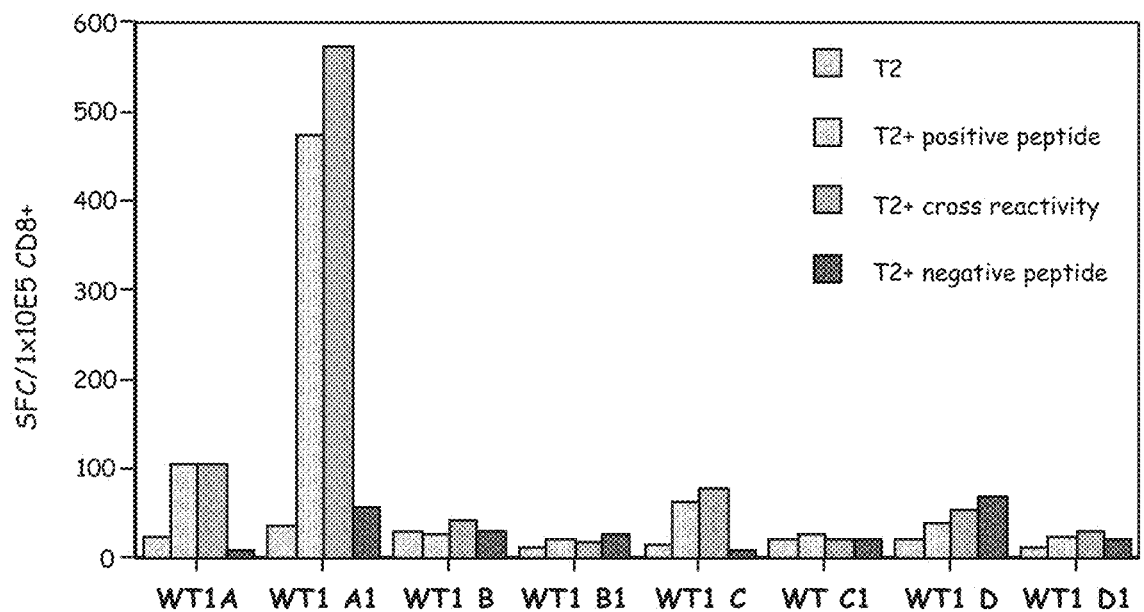
FIG. 3: CD8+ (A) and CD3+ (B-D) gamma IFN ELISPOT from healthy HLA A0201 donors using the indicated peptides-assignment of bars in each series is the same as for FIG. 2. Each subfigure in B-D represents a separate repetition of the experiment].
Figure 3B:
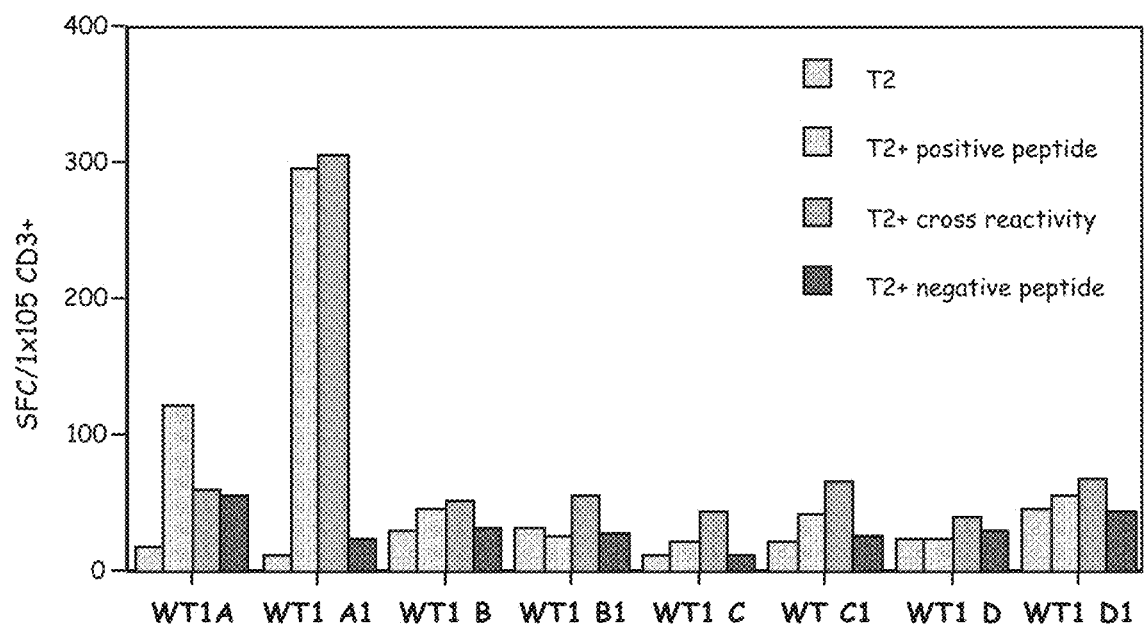
Figure 3C:
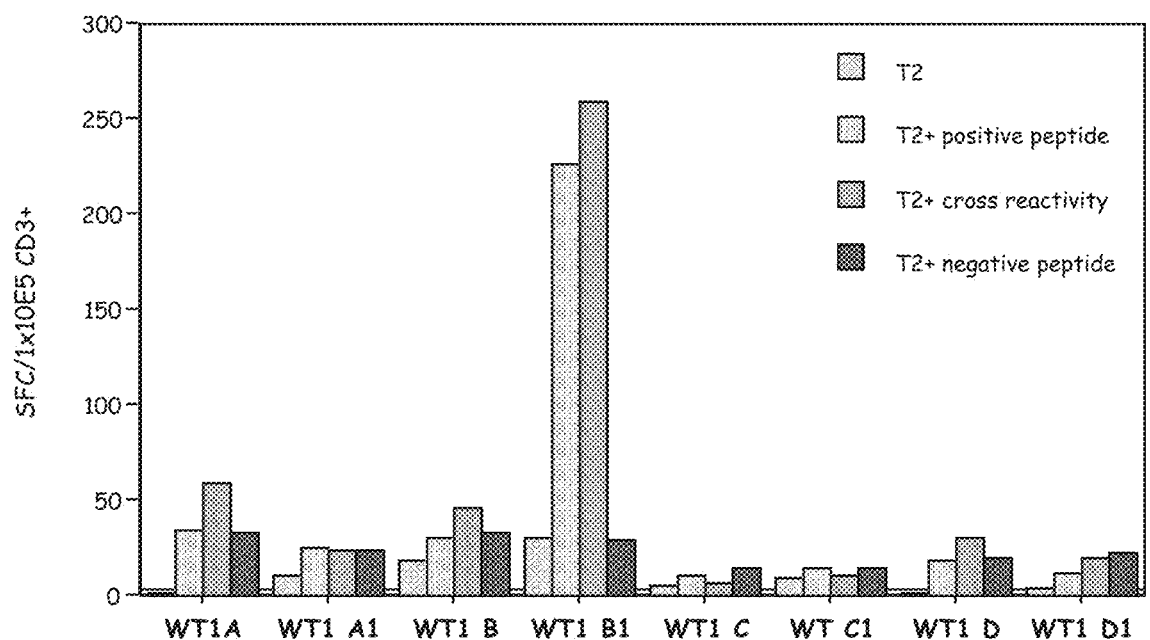
Figure 3D:
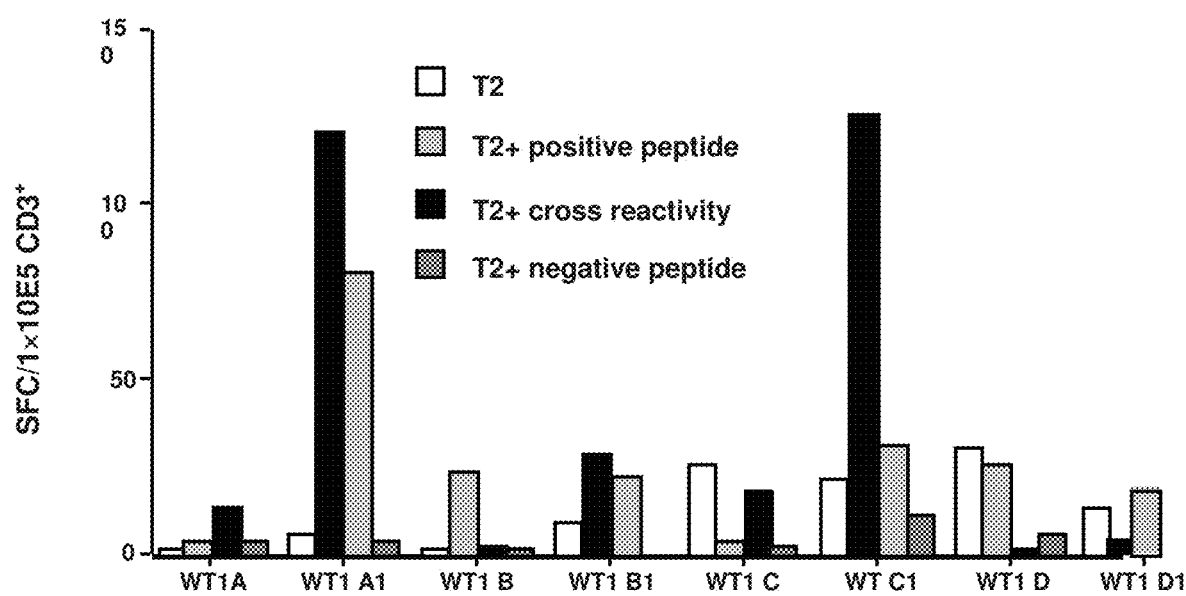
Figure 4A:
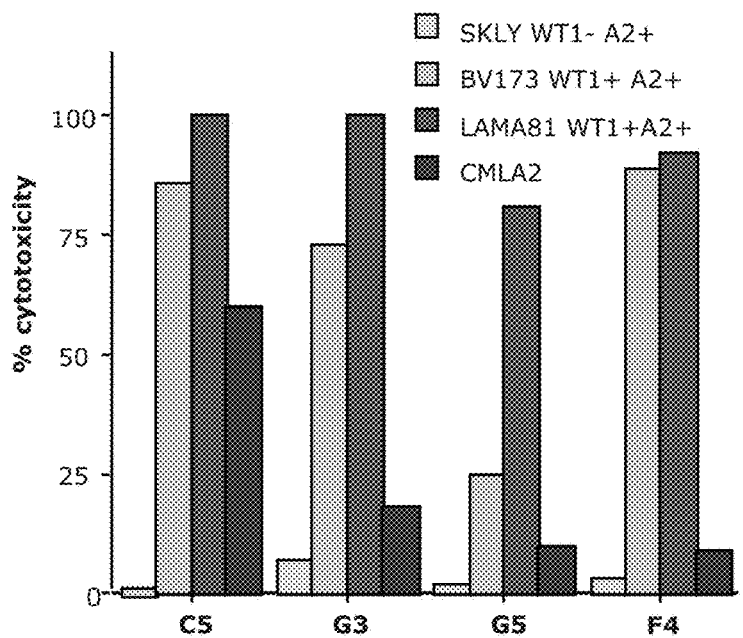
FIG. 4: Cytotoxicity assays using CD8+ T cells stimulated with synthetic WT-1 A1 peptides from a HLA A0201 donor against HLA-matched CML blasts presenting native peptide sequences. A. Bar graphs of results. $1^{st}$ bar in each series: SKLY-16 (WT1−); $2^{nd}$ bar: BV173 (WT1+); $3^{rd}$ bar: LAMA81 (WT1+); $4^{th}$ bar: CMLA (additional negative control). B. Killing curves. Squares: SKLY-16. Diamonds: 697 cells. G3, F4, C5, and G5 are T-cell clones generated from a healthy HLA-A0201 donor after multiple stimulations in vitro. Y axis: percentage of cytotoxicity. X axis: T cell: target cell ratio.
Figure 4B:
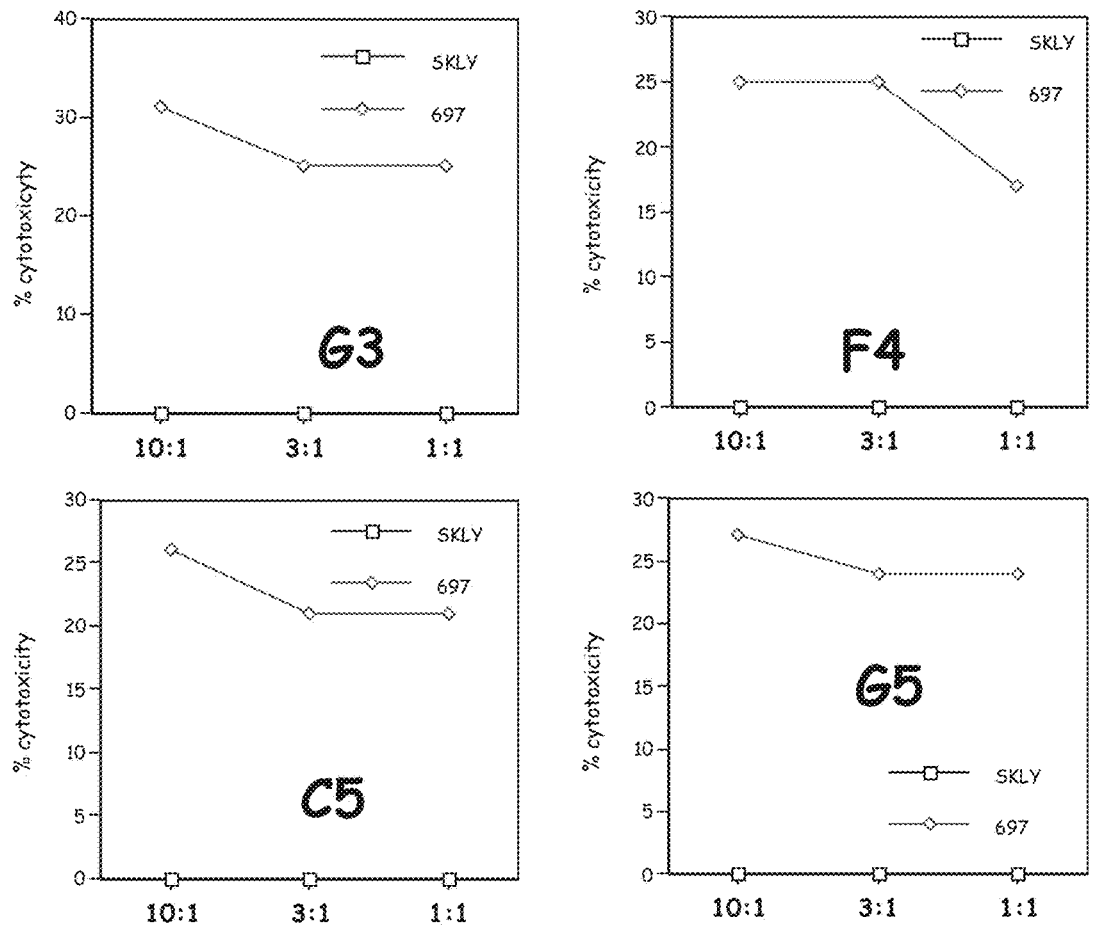

To determine the ability of heteroclitic WT1 peptides to generate immune responses against native and heteroclitic WT peptides, the CD3+ PBMC subpopulation of a healthy donor was isolated and stimulated with autologous monocyte-derived, peptide-pulsed DC, then re-stimulated with peptide-pulsed CD14+ monocytes. The presence of activated, antigen-specific T cells was then determined using pulsed, HLA-matched leukemic cell lines. Several analogue peptides generated greater immune responses (i.e. increased T cell precursor frequency, in comparison with the native peptides) by IFN gamma ELISPOT (FIG. 2A) and chromium release assay (FIG. 2B). Similar results were observed using CD3+ (FIGS. 3B-D) and CD8+ (FIG. 3A) subpopulations of donors. Moreover, CD8+ T cells stimulated with the heteroclitic WT1 peptides cross-reacted with the native WT1 peptides and were able to kill HLA-matched CML blasts (FIGS. 4A-B).

Thus, heteroclitic WT1 peptides of the present invention are able to generate T cells that (a) secrete inflammatory cytokines and (b) perform cytolysis in response to cells presenting WT1 peptides. In addition, the T cells generated by the heteroclitic WT1 peptides recognize both native and heteroclitic WT1 peptides Example 3: Selection of Synthetic WT1 Peptides that Bind HLA Class II Molecules In order to identify WT1 peptides that bind to many different HLA class II molecules with relative high affinities, allele frequencies of HLA-DRB in the North American Caucasian population were determined, using the information available from the NCBI's MHC database (Wheeler D L et al, Database resources of the National Center for Biotechnology Information. Nucleic Acids Res. 2005 Jan. 1; 33:D39-45; Wheeler D L et al, Database resources of the National Center for Biotechnology Information. Nucleic Acids Res. 2006 Jan. 1; 34:D173-80). Using the SYFPEITHI epitope prediction algorithm, 2 peptides that were predicted to bind the HLA-DRB molecules with relatively high affinities were identified from the WT1 sequence (Table 3).

TABLE 3

| | | WT1 native peptides predicted binding to HLA-DR alleles based on SYFPEITHI algorithm (0 (low)-28 (high)). | | | | | |
|---|---|---|---|---|---|---|---|
| Peptide identifier | SEQ ID No: | DRB 101 | DRB 301 | DRB 401 | DRB 701 | DRB 1101 | DRB 1501 |
| Allele frequency | | 17.9% | 18.6% | 13.8% | 25.5% | 10.4% | 15.9% |
| 427 | 1 | 15 | 7 | 12 | 8 | 7 | 4 |
| 423 | 2 | 15 | 17 | 20 | 14 | 10 | 24 |
| 331 | 3 | 28 | 2 | 28 | 18 | 25 | 10 |
| 328 | 4 | 28 | 11 | 28 | 18 | 25 | 20 |

AA sequences of the peptides in Table 3 are LVRHHNMHQRNMTKL (427); RSDELVRHHNMHQRNMTKL (423); NKRYFKLSHLQMHSR (331); and PGCNKRYFKLSHLQMHSRKHTG (328).

Thus, HLA class II-binding WT1 peptides of the present invention bind to HLA class II molecules in a large percentage of the population.

Example 4: HLA Class II Molecule-Binding, WT1 Peptides Stimulate CD4+ T Cells

Materials and Experimental Methods (this and Subsequent Examples)

Preparation of DC and CD4+ Effector Cells

PBMC were Ficoll-purified from blood and resuspended at $5 \times 10^{\wedge}6$/ml in Ex-Vivo-15® medium (BioWhittaker, Walkersville, Md.) containing 1% autologous plasma. After a 2-hour incubation at 37° C., the non-adherent fraction was harvested and washed repeatedly with PBS, then resuspended in media containing $1 \times 10^3$ IU/ml GM-CSF and 0.0032 IU/ml IL-4. On day 2 and 4, the same media was added as re-feed (i.e., ½ the volume of media, containing enough cytokines for the entire dish, was added). On day 5, 10 µg/ml of peptide was added.

On day 6, a maturation cocktail of cytokines was added, and cells were cultured for another 48 hours. The maturation cocktail consisted of: $4 \times 10^2$ IU/ml IL-1-beta, 0.0032 IU/ml IL-4, $1 \times 10^3$ IU/ml IL-6, $1 \times 10^3$ IU/ml GMCSF, 10 µg/ml TNF-alpha, and 1 µg/ml PGE2.

On day 7, DC were harvested and washed twice with RPMI, counted, aliquoted and resuspended at $1 \times 10^6$/ml in X-vivo 15® media (without serum). Peptides were added to a final concentration of 10 μg/ml, and incubated for 2 h, 37° C. and 5% $CO_2$, gently re-suspending every 15 minutes, then washed twice in HBSS and re-suspended in RPMI+5% autologous plasma at an appropriate concentration depending on the number of effectors isolated in the next step.

In addition, on day 7, additional PBMC were used to generate additional DC and $CD3^+$ cells. DC were isolated from the adherent fraction and prepared as described above for the second stimulation of the effector cells on day 14. $CD3^+$ cells were isolated from the non-adherent fraction by negative selection and stimulated with the previously prepared DC by re-suspending the $CD3^+$ cells at a concentration of $2\times10^6$ cells/ml in RPMI+5% autologous plasma, and adding DC at an effector: DC ratio of 20:1 and 10 ng/ml IL-15. Cells were then plated in 2 ml and co-incubated at 37° C. and 5% $CO_2$ for 1 week.

On day 14, the $CD3^+$ cells were stimulated a second time with the second batch of DC in the same manner, except that $1\times10^6$ cells/ml were mixed with DC at an effector: DC ratio of 50:1. On day 18, the same media was added as re-feed. On day 20, the DC from the previous generation were defrosted and incubated in maturation cytokines in X-vivo 15® media. On day 21, the ELISPOT assay was conducted.

ELISPOT Assay

Plates were pre-wet with 30 μl/well 70% alcohol, shaking the plates to ensure coverage of the entire surface area, washed 3 times with 150 μl/well sterile PBS, then incubated overnight at 4° C. with 10 μg/ml coating antibody (anti-INF clone) in PBS, 100 μl/well, wrapped in aluminum foil. Plates were then washed 2 times with 150 μl/well PBS and 1 time with RPMI/10% autologous plasma (AP), then blocked with 150 μl/well RPMI/5% AP for 2 hours at 37° C. PBMC were suspended in RPMI/5% AP at $1\times10^6$/ml. $1\times10^5$ cells and 2 μg of the appropriate peptides were added per well, and the volume brought up to 200 μl/well with media. 1 μl/well of 2.5 mg/ml stock of PHA was added to the control wells. Plates were wrapped in aluminum foil and incubated for 20 hours at 37° C.

To develop, plates were washed 3 times with PBS/0.05% Tween 2 and 3 times with PBS. 100 μl/well anti-INF-gamma-Biotin (Clone 7-B6-1), diluted 1:500 in PBS/0.5% BSA, was added, and plates were incubated for 2 hours at 37° C. After 1 hour and 30 minutes, Avidin-peroxidase Complex (ABC) (Vectastain Elite Kit, Vector) was prepared by adding 1 drop of reagent A and 1 drop of reagent B to 10 ml of PBS/0.1% Tween20, and was stored at room temperature (rt) wrapped in aluminum foil. Plates were washed 3 times with PBS/0.05% Tween and 3 times with PBS, then 100 μl/well of Avidin-peroxidase Complex was added and plates incubated for 1 hour at rt wrapped in aluminum foil, then washed 3 times with PBS/0.05% Tween-20, followed by 3 times with PBS. 100 μl/well of substrate was added, plates were incubated for 4 minutes at rt in the dark, and the reaction was stopped with water. Wells were dried and plates stored overnight in the dark at rt. Spot numbers were automatically determined with the use of a computer-assisted video image analyzer with KS ELISPOT 4.0 software (Carl Zeiss Vision, Germany).

Preparation of Substrate

To prepare solution #1: (acetate buffer), 23.4 ml dd $H_2O$, 2.3 ml 0.1 N Acetic Acid, and 5.5 ml 0.1N Sodium Acetate were mixed. To prepared solution #2, 1 tablet of AEC (Sigma) was dissolved in 2.5 ml of dimethylformamide. Then 1.25 ml of solution #2 was mixed with 23.7 ml of solution #1, 13 μl of 30% $H_2O_2$ was added, and the resulting solution mixed well and filtered using a 0.45 μm filter.

Cross Priming Experiments

A $CD3^+$ in vitro stimulation was performed as described above. $2\times10^6$ immature DCs were incubated with total cellular lysate from $2\times10^6$ tumor cells that was previously prepared by 3 freeze/thaw cycles. Following an 18 hour incubation, maturation cytokines were added to the DCs as described above. $CD3^+$ cells were stimulated 3 times with these autologous mature DCs, after which T cells were tested in an IFN-gamma ELISPOT assay for reactivity against autologous, mature DCs that had been pulsed with individual $CD4^+$ peptides when in the immature state. These DCs were exposed to peptide again during the ELISPOT assay as described above.

Chromium 51 Cytotoxicity Assay

The presence of specific CTL was measured in a standard 4 h-chromium release assay. Target cells were pulsed with 10 microgram (mcg)/ml of synthetic peptides overnight at 37° C. and labeled with 300 μCi of $Na_2^{51}CrO_4$ (NEN Life Science Products, Inc., Boston, Mass.). After extensive washing, target cells were incubated with T cells at an E:T ratio ranging from 100:1 to 10:1. All conditions were performed in triplicate. Plates were incubated for 4 hours at 37° C. in 5% $CO_2$. Supernatant fluids were harvested and radioactivity was measured in a gamma counter. Percent specific lysis was determined from the following formula: 100×[(experimental release minus spontaneous release)/(maximum release minus spontaneous release)]. Maximum release was determined by lysis of radiolabeled targets in 2.5% Triton X-100.

Statistics

Statistical analyses were performed on Statview software (SAS Institute, Cary, N.C.) using a two-tailed unpaired t-test, with the level of statistical significance set at 0.05.

Results

Figure 5A:
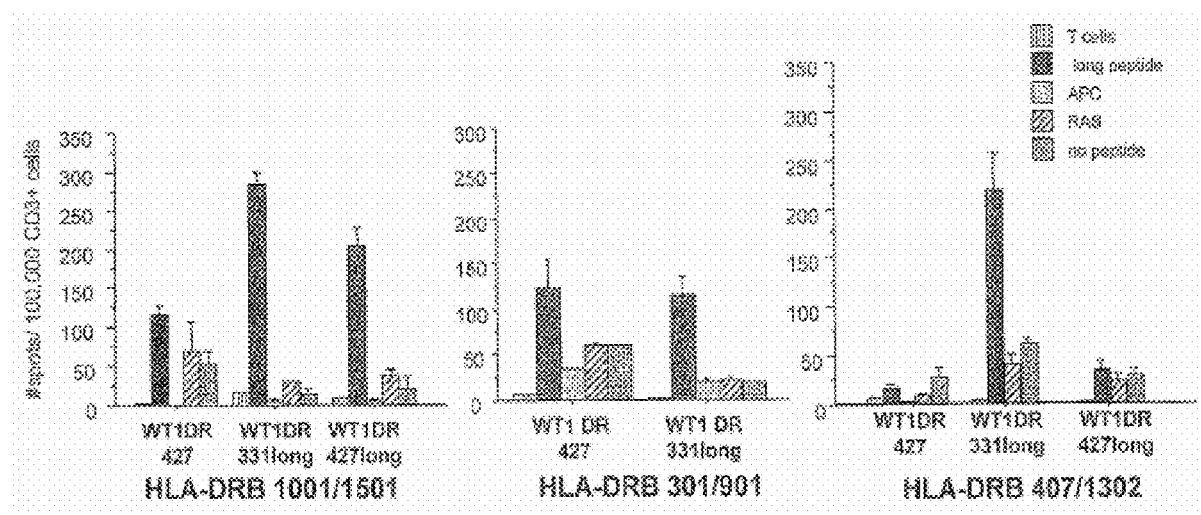
FIG. 5A-B.
Figure 5B:
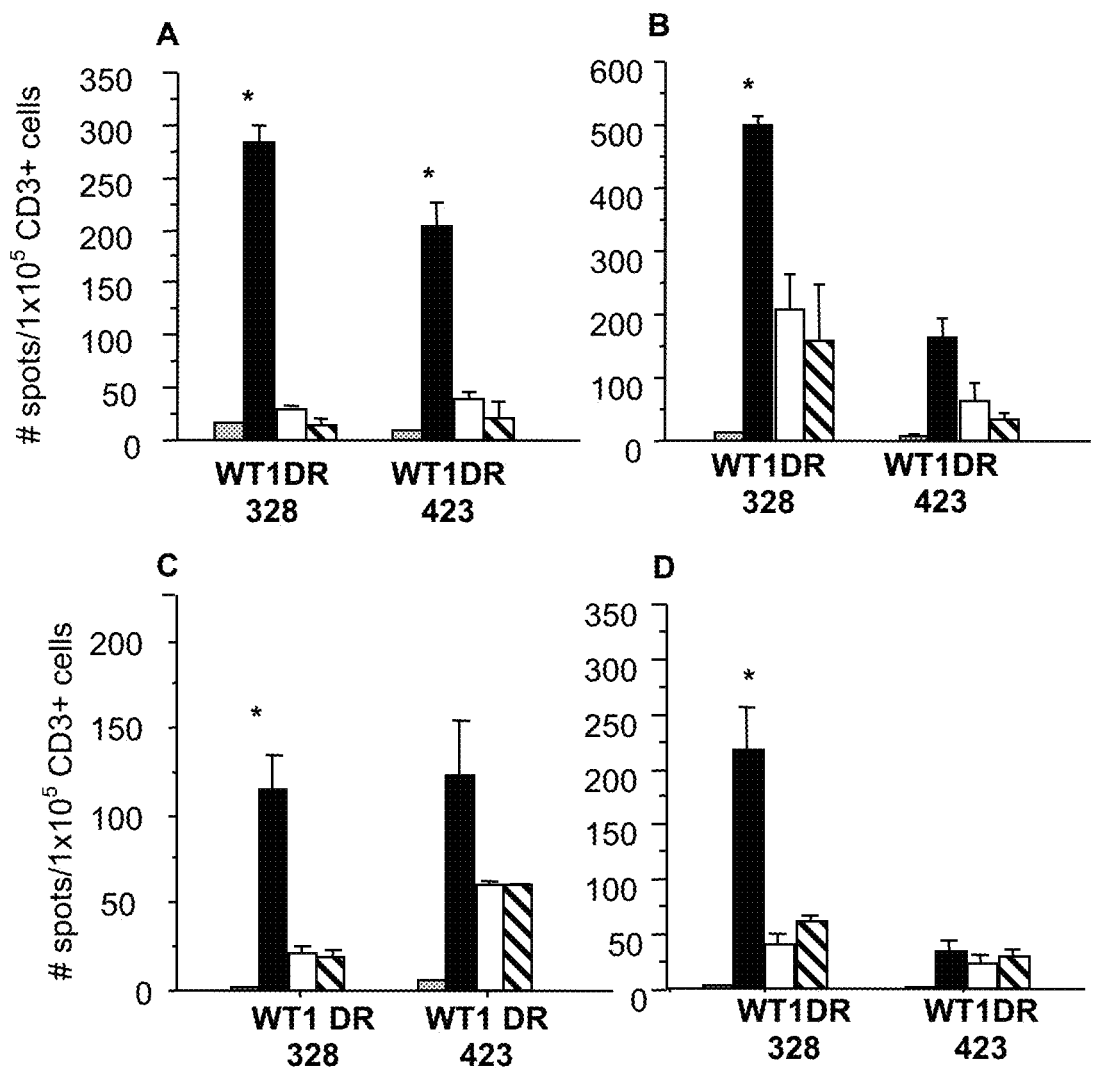

To determine the ability of the HLA class II-binding WT1 peptides of the present invention to stimulate $CD4^+$ T cells, $CD4^+$ PBMC subpopulations of healthy donors were isolated and stimulated with autologous monocyte-derived, peptide-pulsed DC, then re-stimulated with peptide-pulsed $CD14^+$ monocytes. Peptide 328, and to a slightly less extent peptide 423, stimulated a significant peptide specific CD4 response in a variety of donors with different HLA-DRB1 types, as shown by IFN-γ ELISPOT (FIG. 5). As expected, cells stimulated with RAS (irrelevant control peptide) or with APC alone did not produce IFN-γ over background levels.

Thus, HLA class II-binding WT1 peptides of the present invention are able to stimulate T cells that recognize cells presenting WT1 peptides.

Example 5: Identification of Additional HLA Class II Molecule-Binding WT1 Peptides; Mutation of Same to Contain Heteroclitic Class I Molecule Epitopes A WT1 peptide spanning residues 122-140, having the sequence SGQARMFPNAPYLPSCLES (SEQ ID No: 39) was generated and designated "WT1 122." Binding affinity of WT1 122 for common HLA DRB molecules was predicted using the SYFPEITHI epitope prediction algorithm (Rammensee H et al, SYFPEITHI: database for MHC ligands and peptide motifs. Immunogenetics. 1999 November; 50(3-4):213-9). 4 of the 6 HLA-DR types showed improved predicted binding relative to a shorter peptide, WT1 124, having the sequence QARMFPNAPYLPSCL (SEQ ID No: 40) (Table 4). In addition, a peptide termed "WT1 122A1" was generated, comprising the CD8+ heteroclitic WT1A1 peptide YMFPNAPYL (Example 1; SEQ ID No: 6) nestled inside the elongated CD4+ peptide epitope and having the sequence SGQAYMFPNAPYLPSCLES (SEQ ID No: 41). WT1 122A1 also exhibited improved predicted binding over WT1 124 to a broad array of HLA-DR types (Table 4). The average score of WT1 122A1 was 19, with a binding score over 14 (the halfway mark) for all 6 HLA-DR types, compared to an average score of 12 with only one HLA-DR type over 14. Predicted WT1 122A1 binding to the HLA-DR types was also superior to a shorter peptide containing the WT1A1 peptide, "124A1," having the sequence QAYMFPNAPYLPSCL (SEQ ID No: 42).

In addition, a WT1 peptide spanning residues 247-261, having the sequence GATLKGVAAGSSSSVKWT (SEQ ID No: 44) was generated and designated "WT1 244." Binding affinity of WT1 244 for common HLA DRB molecules was predicted as described above for WT 122. Several HLA-DR types showed improved predicted binding relative to a shorter peptide, WT1 247, having the sequence LKGVAAGSSSSVKWT (SEQ ID No: 45) (Table 4).

nized the native short class I peptide WT1A (126-134) and the analog WT1A1 peptide. These experiments were repeated in 5 separate donors. Stimulated T cells recognized WT1DR peptide 328 and WT1DR peptide 122A1 in ⅗ experiments and recognized WT1DR 427 in all experiments. Therefore, despite the low expression of WT1 transcript in the mesothelioma cell lines (see below), WT1 CD4 epitopes of the present invention were processed and presented by HLA class II molecules of mesothelioma cells.

These findings show that peptides of the present invention are (a) taken up and presented by APC in an antigenic form; and (b) are presented by APC exposed to WT1-expressing tumor cells; and (c) APC exposed to WT1 122 and 122A1 peptides elicit the formation of T cells that recognize WT1-expressing tumor cells. Thus, WT1-expressing cells, including mesothelioma and leukemia cells, process and present peptides of the present invention.

TABLE 4

Predicted binding identification of WT1 peptides to class 2 HLA-DR types.

| Peptide sequence | Name | SYFPEITHI Score (high 28-low 0) | | | | | |
|---|---|---|---|---|---|---|---|
| | | DRB-101 | DRB-301 | DRB-401 | DRB-701 | DRB-1101 | DRB-1501 |
| QARMFPNAPYLPSCL | 124 | 12 | 12 | 8 | 8 | 14 | 18 |
| SGQARMFPNAPYLPSCLES | 122 | 22 | 18 | 22 | 16 | 16 | 18 |
| QAYMFPNAPYLPSCL | 124A1 | 22 | 12 | 8 | 8 | 14 | 18 |
| SGQAYMFPNAPYLPSCLES | 122A1 | 27 | 17 | 22 | 18 | 16 | 18 |
| GATLKGVAAGSSSSVKWT | 244 | 31 | 11 | 20 | 24 | 18 | 18 |
| LKGVAAGSSSSVKWT | 247 | 22 | 11 | 20 | 24 | 6 | 18 |
| Frequency of HLA in US Caucasian population | | 17.9% | 18.6% | 13.8% | 25.5% | 10.4% | 15.9% |

Figure 6A:
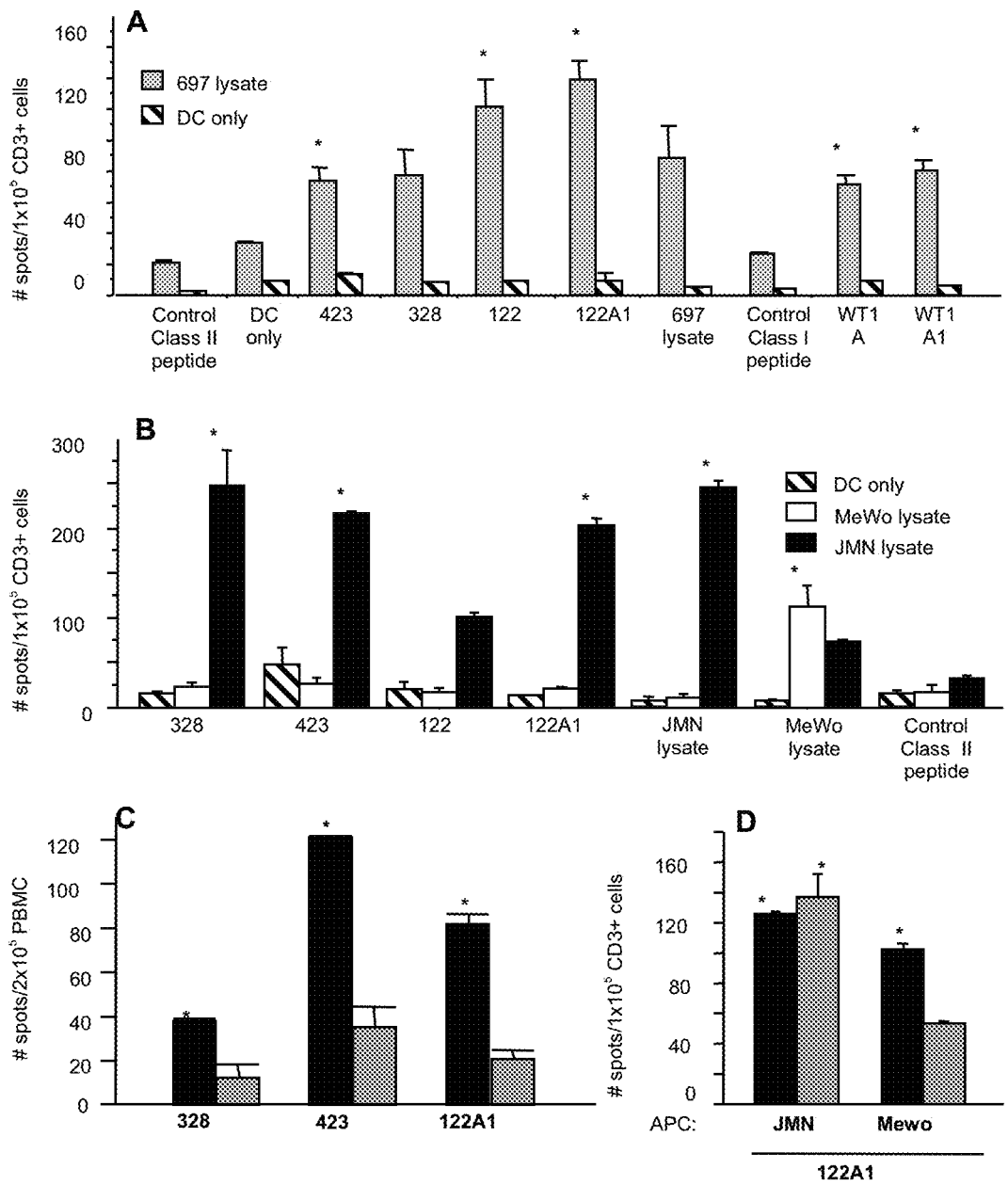
FIG. 6A-B. Peptides of the present invention are processed, presented, and recognized by human T cells.
Figure 6B:
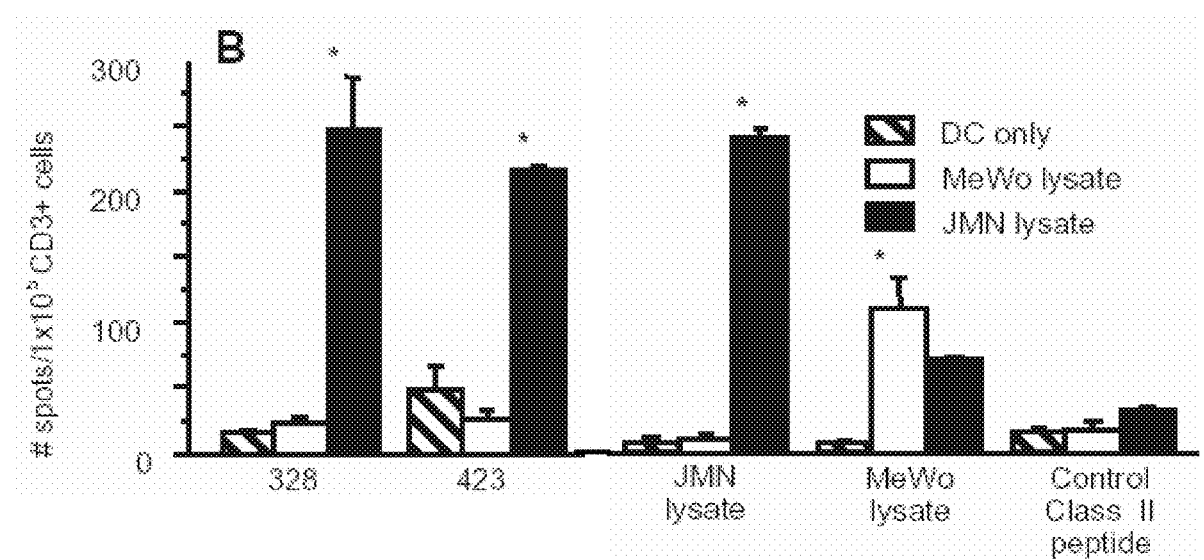

Example 6: WT1-Expressing Cells Process and Present Peptides of the Present Invention Cross-priming studies were performed to determine whether WT1-expressing cells process and present peptides of the present invention and/or the corresponding native peptides. Total tumor lysates were prepared from 3 different cell lines: 697 (WT1+, HLA A0201+), an e1a2 leukemia cell line; JMN (WT1+, HLA A0201+) a biphasic mesothelioma cell line, and as a control, MeWo (WT1−, HLA A0201+), a malignant melanoma cell line. DCs from healthy A0201+ donors were incubated for 18 hours with the tumor lysates and used to stimulate autologous CD3+ T cells. Following 3 stimulations, the T cells were tested for their reactivity to autologous DCs pulsed with the WT1 peptides. T cells that had been stimulated with WT1 positive tumor lysates recognized the individual HLA class II peptides (FIG. 6A-B), while T cells stimulated by DCs pulsed with MeWo lysate did not stimulate WT1 specific T cells. In addition, T cells stimulated with DCs pulsed with 697 tumor lysate recog- Example 7: Stimulation with WT1 122 or 122A1 Stimulates the Production of Antigen-Specific CD4+ and CD8+ T Cells; CD8+ T Cells Elicited by WT1 122A1 Also Recognize the Native Antigen Materials and Experimental Methods CD3+ cells from healthy donors were isolated and stimulated 2 times with peptide, and then recognition of WT1+ JMN cells or WT1− Mewo cells, either alone or with the indicated peptides, was determined by gamma IFN ELISPOT, using the methods described in Example 4.

Results

Figures 7A, 7B:
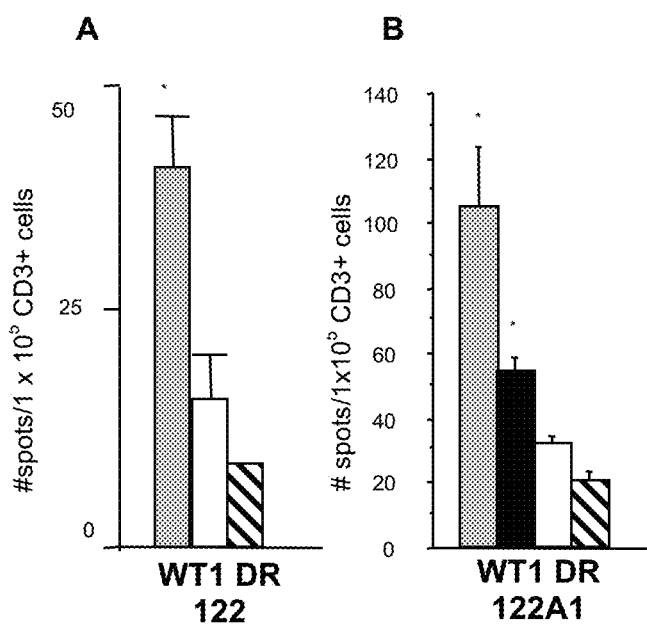
FIG. 7A-B.

T cells were stimulated with autologous, monocyte-derived DC pulsed with WT1 122, 122A1, or negative control peptide, re-stimulated with CD14+ monocytes pulsed with the same peptide, then assayed for formation of antigen-specific T cells by IFN-γ ELISPOT. Stimulation with WT1 122 or 122A1, but not negative control peptide, generated CD4+ T cells that recognized targets pulsed with peptides containing the respective CD4+ epitopes, but not targets pulsed with negative control peptide (FIG. 7A-B).

Figure 7C:
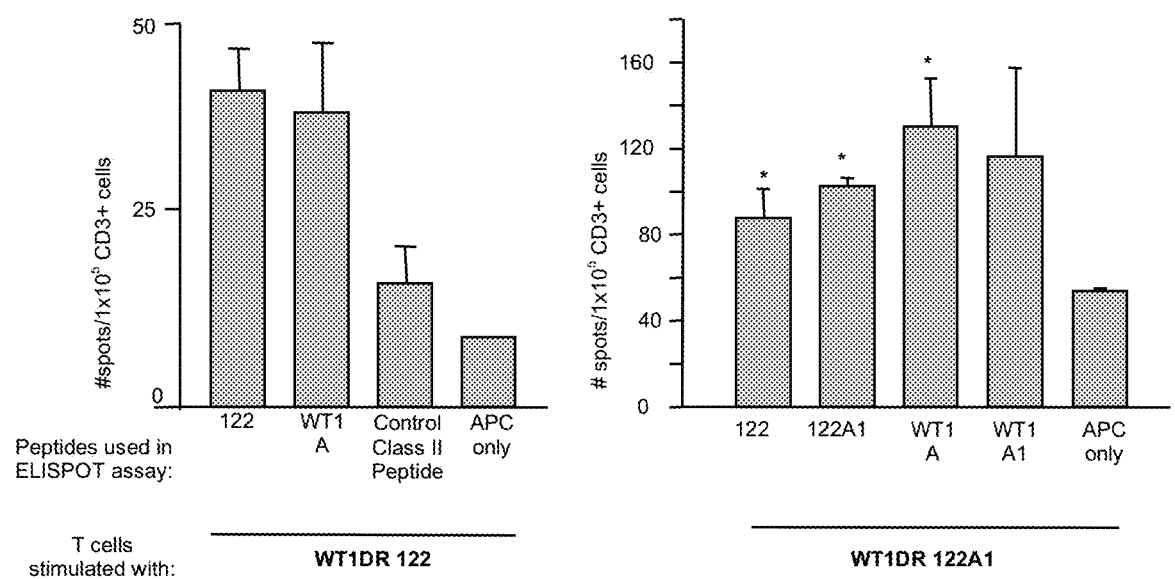
FIG. 7C. WT1DR peptide 122 and 122A1 stimulate CD8+ T cell responses. Left panel: CD3+ T cells from an HLA-A0201/DRB1*1401 donor were stimulated twice with WT1DR 122, then challenged in an IFN-gamma ELISPOT assay with autologous CD14+ cells. Right panel: CD3+ T cells from an HLA-A0201/DRB1*1501 donor were stimulated twice with WT1DR 122A1, then challenged in an IFN-gamma ELISPOT assay with control melanoma cell line MeWo (A0201/DRB1*15XX, WT1−). *-p<0.05 compared to no peptide controls. Y axis represents the number of spots per $1 \times 10^5$ CD3+ cells. X axis shows the different test peptides used in the ELISPOT.

In addition, both WT1DR 122 and WT1DR 122A1 were able to activate CD8+ T cells against the native short epitope WT1A (amino acids 126-134 (FIG. 7C); WT1DR 122A1 was a more potent stimulator.

These stimulation experiments were reproduced in 7 different healthy donors, each with a different HLA-DRB1 type. Up to 15 separate experiments were performed with each WT peptide. WT1DR 328 stimulated peptide specific T cell responses in 11/15 experiments; WT1 DR 423 in 3/14 experiments; WT1DR 122 in 2/5 experiments; and WT1DR 122A1 stimulated T cells that recognized WT1DR 122A1 and WT1DR 122 peptide in 6/6 experiments.

Thus, stimulation with WT1 122 or 122A1 generates antigen-specific CD4+ and CD8+ T cells. In addition, stimulation with WT1 122A1 generates CD8+ T cells that recognize the heteroclitic CD8+ peptide and its native counterpart, whether buried in a longer peptide (WT1 122 or WT1 122A1, respectively) or alone.

Figure 8:
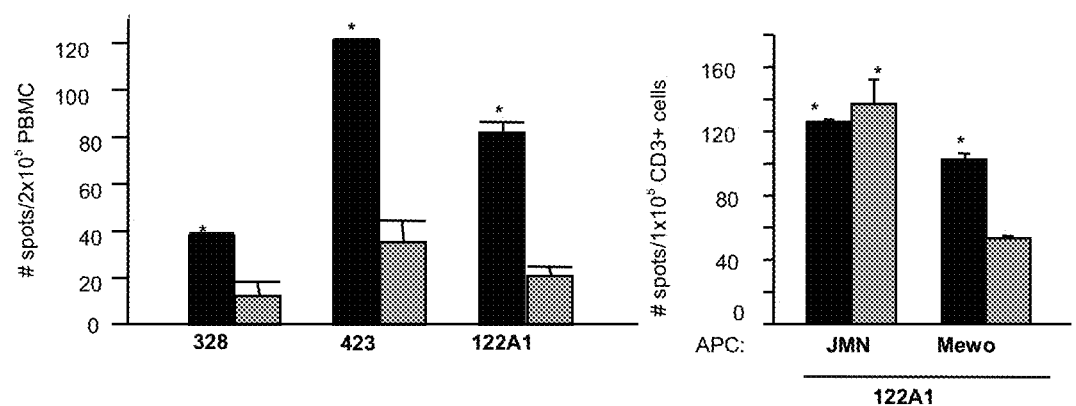
FIG. 8. CD3+ gamma interferon ELISPOT against Mesothelioma cell lines. Left panel: Total PBMCs from an HLA-A0201 donor were stimulated twice with the different WT1DR peptides, then T cells were challenged in an IFN-gamma ELISPOT assay with the following: Mesothelioma H-Meso1A cell line (Black Bars; WT1+, A0201+); control melanoma MeWo cell line (WT1−, A0201+; Grey Bars). *-p≤0.01 compared to MeWo controls. Y axis: number of spots per $2 \times 10^5$ PBMCs. X axis: peptide used for T cell stimulation. Right panel: CD3+ T cells from an HLA-A0201/DRB1*1501 donor were stimulated twice with WT1DR 122A1, then T cells were challenged in an IFN-gamma ELISPOT assay with the following target cells: JMN, an A0201/DRB1*1505 WT1 positive mesothelioma cell line or MeWo, an A0201/DRB1*15XX WT1 negative melanoma cell line. Target cells were either pulsed with WT1DR 122A1 (Black Bars) or not pulsed (Grey Bars). * p<0.05 compared to the unpulsed Mewo target cell. Y axis: number of spots per $1 \times 10^5$ CD3+ T cells. X axis: cell lines used as target cells.

Example 8: Antigen-Specific CD4+ T Cells Generated by Peptides of the Present Invention Recognize WT1-Expressing Tumor Cells To test whether antigen-specific CD4+ T cells generated by peptides of the present invention recognize WT1-expressing tumor cells, peptide-stimulated T cells were challenged in an IFN-gamma ELISPOT with WT-1+ and -negative tumor cells. A sufficient amount of WT1 peptide was presented on the surface of the WT1+ mesothelioma tumor cell for T cells stimulated with individual WT1DR peptides to recognize mesothelioma tumor cells, compared to the control WT1 negative melanoma cells (FIG. 8, left panel). In another experiment, T cells were stimulated by the mutated WT1DR 122A1 and challenged with pulsed and unpulsed targets. When control WT1 negative target cells were pulsed with additional WT1DR 122A1 peptide, IFN-gamma production increased. When WT1 positive target cells were pulsed with additional WT1DR 122A1 peptide, production did not increase, showing that a maximal response was achieved with the native processed peptides (FIG. 8, right panel). Thus, vaccination with peptides of the present invention results in generation of antigen-specific T cells with activity against WT1-expressing tumors.

Example 9: Antigen-Specific CD8+ T Cells Generated by Peptides of the Present Invention Recognize WT1-Expressing Tumor Cells To determine whether antigen-specific CD8+ T cells generated by peptides of the present invention recognize WT1-expressing tumor cells, CD3+ cells from healthy donors were isolated and stimulated with autologous, monocyte-derived DC pulsed with WT1DR 122A1, WT1DR 122, or negative control peptide, re-stimulated with CD14+ monocytes pulsed with the same peptide, then assayed by IFN-γ ELISPOT for formation of antigen-specific T cells that recognized WT1+ JMN cells.

Figure 9:
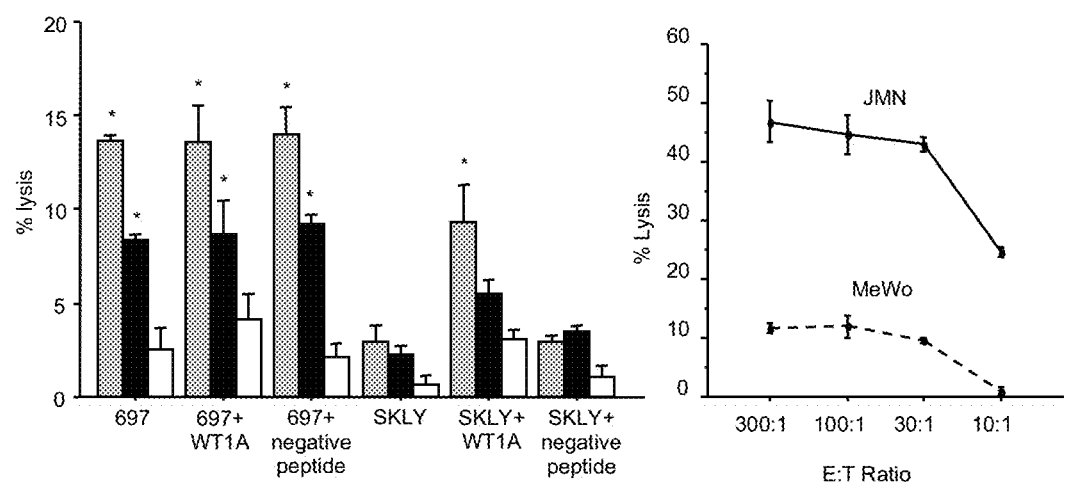
FIG. 9, left panel. CD3+ T cells from an HLA-A0201/DRB1*0101/15XX donor were stimulated twice with WT1DR 122A1, then CD8+ T cells were isolated by negative selection and used as effector cells in a $^{51}$Cr release cytotoxicity assay. CD8+ T cells were incubated with radio-labeled target cells (pulsed or unpulsed 697 (A0201+, WT1+) or SKLY16 (A0201+, WT1−) at 3 different E:T ratios: Grey bars 100:1; Black bars 30:1; White bars 10:1. Y axis: percentage of cytotoxicity. X axis: target cell conditions. *-p<0.05 compared to SKLY16 controls at the same E:T ratio. Right panel: CD8+ T cells isolated as described for the left panel were incubated with radiolabeled JMN (solid line A0201+ WT1+) or MeWo (dashed line A0201+, WT1−) target cells at 4 different E:T ratios: Y axis: percentage of cytotoxicity. X axis: E:T ratios. P was <0.001 compared to MeWo controls.

WT1DR 122A1, but not WT1DR 122, stimulated a sufficient number of CD8+ cells to be cytotoxic to 697, a WT1+ leukemia cell line. The CD8+ T cells did not recognize SKLY16, a WT1 negative B cell lymphoma, unless it was pulsed with WT1A (FIG. 9, left panel), showing antigen specificity of the immune response Similar results were observed in 3/4 different A0201+ donors, each with a distinct HLA-DRB1 type. As expected, the negative control peptides generated no antigen-specific CD8+ T cells. In other experiments, CD3+ T cells generated by stimulation with WT1 122A1 or WT1A1 recognized JMN cells but not negative control MeWo cells, whether alone or pulsed with WT1 122A1 peptide (FIG. 9, right panel). In contrast, CD4+ cells stimulated with WT1DR 122A1 showed no cytotoxicity to either WT1+ mesothelioma or WT1- melanoma cells. Human T cells stimulated 2 times with either the native WT1A or the analog WT1A1 peptide were able to lyse human WT1+ mesothelioma cell lines compared to WT1- control cell lines (9.2% lysis of MeWo vs. 19% lysis of JMN for WT1A stimulated T cells; 22.2% lysis of MeWo vs. 44.8% lysis of JMN for WT1A1 stimulated T cells).

These findings show that vaccination with WT1 122A1 or WT1A1 results in generation of antigen-specific T cells with activity against WT1-expressing tumors. These findings also show that peptides comprising a heteroclitic MHC class I peptide that is associated with an MHC class II peptide stimulate both CD4+ and CD8+ T cells, including antigen-specific T cell responses against the native peptide.

Example 10: WT1 Expression in Human Mesothelioma Cell Lines

Materials and Experimental Methods

Quantitative RT-PCR for WT-1 Transcripts

Total RNA was isolated from cell lines by phenol/chloroform extraction. RNA purity was confirmed by absorbance at 260 nm. The RT reaction was adapted from protocols supplied by Applied Biosystems (Foster City, Calif.). Beginning with 1 mcg total RNA, random hexamers and reverse transcriptase were used to isolate cDNA. For the PCR reaction, cDNA was mixed with the following WT1 primers and probe: forward primer (located on exon 7): 5' CAGGCTGCAATAAGAGATATTTTAAGCT-3' (SEQ ID No: 53); and reverse primer (located on exon 8): 5'-GAAGT-CACACTGGTATGGTTTCTCA-3' (SEQ ID No: 54); Taqman probe (located on exon 7) 5'-CTTACA-GATGCACAGCAGGAAGCACACTG-3' (SEQ ID No: 55). The fluorescent WT1 probe 5'-56-FAM/CTTACA-GATGCACAGCAGGAAGCACACTG/3BHQ_1/-3 (SEQ ID No: 56) was labeled with 6-carboxyfluorescein phosphoramide (FAM) as reporter dye at the 5'-end and with the quencher dye carboxytetramethylrhodamine (TAMRA) at the 3'-end (Integrated DNA Technologies, Coralville, Iowa). The parameters for the PCR reaction were: 2 minutes at 50° C., 10 min at 95° C.; followed by 50 cycles of 15 s at 95° C. and 60 s at 62° C. Each reaction was performed in triplicate, and discrepancies >1 Ct in 1 of the wells were excluded. The Q-RT-PCR reaction and fluorescence measurements were made on the Applied Biosystems 7500 Real Time® PCR System. Control ABL primers and probes were: forward 5'-TGGAGATAACACTCTAAGCATAACTA AAGGT-3 (SEQ ID No: 57; located on EnF-10030)'; reverse 5'-GATGTAGTTGCTTGGGACCCA-3' (SEQ ID No: 58; located on ENR-1063); fluorescent probe 5'-/56 FAM/ CCATTTTTGGTTTGGGCTTCACACCATT/3BHQ_1/-3' (SEQ ID No: 59; located on ENPr-1043).

Results

Figure 10:
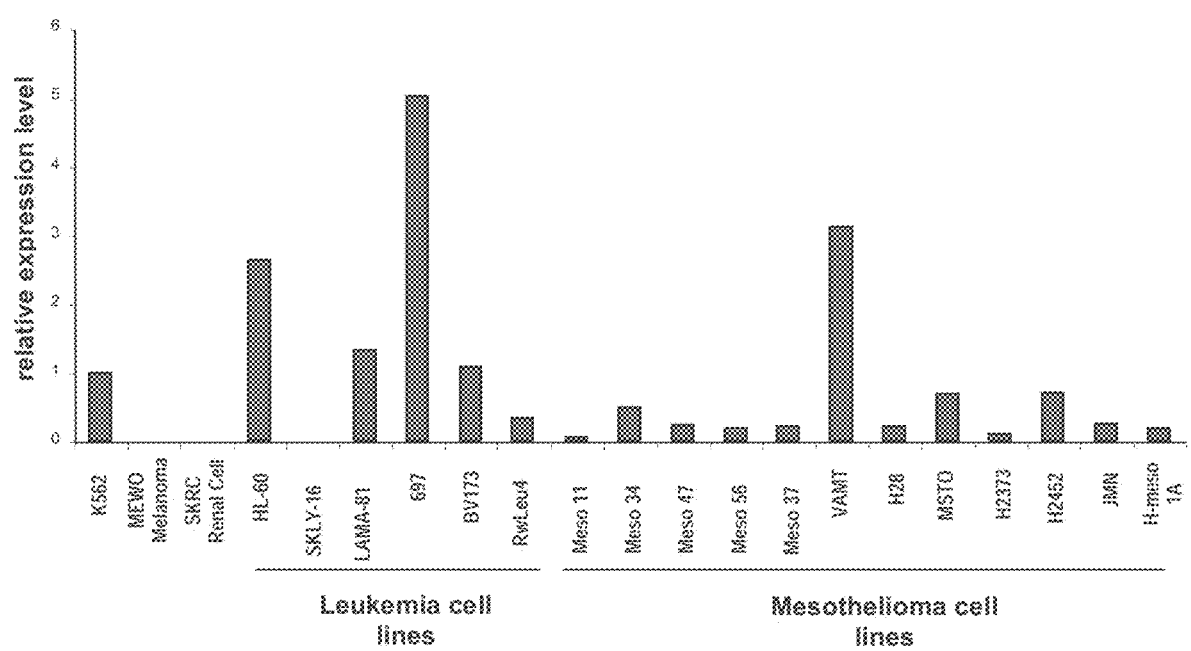
FIG. 10. Quantitative RT-PCR. Relative WT1 expression levels in a variety of hematopoetic and mesothelioma cell lines. WT1 levels are depicted as relative values compared to the human leukemia cell line K562, which is defined as 1.0.

To determine WT1 expression levels in mesothelioma, WT1 transcript levels in a number of human mesothelioma cell lines (sarcomatoid, epitheliod and biphasic) were quantified by RT-PCR and compared to various leukemia cell lines with known WT1 expression. 12/12 mesothelioma cell lines expressed WT1 message, in most cases at a lower level than leukemic cell lines (FIG. 10). By contrast, melanoma (MeWo) and lymphoma (SKLY16) cell lines were WT1 negative. SK-RC-52, a human renal cell carcinoma cell line did not express WT1, despite the low expression of WT1 in adult renal podocytes. Flow cytometry analysis confirmed that all the mesothelioma cell lines expressed class II molecules, and some (JMN and H-2452) expressed class I molecules.

What is claimed is:

1. A method of inducing formation and proliferation of a WT1 protein-specific cytotoxic T lymphocyte (CTL), the method comprising contacting a lymphocyte population with a composition or vaccine comprising the isolated, mutated WT1 peptide SGQAYMFPNAPYLPSCLES (SEQ ID No: 41) or QAYMFPNAPYLPSCL (SEQ ID No: 42) and a physiologically acceptable carrier, adjuvant, diluent, excipient, or with a HLA-A0201 positive, HLA-A0301 positive or HLA-DR positive antigen presenting cell (APC), said APC having been contacted in vitro with SEQ ID NO: 41 or SEQ ID NO: 42, thereby inducing formation and proliferation of a WT1 protein-specific CTL.

2. A method of inducing formation and proliferation of both (a) a WT1 protein-specific CD8+lymphocyte; and (b) a CD4+lymphocyte specific for said WT1 protein, the method comprising contacting a lymphocyte population with a composition or vaccine comprising the isolated, mutated WT1 peptide SGQAYMFPNAPYLPSCLES (SEQ ID No: 41) or QAYMFPNAPYLPSCL (SEQ ID No: 42) and a physiologically acceptable carrier, adjuvant, diluent, excipient, or with a HLA-A0201 positive, HLA-A0301 positive or HLA-DR positive antigen presenting cell (APC), said APC having been contacted in vitro with SEQ ID NO: 41 or SEQ ID NO: 42, thereby inducing formation and proliferation of both (a) a WT1 protein-specific CD8+lymphocyte; and (b) a CD4+ lymphocyte specific for said WT1 protein.

3. A method of treating a HLA-A0201 positive, HLA-A0301 positive or HLA-DR positive subject with a WT1-expressing cancer, or reducing its incidence of relapse, the method comprising administering to said subject a composition or vaccine comprising the isolated, mutated WT1 peptide SGQAYMFPNAPYLPSCLES (SEQ ID No: 41) or QAYMFPNAPYLPSCL (SEQ ID No: 42) and a physiologically acceptable carrier, adjuvant, diluent, excipient, or administering to said subject a HLA-A0201 positive, HLA-A0301 positive or HLA-DR positive antigen presenting cell (APC), said APC having been contacted in vitro with SEQ ID NO: 41 or SEQ ID NO: 42, thereby treating said subject with said WT1-expressing cancer or reducing its incidence of relapse.

4. The method of claim 3, wherein said WT1-expressing cancer is an acute myelogenous leukemia (AML), a malignant mesothelioma, a myelodysplastic syndrome (MDS), a non-small cell lung cancer (NSCLC), or a lymphoma.

5. A method of inducing formation and proliferation of a cytotoxic T lymphocyte (CTL) specific for a WT1-expressing cell, the method comprising contacting a lymphocyte population with a vector comprising a nucleic acid molecule encoding the isolated, mutated WT1 peptide SGQAYMFPNAPYLPSCLES (SEQ ID No: 41) or QAYMFPNAPYLPSCL (SEQ ID No: 42), thereby inducing formation and proliferation of CTL specific for a WT1-expressing cell.

6. A method of inducing formation and proliferation of both (a) a WT1 protein-specific CD8+lymphocyte; and (b) a CD4+lymphocyte specific for said WT1 protein, the method comprising contacting a lymphocyte population with a vector comprising a nucleic acid molecule encoding the isolated, mutated WT1 peptide SGQAYMFPNAPYLPSCLES (SEQ ID No: 41) or QAYMFPNAPYLPSCL (SEQ ID No: 42), thereby inducing formation and proliferation of both (a) a WT1 protein-specific CD8+lymphocyte; and (b) a CD4+ lymphocyte specific for said WT1 protein.

7. A method of treating a HLA-A0201 positive, HLA-A0301 positive or HLA-DR positive subject with a WT1-expressing cancer, or reducing its incidence of relapse, the method comprising administering to said subject a vector comprising a nucleic acid molecule encoding the isolated, mutated WT1 peptide SGQAYMFPNAPYLPSCLES (SEQ ID No: 41) or QAYMFPNAPYLPSCL (SEQ ID No: 42), thereby treating said subject with a WT1-expressing cancer, or reducing its incidence of relapse.

8. The method of claim 7, wherein said WT1-expressing cancer is an acute myelogenous leukemia (AML), a malignant mesothelioma, a myelodysplastic syndrome (MDS), a non-small cell lung cancer (NSCLC), or a lymphoma.

9. The method of claim 1, wherein the composition or vaccine comprises SGQAYMFPNAPYLPSCLES (SEQ ID No: 41).

10. The method of claim 2, wherein the composition or vaccine comprises SGQAYMFPNAPYLPSCLES (SEQ ID No: 41).

11. The method of claim 3, wherein the composition or vaccine comprises SGQAYMFPNAPYLPSCLES (SEQ ID No: 41).

12. The method of claim 3, wherein the composition or vaccine further comprises at least one additional WT1 peptide other than said isolated, mutated WT1 peptide.

13. The method of claim 12, wherein the at least one additional WT1 peptide comprises a heteroclitic peptide.

14. The method of claim 12, wherein the at least one additional WT1 peptide comprises a wild-type WT1 peptide.

15. The method of claim 12, wherein the at least one additional WT1 peptide comprises LVRHHNMHQRNMTKL (SEQ ID No: 1), RSDELVRHHNMHQRNMTKL (SEQ ID No: 2), NKRYFKLSHLQMHSR (SEQ ID No: 3), or PGCNKRYFKLSHLQMHSRKHTG (SEQ ID No: 4), or any combination thereof.

16. The method of claim 15, wherein the composition or vaccine comprises the adjuvant.

17. The method of claim 16, wherein the adjuvant comprises Montanide ISA 51.

18. The method of claim 3, wherein the composition or vaccine comprises the adjuvant.

19. The method of claim 4, wherein the composition or vaccine comprises SGQAYMFPNAPYLPSCLES (SEQ ID No: 41).

20. The method of claim 5 wherein the isolated, mutated WT1 peptide comprises SGQAYMFPNAPYLPSCLES (SEQ ID No: 41).

21. The method of claim 6 wherein the isolated, mutated WT1 peptide comprises SGQAYMFPNAPYLPSCLES (SEQ ID No: 41).

22. The method of claim 7 wherein the isolated, mutated WT1 peptide comprises SGQAYMFPNAPYLPSCLES (SEQ ID No: 41).

23. The method of claim 7, wherein the nucleic acid molecule further encodes at least one additional WT1 peptide other than said isolated, mutated WT1 peptide.

24. The method of claim 23, wherein the at least one additional WT1 peptide comprises a heteroclitic peptide.

25. The method of claim 23, wherein the at least one additional WT1 peptide comprises a wild-type WT1 peptide.

26. The method of claim 23, wherein the at least one additional WT1 peptide comprises LVRHHN MHQR NMTKL (SEQ ID No: 1), RSDELVRHHNMHQRNMTKL (SEQ ID No: 2), NKRYFKLSHLQMHSR (SEQ ID No: 3), or PGCNKRYFKLSHLQMHSRKHTG (SEQ ID No: 4), or any combination thereof.

27. The method of claim 7, wherein the vector further comprises a nucleic acid sequence encoding an immunomodulatory compound.

28. The method of claim 7, further comprising administering a vector encoding an immunomodulatory compound to said subject.

29. The method of claim 7, further comprising administering an immunomodulating compound or adjuvant to said subject.

30. The method of claim 8, wherein the isolated, mutated WT1 peptide comprises SGQAYMFPNAPYLPSCLES (SEQ ID No: 41).

* * * * *